United States Patent [19]

Ajito et al.

[11] Patent Number: 5,407,918

[45] Date of Patent: Apr. 18, 1995

[54] 16-MEMBERED MACROLIDE DERIVATIVES AND PROCESS FOR PRODUCING THE SAME

[75] Inventors: Keiichi Ajito; Ken-ichi Kurihara; Akira Shimizu; Shuichi Gomi; Nobue Kikuchi; Minako Araake; Tsuneo Ishizuka; Aiko Miyata; Osamu Hara; Seiji Shibahara, all of Kanagawa, Japan

[73] Assignee: Meiji Seika Kaisha, Ltd., Tokyo, Japan

[21] Appl. No.: 143,125

[22] Filed: Oct. 29, 1993

[30] Foreign Application Priority Data

| | | | |
|---|---|---|---|
| Oct. 29, 1992 | [JP] | Japan | 4-291438 |
| May 18, 1993 | [JP] | Japan | 5-116231 |
| Aug. 20, 1993 | [JP] | Japan | 5-206731 |
| Sep. 20, 1993 | [JP] | Japan | 5-233561 |
| Sep. 21, 1993 | [JP] | Japan | 5-234809 |

[51] Int. Cl.$^6$ .................... C12P 19/62; C12P 19/60; C07H 17/08; A61K 31/70
[52] U.S. Cl. .................... 514/30; 435/76; 536/7.1
[58] Field of Search .................... 435/76; 536/7.1; 514/30

[56] References Cited

PUBLICATIONS

S. Omura et al., J. Antibiotics, 20(4), 234 (1967).
Y. Matsuhashi et al., ibid., 32(7), 777 (1979).
S. Omura et al., ibid., 33 (8), 911 (1980).
H. Sakakibara et al., ibid., 34(12), 1577 (1981).
K. Tsuzuki et al., ibid., 39(12), 1787 (1986).

Primary Examiner—Herbert J. Lilling
Attorney, Agent, or Firm—Sughrue, Mion, Zinn, Macpeak & Seas

[57] ABSTRACT

16-membered macrolide derivatives represented by the formula (I):

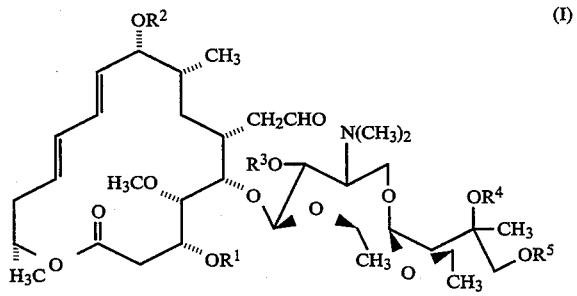

wherein $R^1$ represents a hydrogen atom or a $COR^6$ group, wherein $R^6$ represents a straight-chain alkyl group having 1 to 3 carbon atoms; $R^2$ represents a hydrogen atom or a $COR^6$ group, wherein $R^6$ is as defined above; $R^3$ represents a hydrogen atom or a $COR^6$ group, wherein $R^6$ is as defined above; $R^4$ represents a straight-chain alkyl group having 1 to 4 carbon atoms or a substituted or unsubstituted allyl group; and $R^5$ represents a substituted or unsubstituted, straight-chain or branched alkyl, alkenyl or aralkyl group having 1 to 10 carbon atoms; and pharmaceutically acceptable salts thereof are disclosed. These compounds show excellent and long-acting antimicrobial activities. A novel process for producing these 16-membered macrolide derivatives is further disclosed.

18 Claims, 1 Drawing Sheet

16-MEMBERED MACROLIDE DERIVATIVES AND PROCESS FOR PRODUCING THE SAME

FIELD OF THE INVENTION

This invention relates to novel 16-membered macrolide derivatives, which show excellent and long-lasting antimicrobial activity, and a novel process for producing the same.

BACKGROUND OF THE INVENTION

Sixteen-membered macrolide antibiotics are highly safe and useful in clinical treatments and effective on, for example, Gram-positive bacteria, Mycoplasma and Chlamydia. Thus they have been employed worldwide in various fields including pediatrics. In addition, resistant to these antibiotics is scarcely induced and, compared with 14-membered macrolide, 16-membered macrolide antibiotics exert less interaction with other drugs and less affect on the intestinal tract. Further, they give little irritation (bitterness) at the oral administration. These characteristics make the 16-membered macrolide antibiotics excellent antimicrobial agents for improving the quality of life of patients. Among all, miokamycin (MOM) [Journal of Antibiotics, 29 (5), 536 (1976)] and rokitamycin (RKM) [Journal of Antibiotics, 34 (8), 1001 (1981)] have been frequently used clinically as a semisynthetic 16-membered macrolide antibiotic superior to natural compounds in the action of preventing infection. On the other hand, studies on derivatives of these compounds have been vigorously performed in order to improve the efficacy and safety thereof.

The present inventors conducted biochemical studies on 16-membered macrolide derivatives effective on various Gram-positive bacteria and found so far two fungi capable of specifically removing an acyl group binding to a hydroxyl group at the 3-position of a lactone ring of a 16-membered macrolide (EP-A-526,906 and U.S. Pat. No. 5,219,736). On the other hand, similar biochemical reactions effected by Bacillus subtilis have been already reported [Journal of Fermentation Technology, 57 (6), 519 (1979)].

Subsequently, the present inventors paid their attention to the drug metabolism in MOM and RKM which might be called "16-membered macrolide antibiotics of the second generation". Namely, two acyl groups in the neutral sugar moiety in these antibiotics are removed with esterase in vivo and the neutral sugar moiety is metabolized into mycarose having two free hydroxyl groups. It is reported that the antimicrobial activities in vitro of these metabolites are thus reduced [Yakugaku Zasshi, 102 (8), 781 (1982), Symposium on novel drugs IV, TMS-19-Q, p. 109, 119, 31st General Meeting of Society of Japan Chemotherapy]. Through feedback of these findings to drug design, the present inventors conducted repeated studies on the chemical synthesis of 16-membered macrolide derivatives being stable in vivo and retaining antimicrobial activity even after being metabolized. As a result, they succeeded in the synthesis of a novel derivative, wherein both of two hydroxyl groups in the mycarose moiety of a 16-membered macrolide derivative form ether bonds with alkyl groups, and proved that said compound showed a remarkable long-acting in vitro (EP-A-560,147).

In order to improve the antimicrobial activity and/or pharmacokinetics of 16-membered macrolides, a number of derivatives thereof have been synthesized by partly acylating the hydroxyl groups therein. On the other hand, several groups of workers have already reported the synthesis of derivatives by monoalkylating hydroxyl group(s) in the mycarose moiety of 16-membered macrolides [Chemistry Letters, 769 (1977); JP-A-60-58998; and JP-A-62-234093; the term "JP-A" as used herein means an "unexamined published Japanese patent application"].

First, the present inventors discussed effects of a difference in the structure at the 9-position among midecamycin analogues, from among 16-membered macrolide compounds, on pharmacokinetics. That is to say, midecamycin $A_1$ having a hydroxyl group at the 9-position (Medemycin; MDM) [Journal of Antibiotics, 24 (7), 452 (1971)] and midecamycin $A_3$ having a carbonyl group at the 9-position [ibid., 24 (7), 476 (1971)] were orally administered to animals (mice), followed by observing the pharmacokinetics. As a result, it was confirmed that MDM having a hydroxyl group at the 9-position was superior to midecamycin $A_3$ both in the sustained concentration in serum and in the recovery in urine. Based on these results, it has been judged that a 16-membered macrolide derivative, in particular, a midecamycin analogue having a hydroxyl group at the 9-position is preferred to the one having a carbonyl group at the same position for the improvement in the pharmacokinetics. It has been also reported that, regarding the 13-position of 16-membered macrolides belonging to iso-forms, a derivative having a hydroxyl group is superior to the one having a carbonyl group in the efficacy in vivo [Scientific Reports of Meiji Seika Kaisha, 13, 100 (1973)].

In order to clarify the correlation among structures of 16-membered macrolide compounds, to study biosynthesis of these compounds and to analyze the structures thereof, there have been known methods for reducing a carbonyl group at the 9-position of a 16-membered macrolide compound into a hydroxyl group through a synthetic chemical approach [for example, those described in Journal of Organic Chemistry, 39 (16), 2474 (1974); Journal of Antibiotics, 34 (12), 1577 (1981); and ibid., 39 (12), 1784 (1986)] and through a biochemical approach [for example, those described in JP-A-50-126880; Journal of Antibiotics, 32 (7), 777 (1979); and ibid., 33 (8), 911 (1980)].

The present inventors then paid their attention to the 3-position of a lactone ring of 16-membered macrolide derivatives. Regarding the 3-position of 16-membered macrolide compounds, in particular, leucomycin analogues, correlations among the structures and various activities including pharmacokinetics have been studied in detail [Journal of Antibiotics, 21 (9), 532 (1968)]. At the early stage, it was reported that a compound having a free hydroxyl group at the 3-position of a lactone ring was superior to the corresponding 3-O-acyl compound in the antimicrobial activity in vitro but showed a low concentration in serum in vivo [Hakko to Kogyo, 37 (12), 27 (1979)]. However, subsequent studies have revealed that a certain derivative having a modified neutral sugar moiety sustains a strong antimicrobial activity, even though having a free hydroxyl group at the 3-position, and achieves a high concentration in serum when orally administered to animals of small or middle size [Journal of Antibiotics, 34 (8), 1001, (1981)]. Therefore techniques for removing an acyl group directly binding to a hydroxyl group at the 3-position of a lactone ring have attracted public attention again as a method for enhancing the antimicrobial activity in vitro of a 16-membered macrolide derivative.

The present inventors have recently synthesized novel 16-membered macrolide derivatives having two ether bonds in the mycarose moiety, for example, 4''-O-depropionyl-4''-O-isoamyl-3''-O-methylmidecamycin $A_3$ (EP-A-560,147). Compared with 16-membered macrolide antibiotics put into the market in recent years, these novel 16-membered macrolide derivatives are clearly improved in the maximum concentration in serum and the recovery in urine in animal experiments with the use of mice because the mycarose moiety of these compounds is scarcely attacked by esterase. However, these 16-membered macrolide derivatives are not always satisfactory in the pharmacokinetics. The existence of a carbonyl group at the 9-position, as described above, is considered as one of the factors to be solved for obtaining excellent pharmacokinetics. Thus there has been first required to develop a novel 16-membered macrolide derivative which is stable in vivo, scarcely reduces the antimicrobial activity even after being metabolized and is superior to the derivatives having a carbonyl group at the 9-position and two ether bonds in the mycarose moiety in the pharmacokinetics.

The novel 16-membered macrolide derivative having two ether bonds in the mycarose moiety, for example, 4''-O-depropionyl-4''-O-isoamyl-3-O-methylmidecamycin $A_3$ has enhanced antimicrobial activity on some bacteria belonging to the genus Streptococcus or Branhamella, compared with MOM. However, it is still desired to improve its antimicrobial activity in vitro. By the way, it cannot be expected that the antimicrobial activity in vitro is remarkably improved by reducing the carbonyl group at the 9-position into a hydroxyl group. Thus it is proposed to remove a propionyl group binding to a hydroxyl group at the 3-position of a lactone ring, as described above, as a method for exerting an excellent antimicrobial activity in vitro without considerably enhancing a certain toxicity, such as acute toxicity, inherent to the compound per se. That is to say, it is secondly required to develop a novel 16-membered macrolide derivative which is stable in vivo, scarcely reduces the antimicrobial activity even after being metabolized, shows excellent pharmacokinetics as much as possible and is superior to the novel 16-membered macrolide derivative prepared by the present inventors so far in antimicrobial activity in vitro.

Under these circumstances, it has been required to develop a novel macrolide derivative wherein both of two hydroxyl groups in the mycarose moiety form ether bonds with alkyl groups and, at the same time, an $sp^3$ carbon is located at the 9-position. In fact, there has never been reported such a derivative, either the hydroxyl group at the 3-position of a lactone ring is an acylated hydroxyl group or a free hydroxyl group.

In order to prepare such derivatives, in particular, those having a free hydroxyl group at the 3-position of a lactone ring, in practice, it is necessary to perform a chemical reaction consisting of a plural number of steps (EP-A-560,147) involving regio- and stereo-selective glycosylation for introducing a neutral sugar and two continuous steps of microbial conversion. Therefore, the cost and time for preparing these derivatives are not always completely satisfactory. Furthermore, an activator, which is dangerous and to be handled with care, should be stoichiometrically used in the above-mentioned glycosylation and there are some problems in scaling up thereof. Accordingly, it has been thirdly required to establish a process for producing a 16-membered macrolide derivative, wherein two hydroxyl groups in the mycarose moiety form ether bonds with alkyl groups, by chemical synthesis without using any glycosylation.

In the chemical modification of a 16-membered macrolide antibiotic, there have been known some cases wherein an alkyl group is introduced into the secondary hydroxyl group at the 4''-position of the mycarose moiety via no glycosylation. For example, Ōmura, Sano et al. introduced an alkyl group into the secondary hydroxyl group at the 4''-position of the mycarose moiety by protecting a hemiacetal hydroxyl group formed at the 3,18-position of spiramycin I (JP-A-60-58998; and JP-A-60-239494). On the other hand, Yoshioka et al. modified two hydroxyl groups in the mycarose moiety of a 16-membered macrolide derivative with dialkyl tin and introduced, for example, a benzyl group to the secondary hydroxyl group, which was one of the two hydroxyl groups, at the 4''-position (JP-A-62-234093). However, there has never been reported so far a reaction whereby an alkyl group is introduced into the tertiary hydroxyl group at the 3''-position of the mycarose moiety of a 16-membered macrolide derivative via no glycosylation.

SUMMARY OF THE INVENTION

An object of the present invention is to provide novel 16-membered macrolide derivatives showing strong and long-acting antimicrobial activity.

Another object of the present invention is to provide a process for producing these derivatives simply, economically and safely.

To attain the above-mentioned objects, the present inventors have repeatedly conducted synthetic chemical and biochemical studies and have succeeded in producing novel 16-membered macrolide derivatives represented by the formula (I):

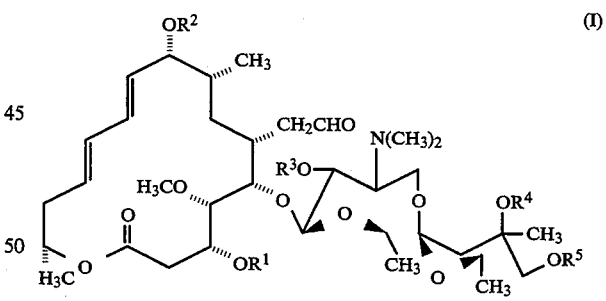

wherein $R^1$ represents a hydrogen atom or a $COR^6$ group, wherein $R^6$ represents a straight-chain alkyl group having 1 to 3 carbon atoms; $R^2$ represents a hydrogen atom or a $COR^6$ group, wherein $R^6$ is as defined above; $R^3$ represents a hydrogen atom or a $COR^6$ group, wherein $R^6$ is as defined above; $R^4$ represents a straight-chain alkyl group having 1 to 4 carbon atoms or a substituted or unsubstituted allyl group; and $R^5$ represents a substituted or unsubstituted, straight-chain or branched alkyl, alkenyl or aralkyl group having 1 to 10 carbon atoms; or a pharmaceutically acceptable salt thereof.

The present inventors have also succeeded in the efficient synthesis of 16-membered macrolide derivatives represented by the formula (III):

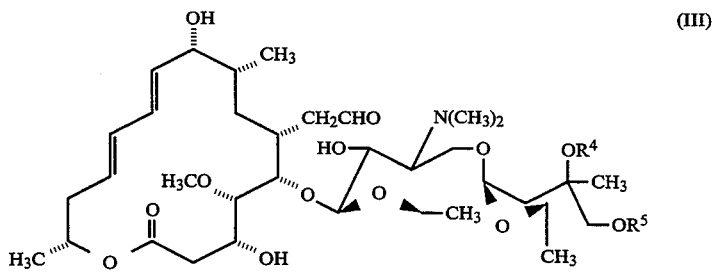
(III)

wherein $R^4$ represents a straight-chain alkyl group having 1 to 4 carbon atoms or a substituted or unsubstituted allyl group; and $R^5$ represents a substituted or unsubstituted, straight-chain or branched alkyl, alkenyl or aralkyl group having 1 to 10 carbon atoms; or a salt thereof from a compound represented by the formula (II):

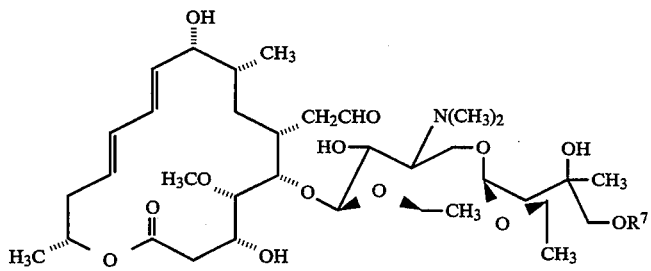
(II)

wherein $R^7$ represents a straight-chain or branched aliphatic acyl group having 2 to 5 carbon atoms; or a salt thereof.

DETAILED DESCRIPTION OF THE INVENTION

Figure 1:
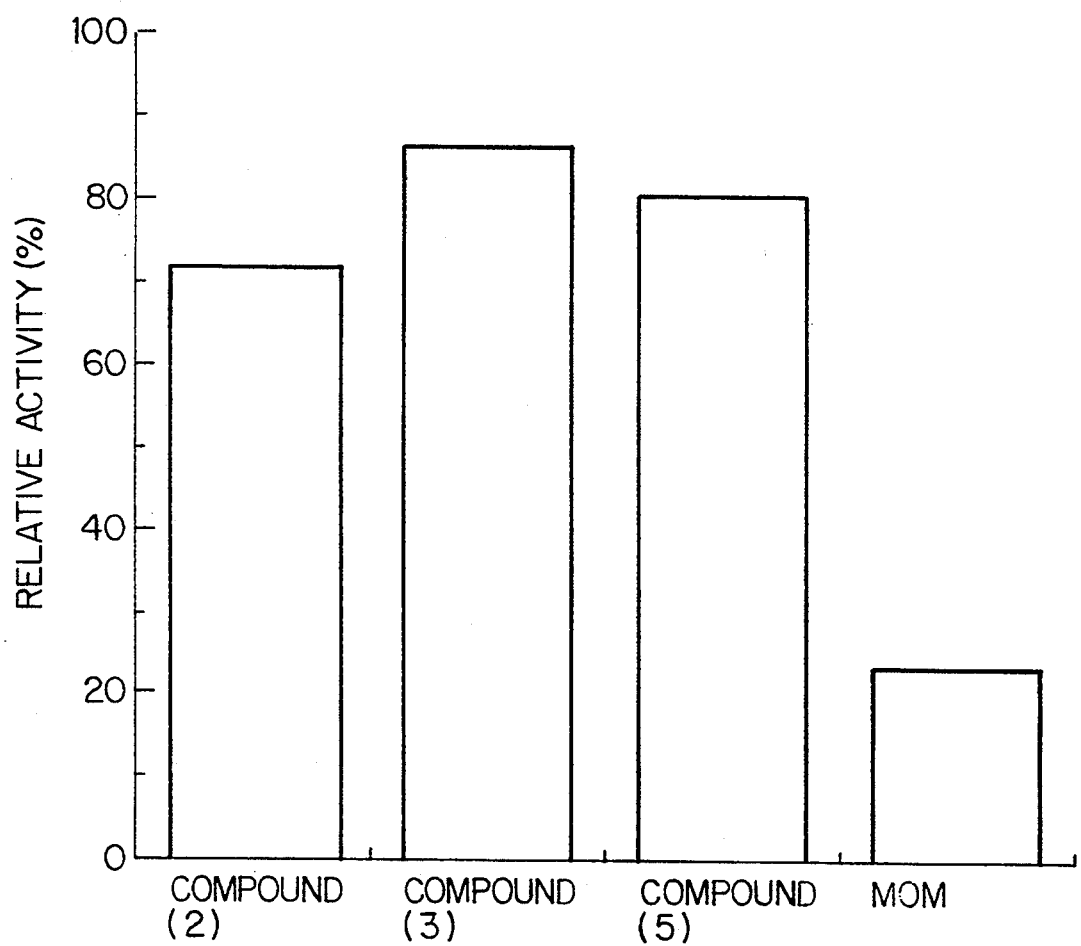
FIG. 1 graphically shows antimicrobial activity on *M. luteus* of the compounds (2), (3) and (5) and miokamycin (MOM) after incubation in thawed rat plasma at 37° C. for 24 hours. The starting activity of each compound in plasma was referred to as 100%.

In the formula (I), specific examples of the alkyl, alkenyl and aralkyl groups represented by $R^5$ include a methyl group, an ethyl group, a propyl group, a butyl group, a pentyl group, an isoamyl group, a hexyl group, an allyl group , and a benzyl group, which may be substituted with an azido group or a nitro group.

In the formula (II), examples of the aliphatic acyl group represented by $R^7$ include an acetyl group, a propionyl group, a butyryl group, an isovaleryl group and an isobutyryl group.

The process for producing the 16-membered macrolide derivatives according to the present invention is described in detail below.

The compounds represented by the formula (IV) which are included in the compounds represented by the formula (I),

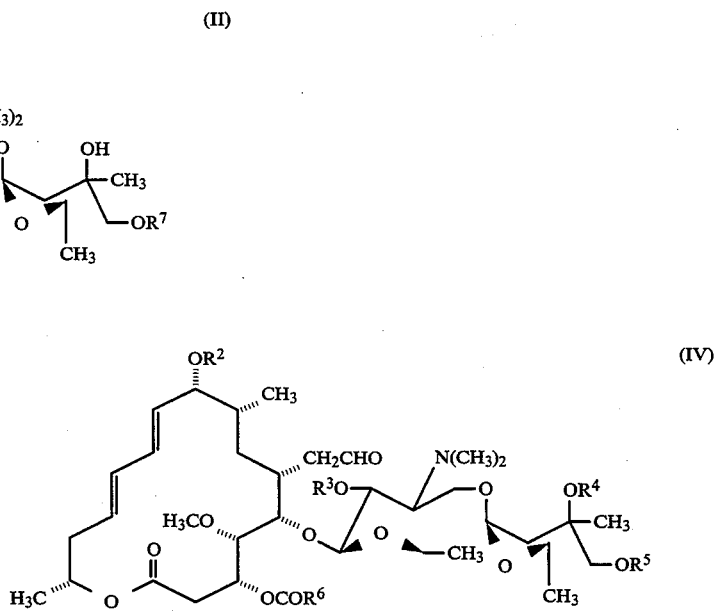
(IV)

wherein $R^2$ represents a hydrogen atom or a $COR^6$ group, wherein $R^6$ represents a straight-chain alkyl group having 1 to 3 carbon atoms; $R^3$ represents a hydrogen atom or a $COR^6$ group, wherein $R^6$ is as defined above; $R^4$ represents a straight-chain alkyl group having 1 to 4 carbon atoms or a substituted or unsubstituted allyl group; $R^5$ represents a substituted or unsubstituted, straight-chain or branched alkyl, alkenyl or aralkyl group each having 1 to 10 carbon atoms; and $R^6$ represents a straight-chain alkyl group having 1 to 3 carbon atoms; provided that $R^2$ and $R^3$ are not hydrogen atoms simultaneously; and pharmaceutically acceptable salts thereof can be produced by reducing a carbonyl group at the 9-position of 16-membered macrolide derivatives in which both of two hydroxyl groups in the mycarose moiety form ether bonds with alkyl groups, as described in EP-A-560,147, into a hydroxyl group having a natural configuration through microbial conversion using a mutant of *Streptomyces mycarofaciens* SF-837 strain (for example, SF2772 strain) belonging to Actinomycetes, followed by a chemical modification.

The compounds represented by the formula (IV) can be easily produced from compounds represented by the formula (V):

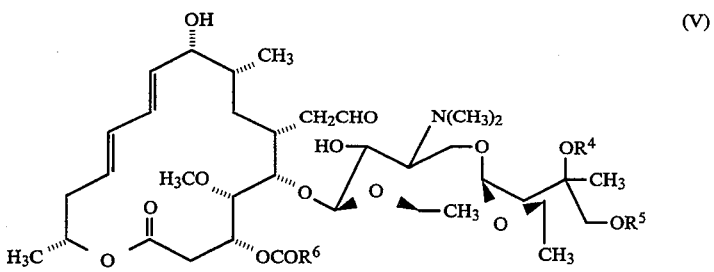

(V)

wherein $R^4$ represents a straight-chain alkyl group having 1 to 4 carbon atoms or a substituted or unsubstituted allyl group; $R^5$ represents a substituted or unsubstituted, straight-chain or branched alkyl, alkenyl or aralkyl group each having 1 to 10 carbon atoms; and $R^6$ represents a straight-chain alkyl group having 1 to 3 carbon atoms; or salts thereof by a known selective or unselective chemical synthesis on the hydroxyl group(s) at the 9-position and/or the 2'-position in the mycaminose moiety [Hakko to Kogyo, 37 (12), 1171 (1979)]. The compounds represented by the formula (V) which is also a novel compound according to the present invention can be produced through microbial conversion of compounds represented by the formula (VI):

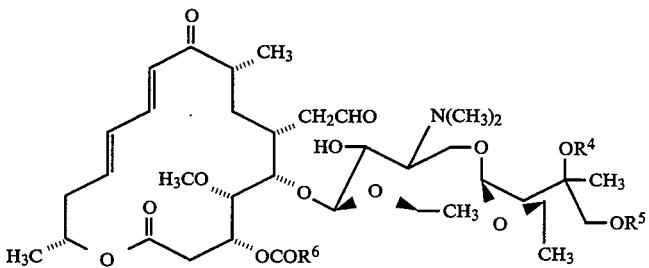

(VI)

wherein $R^4$ represents a straight-chain alkyl group having 1 to 4 carbon atoms or a substituted or unsubstituted allyl group; $R^5$ represents a substituted or unsubstituted, straight-chain or branched alkyl, alkenyl or aralkyl group each having 1 to 10 carbon atoms; and $R^6$ is a straight-chain alkyl group having 1 to 3 carbon atoms; which is prepared from, for example, midecamycin $A_3$ by synthetic chemical techniques (EP-A-560,147), or salts thereof with the use of a mutant of Streptomyces mycarofaciens SF-837 (for example, SF2772 strain) belonging to Actinomycetes. Streptomyces mycarofaciens SF2772 has been deposited with Fermentation Research Institute of Agency of Industrial Science and Technology, of 1-3, Higashi 1-chome, Tsukuba-shi, Ibaraki 305, Japan, under the accession number FERM BP-4465.

The processes for producing the compounds of the formula (V) from the compounds represented by the formula (VI) are not restricted to biochemical techniques, for example, microbial conversion or treatments with enzymes produced by living organisms. For example, these compounds can be produced by synthetic chemical techniques involving protection and deprotection of the aldehyde group at the 18-position [Journal of Organic Chemistry, 39. (16), 2474 (1974)]. However the reduction of the carbonyl group at the 9-position into a hydroxyl group having a natural configuration by synthetic chemical techniques cannot always give satisfactory results, in view of the stereo-selectivity of said reaction and the yields at the protection/deprotection steps (in particular, the acetalization at the 18-position). Thus the present inventors have examined in detail the reduction at the 9-position by biochemical techniques.

It has been already reported a biochemical technique whereby a carbonyl group at the 9-position of midecamycin $A_3$ is reduced into a hydroxyl group having a natural configuration [Journal of Antibiotics, 32 (7), 777 (1979)]. On the basis of this fact, the methodology per se for reducing a carbonyl group at the 9-position of a 16-membered macrolide derivative having two alkyl groups in the mycarose moiety into the corresponding hydroxyl group by a biochemical technique can be easily assumed. In fact, when a derivative represented by the formula (VI), for example, 4''-O-depropionyl-4''-O-isoamyl-3''-O-methylmidecamycin $A_3$ is subjected to microbial conversion with the use of Streptomyces mycarofaciens SF2772 strain belonging to Actiomycetes to be used in the present invention, the target derivative represented by the formula (V), for example, the compound (3) shown below can be obtained.

A mutant of Streptomyces mycarofaciens SF-837 strain belonging to Actinomycetes and producing MDM, for example, the SF2772 strain, to be used in this process is a midecamycin analogue-non-producing strain. In the above microbial conversion, this strain produces no substance with antimicrobial activity other than the conversion substrates and the conversion products, which makes it highly useful therein. Any strain other than the SF2772 strain can be used in the present invention as long as it produces no midecamycin analogue. Such strains can be constructed by artificial mutagenesis of the SF-837 strain by known methods.

Streptomyces mycarofaciens SF-837 has been deposited with Fermentation Research Institute of Agency of Industrial Science and Technology under the accession number FERM P-262 and with American Type Culture Collection under the accession number of ATCC21454 and now available to the public. The above-mentioned microbial conversion is not restricted to those performed with the use of a midecamycin analogue-non-producing strain but can be carried out with the use of a strain capable of producing said substance. Furthermore, the carbonyl group at the 9-position of a 16-membered macrolide compound can be biochemically reduced by using a midecamycin-producing strain or a mutant thereof. In general, strains producing 16-membered macrolide antibiotics having a hydroxyl group at the 9-position such as platenomycin-producing strains [Journal of Antibiotics, 28 (10), 789 (1975)] and maridomycin-producing strains [Agricultural and Biological Chemistry, 43 (6), 1331 (1979)] and mutants thereof are usable therefor.

On the other hand, the microbial conversion of the present invention is characterized by being free from any control of a complicated enzyme system, for example, adding NADPH or strictly adjusting hydrogen ion concentration. When performed not only in known media commonly employed for culturing Actinomycetes but also in media being poor in nutrients, the process of the present invention with the use of a microorganism can achieve conversion at a higher efficiency and more efficient isolation of the conversion product. The microbial conversion is described in greater detail in Examples given hereinafter.

A 16-membered macrolide derivative having two alkyl groups in the mycarose moiety and a carbonyl group at the 9-position can be reduced to the corresponding product having been reduced at the 9-position in the following manner.

To perform the microbial conversion of the present invention, first, the microorganism to be used is seed-cultured in a liquid medium and then a 16-membered macrolide compound is added to the seed thus obtained. Although the macrolide compound (substrate) may be added at any stage following the growth of the seed, it is preferable to add the substrate 24 hours after the initiation of the seed culture in which the cell density ranges from 10 to 15% (w/v). The substrate is usually added at a ratio of from 0.01 mg/ml to 2 mg/ml.

As nutrients of the medium, those which have been known and employed for culturing Actinomycetes are usable. It is preferable to use glucose as a carbon source and polypeptone as a nitrogen source. The efficient conversion and rapid isolation and purification of the conversion product can be achieved by performing the microbial conversion in a medium containing less solid matters. The medium may further contain inorganic salts capable of forming sodium, potassium, calcium, magnesium, cobalt, chlorine, phosphate and sulfate ions and the like, if necessary. Examples of the inorganic salts include sodium chloride, potassium chloride, calcium chloride, magnesium sulfate, cobalt chloride, dipotassium hydrogenphosphate and the like. Furthermore, organic and inorganic substances capable of promoting the growth of the strain and accelerating the conversion of the substrate may be optionally added thereto. Usable as such organic substances are glutamic acid, aspartic acid, adenine, uracil, inositol, vitamin $B_{12}$ and the like. Examples of the inorganic substances include sodium chloride, potassium chloride, magnesium sulfate, cobalt chloride, dipotassium hydrogenphosphate and the like.

A suitable culture method is aerobic culture. Submerged culture is particularly preferred. Although the culture temperature may range from 24° to 32° C., the culture is carried out at around 28° C. in most cases. The conversion efficiency of the substrate varies depending on the employed medium and culture conditions. Either in shaking culture or in tank culture, the accumulation of the conversion product usually reaches the maximum level within 1 to 72 hours. When the accumulation of the conversion product in the culture medium reaches the maximum level, the culture is ceased and the target substance is isolated and purified from the culture medium.

To harvest the target conversion product from the above-mentioned culture medium, the cells are removed from the medium after the completion of the culture and the culture medium thus being free from any solid matters is then made alkaline. Then it is extracted with a water-immiscible organic solvent, such as butanol, ethyl acetate, chloroform and methylene chloride. The conversion product is sustained in the organic solvent layer. To further purify the conversion product, a chromatography may be carried out with the use of an adsorbent such as silica gel or alumina. In the case of the purification of a small amount of the product, preparative TLC may be effectively employed. However, the method for the purification of the conversion product is not restricted to the method with the use of an adsorbent as described above. Namely, techniques commonly used for the purification of natural or synthetic organic compounds, including gel filtration, counter-current distribution chromatography and the like, are also applicable thereto. When the conversion product is obtained in the form of a free base, it may be further converted into the corresponding salts by using pharmaceutically acceptable inorganic or organic acids. That is to say, not only the conversion products in the form of a free base but also salts thereof fall within the scope of the present invention.

Based on the present invention, novel and useful substances can be created by, for example, selectively acylating the hydroxyl group at the 9- or 2'-position of a compound represented by the formula (V) or its salt in accordance with the known method [Hakko to Kogyo, 37 (12), 1171 (1979)] or subjecting the hydroxyl group at the 9-position of the compound to allylic rearrangement into the 11- or 13-position in the presence of a dilute acid in accordance with the known method [Chemical and Pharmaceutical Bulletin, 18 (8), 1501 (1970); Scientific Reports of Meiji Seika Kaisha, 12, 85 (1972); and Journal of Antibiotics, 35 (11), 1521 (1982)]. For example, the compound (4) is synthesized by selectively acetylating the hydroxyl group at the 9-position of the compound (3) [the compound of the formula (V) wherein $R^4$ is a methyl group, $R^5$ is an isoamyl group and $R^6$ is an ethyl group] in accordance with a known method (JP-A-48-13380).

The compounds represented by the formula (VII) which is included in the compounds represented by the formula (I):

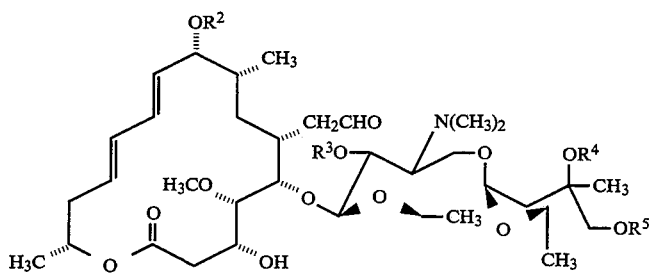

(VII)

wherein $R^2$ represents a hydrogen atom or a $COR^6$ group, wherein $R^6$ represents a straight-chain alkyl group having 1 to 3 carbon atoms; $R^3$ represents a hydrogen atom or a $COR^6$ group, wherein $R^6$ is as defined above; $R^4$ represents a straight-chain alkyl group having 1 to 4 carbon atoms or a substituted or unsubstituted allyl group; and $R^5$ represents a substituted or unsubstituted, straight-chain or branched alkyl, alkenyl or aralkyl group each having 1 to 10 carbon atoms; provided that $R^2$ and $R^3$ are not hydrogen atoms simultaneously, or pharmaceutically acceptable salts thereof can be produced by removing an acyl group directly binding to the hydroxyl group at the 3-position of the 16-membered macrolide derivatives represented by the formula (V) in which two hydroxyl groups in the mycarose moiety form ether bonds with alkyl groups and a hydroxyl group is located at the 9-position and the reducing said group into a free hydroxyl group by microbial conversion with the use of Phialophora PF1083 strain (U.S. Pat. No. 5,219,736 and EP-A-526,906) which is one of fungus strains, followed by a chemical modification. The compound represented by the formula (VII) can be easily produced from a compound represented by the formula (III):

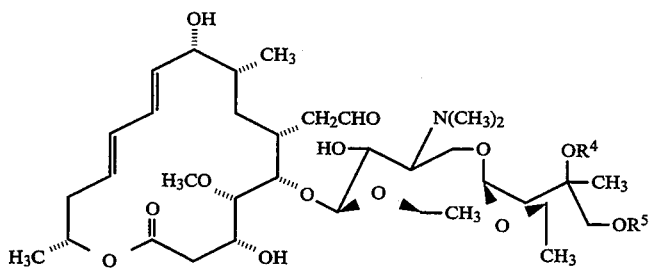

(III)

wherein $R^4$ represents a straight-chain alkyl group having 1 to 4 carbon atoms or a substituted or unsubstituted allyl group; and $R^5$ represents a substituted or unsubstituted, straight-chain or branched alkyl, alkenyl or aralkyl group each having 1 to 10 carbon atoms; or salts thereof by a known selective or unselective chemical synthesis on the hydroxyl group(s) at the 9-position and/or the 2'-position in the mycaminose moiety [Hakko to Kogyo, 37 (12), 1171 (1979)]. In addition to the chemical synthesis route as described below, the compounds represented by the formula (III) according to the present invention can be produced by the microbial conversion of compounds represented by the formula (V):

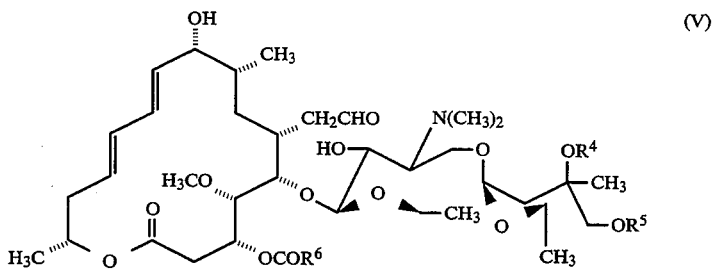

(V)

wherein $R^4$ represents a straight-chain alkyl group having 1 to 4 carbon atoms or a substituted or unsubstituted allyl group; $R^5$ represents a substituted or unsubstituted, straight-chain or branched alkyl, alkenyl or aralkyl group each having 1 to 10 carbon atoms; and $R^6$ represents a straight-chain alkyl group having 1 to 3 carbon atoms; or salts thereof by using Phialophora PF1083 strain which is one of fungus strains.

As described above, there is a possibility that antimicrobial activity in vitro of a 16-membered macrolide derivative having a modified neutral sugar might be enhanced without significantly reducing its concentration in serum in vivo in animals of small or middle size by removing an acyl group binding to the hydroxyl group at the 3-position of a lactone ring. However, it is not unusual that a series of compounds called 16-membered macrolide (derivatives) in general show different properties depending on basic skeleton structure. For example, effects of the structure at the 3-position on the biochemical stability of lactone ring and synthetic chemical deacylation of the acyl group binding to the hydroxyl group at the 3-position largely vary depending on the basic skeleton structure of the lactone rings.

Namely, in spiramycin analogues having a glycoside bond at the hydroxyl group at the 9-position of a lactone ring, it is reported that spiramycin II having an acetyl group binding to the hydroxyl group at the 3-position shows a sustained antimicrobial activity in rat plasma, since its lactone ring is hardly cleaved, compared with spiramycin I having a free hydroxyl group at the 3-position [Journal of Antibiotics, 36 (4), 442 (1983)]. According to this report, spiramycin I M4 having a cleaved lactone ring and hemiacetal formed at the 3,18-position, was isolated. In the case of rokitamycin which is a 16-membered macrolide derivative having a free hydroxyl group at the 3-position, however, no compound with a cleaved lactone ring has been reported as a major metabolite when orally administered to man and dog (Symposium on novel drugs IV, TMS-19-Q, p. 109, 119, 31st General Meeting of Society of Japan Chemotherapy].

An acyl group binding to the hydroxyl group at the 3-position of a lactone ring can be chemically removed in the following manner. When hydrolyzed with an alkali, most of 16-membered macrolide compounds would give not efficiently the target compounds having a free hydroxyl group at the 3-position but mainly compounds unsaturated at the 2-, and 3-positions. However, it is reported that the deacylation (deacetylation) was achieved by hydrolyzing a tylosin derivative with an acid [Carbohydrate Research, 169, 241 (1987)]. In a series of compounds generally called 16-membered macrolide derivatives, the reactivity at the 3-position and physicochemical and biochemical effects of said site upon the whole molecule are highly specific to the substrate, as discussed above. It is, therefore, difficult to propose the methodology of the modification and conversion of these compounds in general.

A derivative represented by the formula (V), for example, 4''-O-depropionyl-4''-O-isoamyl-3''-O-methyl-midecamycin $A_1$ [compound (3)] falls within the leucomycin group depending on its lactone moiety and two hydroxyl groups in its mycarose moiety have been both modified. It is assumed that the antimicrobial activity in vitro of this compound might be enhanced without significantly reducing its concentration in serum in vivo in animals of small or middle size by removing the propionyl group binding to the hydroxyl group at the 3-position to thereby give a free hydroxyl group. Thus this compound is depropionylated at the 3-position. In order to efficiently achieve the target conversion, it is seemingly preferable to employ a biochemical method, in particular, a microbial conversion or a conversion using an enzyme produced by a living organism, by taking account of the physicochemical stability of the derivative represented by the formula (V).

A biochemical method for removing the acyl group binding to the hydroxyl group at the 3-position of the lactone ring of a 16-membered macrolide compound has been already reported [Journal of Fermentation Technology, 57 (6), 519 (1979), and U.S. Pat. No. 5,219,736 and EP-A-526,906]. Thus the methodology per se for removing the acyl group (for example, a propionyl group) binding to the hydroxyl group at the 3-position of a lactone ring of a 16-membered macrolide compound having two alkylated hydroxyl groups in the mycarose moiety [for example, a derivative represented by the formula (V)]by a biochemical means can be easily assumed. When a derivative represented by the formula (V), for example, the compound (3) is converted with the use of a microorganism Phialophora PF1083 strain which is one of fungus strains, the target derivative represented by the formula (III), for example, the compound (12) is obtained.

The Phialophora PF1083 strain has been deposited with Fermentation Research Institute of Agency of Industrial Science and Technology under the accession number FERM BP- 3960. The strain to be used for the microbial conversion is not restricted to the PF1083 strain but other strains [for example, Preussia PF1086 strain (FERM BP-3961) which is one of fungus strains found by the present inventors] is usable therefor, though the PF1083 strain is superior in conversion efficiency. The more efficient conversion and the more efficient isolation of the conversion product can be achieved by performing the above-mentioned microbial conversion in a medium rich in a carbon source, compared with known media commonly used for culturing fungi. The microbial conversion using the PF1083 strain or the PF1086 strain can be carried out by adding the conversion substrate to the culture of the strain, in which the cell density ranges from 20 to 30% (w/v), to give a concentration of 0.1 to 2 mg/ml and incubating the resulting culture at 24° to 30° C., preferably 26° C., for 3 to 10 days. This microbial conversion is described in detail in Examples given hereinafter or U.S. Pat. No. 5,219,736 and EP-A-526,906.

The compounds represented by the formula (I) in which free hydroxyl groups are located respectively at the 3- and 9-positions of a lactone ring, and both of the two hydroxyl groups in the mycarose moiety form ether bonds with alkyl groups, can be produced by using the compounds of leucomycin Fr group (i.e., known naturally occurring 16-membered macrolide antibiotics), such as leucomycin $A_7$ [Journal of Antibiotics, Ser. A, 20 (4), 234 (1967)], as a starting compound by the steps comprising (1) silylation, (2) 4''-deacylation, (3) 4''-alkylation, (4) 3''-alkylation and partial deprotection and (5) deprotection. The compounds represented by the formula (III):

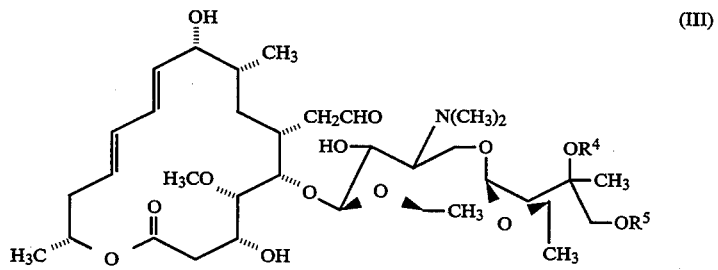

wherein $R^4$ represents a straight-chain alkyl group having 1 to 4 carbon atoms or a substituted or unsubstituted allyl group; and $R^5$ represents a substituted or unsubstituted, straight-chain or branched alkyl, alkenyl or aralkyl group having 1 to 10 carbon atoms; or salts thereof can be efficiently synthesized from the compounds represented by the formula (II):

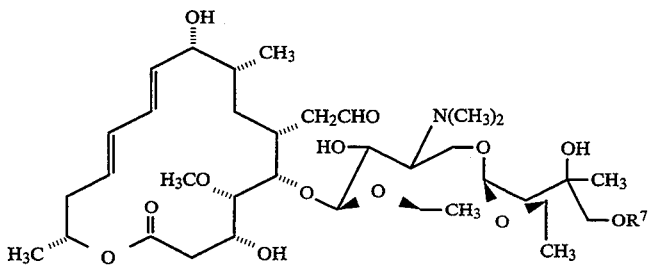

(II)

wherein $R^7$ represents a straight-chain or branched aliphatic acyl group having 2 to 5 carbon atoms; or salts thereof. In addition to the above-mentioned microbial conversion route, the compounds represented by the formula (III) can be produced by chemical synthesis in accordance with the following reaction scheme 1.

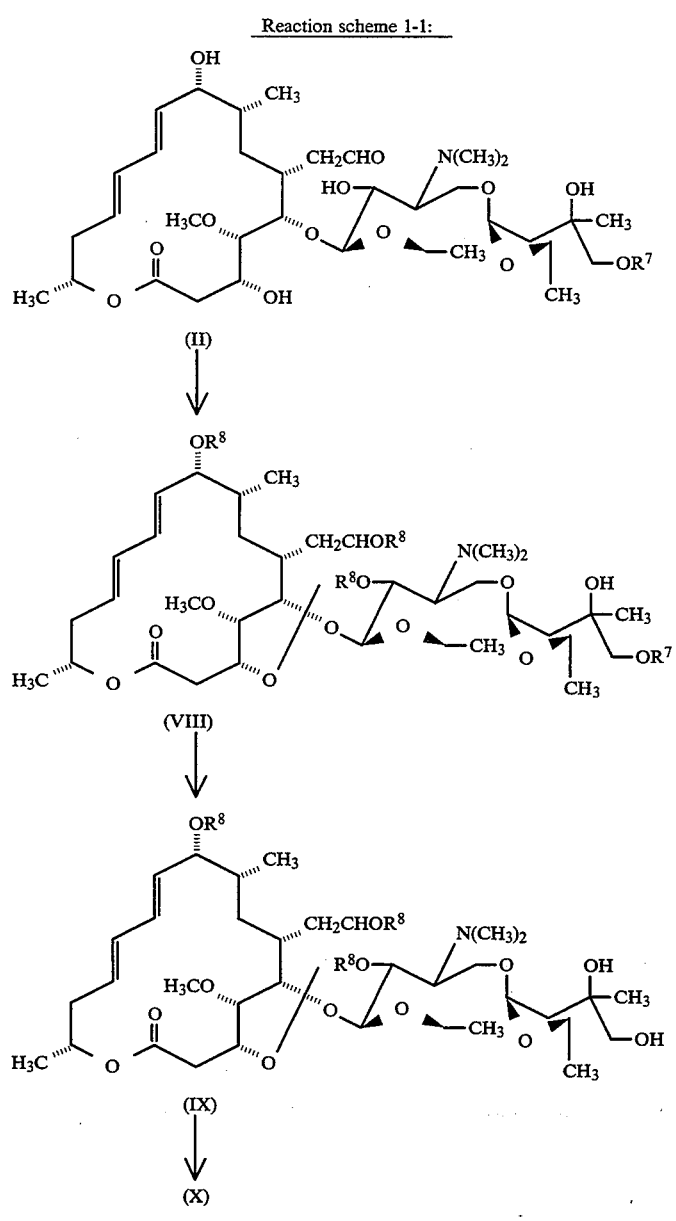

Reaction scheme 1-2:

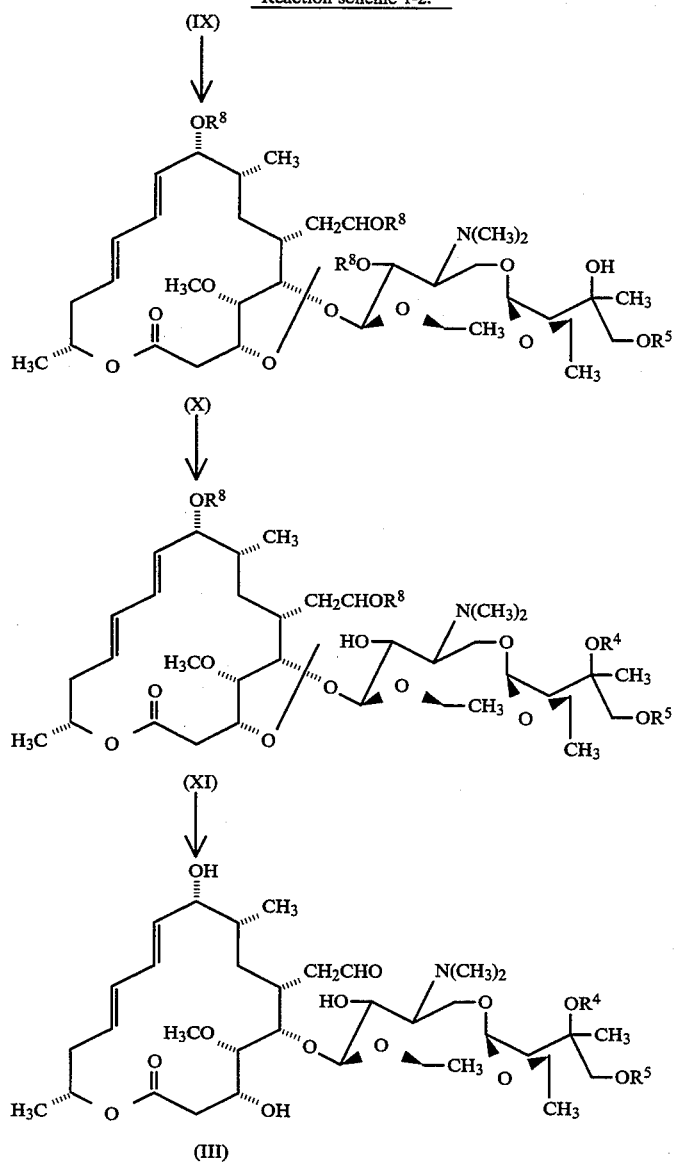

There have been known several methods for introducing an alkyl side chain into a free hydroxyl group to thereby form an ether bond, which are fundamentally a modified Williamson reaction using a strong base. However, there have been known few reactions for forming an ether bond under mild conditions, except some relatively highly reactive alkylations such as methylation, allylation and benzylation. In the case of 14-membered macrolide compounds, a C-methyl group (at the 2-position) and a C-ethyl group (at the 13-position) are mainly located adjacent to an ester bond in a lactone ring. In the case of 16-membered macrolide compounds such as leucomycins, on the other hand, a hydrogen atom (at the 2-position) and a C-methyl group (at the 15-position) are mainly located adjacent thereto. Accordingly, the ester bond in a 14-membered lactone is significantly more stable under basic conditions than the ester bond in the 16-membered lactone of leucomycin, mainly due to the steric hindrance and electronic factors at the 2-position. For example, the methylation of the secondary hydroxyl group in the neutral sugar moiety of a 14-membered macrolide compound easily proceeds under the protection of other hydroxyl groups [Journal of Antibiotics, 43 (5), 566 (1990)].

Namely, 16-membered macrolide compounds, in particular, leucomycins contain many functional groups which are unstable under strongly basic conditions, for example, (1) in the above-mentioned ester bonds, (2) the vicinity of the 3-position of a lactone ring and (3) aldehyde groups. In order to efficiently and successively introduce alkyl groups into the secondary (4"-position) and tertiary (3"-position) hydroxyl groups in the mycarose moiety, it is seemingly ideal to improve and modify a method for protecting spiramycin I with a silyl group (JP-A-60-58998, JP-A-60-239494), the usefulness of which on the alkylation at the 4"-position has been proved by Ōmura, Sano, et al., and to apply the method thus established to leucomycins.

A hydroxyl group and an aldehyde group of compounds of the leucomycin Fr group [J. Antibiotics, 28(6), 401 (1975)], which are naturally occurring 16-membered macrolide antibiotics, can be protected with silyl groups in the following manner. The compound represented by the formula (II), wherein $R^7$ is an acyl group, namely, a single compound of the leucomycin Fr group or a mixture of these compounds or salt(s) thereof are reacted with a necessary or excessive amount of a silylating agent in the presence of a base to give the compounds of the formula (VIII), wherein $R^7$ is an acyl group and $R^8$ is a silyl protective group, having a hemiacetal hydroxyl group formed at the 3,18-position and hydroxyl groups at the 9- and 2'-positions each of which has been silylated or salts thereof. For example, leucomycin $A_7$ [the compound of the formula (II) wherein $R^7$ is a propionyl group] is reacted with t-butyldimethylsilyl chloride (TBDMSCl) in dimethylformamide (DMF) in the presence of imidazole. Thus the compound (17) [the compound of the formula (VIII) wherein $R^7$ is a propionyl group and $R^8$ is a t-butyldimethylsilyl (TBDMS) group] having a hemiacetal hydroxyl group formed at the 3,18-position and hydroxyl groups at the 9- and 2'-positions, namely, three hydroxyl groups in total, each of which has been t-butyldimethylsilylated is obtained at a high yield. [In the structural formulae of the compounds represented by the formulae (VIII), (IX), (X) and (XI) in the reaction scheme 1, the relative locations in the space (in front and in rear) of the bond between the oxygen atom at the 3-position and the carbon atom at the 18-position and another bond between the oxygen atom at the 5-position and the carbon atom at the 1'-position have never been clarified so far.]

Regarding the stereochemistry at the 18-position, one of the diastereomer is dominantly produced. Namely, another diastereomer at the 18-position observed in the protection of spiramycin I [Journal of Antibiotics, 37 (7), 750 (1984)] is not obviously formed. On the other hand, it cannot be denied that the diastereomer at the 18-position might be formed as a side product depending on the employed silyl protective group, the silylation conditions and the reaction substrate. However, said isomer may be either separated or not in the practice of the present invention.

In addition to the TBDMS group, other silyl groups, such as isopropyldimethylsilyl group, ethyldimethylsilyl group, may be used as the silyl group to be used in said protection step. In particular, isopropyldimethylsilyl group and the like are applicable to the process according to the present invention. As the silylating agent for introducing the TBDMS group, reagents commonly usable in the conversion of hydroxyl group into TBDMS, such as $TBDMSOClO_3$, $TBDMSOSO_2CF_3$ and TBDMSCN, can be used, in addition to the above-mentioned TBDMCl. However, it is preferable to use the silylating agent in an amount of 3 equivalents or in excess of the leucomycin compound. Examples of the base to be used in the silylation, in addition to imidazole, include pyridine, dimethylaminopyridine, lutidine and triethylamine. The base is generally used in an amount of not less than 3 equivalents of the leucomycin compound. It is preferable to use imidazole in an amount of 6 equivalents or more of the leucomycin compound. In addition to DMF, acetonitrile, methylene chloride and tetrahydrofuran (THF) or the like may be used as the reaction solvent, though reactions with the use of DMF frequently achieve preferable results. This protection step efficiently proceeds within a temperature range of from 0° to 80° C. and the reaction time ranges from 1 hour to several days. The reaction can be preferably carried out at 40° to 60° C. for several to 24 hours.

Then, the acyl side chain at the 4"-position in the mycarose moiety of the compound represented by the formula (VIII) is chemically removed. In the compound represented by the formula (VIII), a silyl group has been introduced into the hemiacetal hydroxyl group formed at the 3,18-position, the aldehyde group is protected and the 7-membered ring moiety involving these groups is fused to the 16-membered lactone. Compared with 16-membered macrolide derivatives having a free hydroxyl group at the 3-position and a free aldehyde group and not being fused, the stability of the lactone ring of the compound represented by the formula (VIII) per se under strongly basic conditions is extremely elevated. The acyl group binding to the hydroxyl group at the 4"-position of the compound of the formula (VIII) can be selectively removed by a common alkali-treatment without cleaving the lactone ring. However, the yield is not always satisfactory. Thus the present inventors have paid their attention to the fact that the compound of the formula (VIII) has extremely low polarity and examined the possibility of the deacylation at the 4"-position by a heterogeneous reaction with the use of a phase transfer catalyst. As a result, they have succeeded in the quantitative removal of the acyl group at the 4"-position in the mycarose moiety.

For example, the compound (17) [the compound of the formula (VIII) wherein $R^7$ is a propionyl group and $R^8$ is a TBDMS group] is dissolved in benzene and vigorously stirred at room temperature together with a 25% aqueous solution of sodium hydroxide in the presence of tetra-n-butylammonium hydrogensulfate. Thus the compound (18) [the compound of the formula (IX) wherein $R^8$ is a TBDMS] can be obtained at a high efficiency. This heterogenous reaction is usually performed by vigorously stirring a mixture of a strongly basic aqueous layer with an organic solvent (not homogeneously miscible with water), in which the compound represented by the formula (VIII) is dissolved, in the presence of a phase transfer catalyst. The strong base to be dissolved in the aqueous layer may be either sodium hydroxide or potassium hydroxide, preferably with a high concentration, for example, not less than 10% (w/w). Examples of the water-immiscible organic solvent include benzene, toluene, xylene, n-pentane, hexane, cyclohexane, methylene chloride and 1,2-dichloroethane and benzene is particularly preferred. Usable as the phase transfer catalyst are tetra-n-butylammonium bromide, tetra-n-butylammonium chloride, benzyltriethylammonium bromide, benzyltriethylammonium chloride and tetra-n-butylammonium hydrogensulfate. This catalyst may be used in an amount of from catalytic amount to several equivalents based on the compound represented by the formula (VIII). In usual, it is used in an amount of 1 equivalent. The mixing ratio of the aqueous layer and the organic solvent ranges generally from 1:3 to 3:1, preferably from 1:2 to 1:1. The reaction easily proceeds at a temperature of from 5° to 40° C. Although the stirring efficiency contributes to the shortening of the reaction time and the improvement in the yield, the reaction is usually completed within 10 minutes to several hours. The reaction can be preferably carried-out at room temperature for 30 minutes to 2 hours.

As the starting material to be used in the production process of the present invention, any compound of the leucomycin Fr group is suitable. In the above-mentioned heterogenous reaction, the compound having a propionyl group as the acyl side group at the 4"-position (leucomycin AT) can complete the reaction within a shorter period of time and achieve a slightly improved yield, compared with another compound having an isovaleryl group at said position (leucomycin $A_1$). However, any acyl group of natural type binding to the hydroxyl group at the 4"-position can be deacylated by the above-mentioned heterogenous reaction to thereby give the desired compound.

The hydroxyl group at the 4"-position of the mycarose moiety of the compound represented by the formula (IX), wherein $R^8$ is a silyl protective group, can be alkylated selectively or unselectively in the following manner. The compound of the formula (IX) have two free hydroxyl groups and the hydroxyl group at the 3"-position is a tertiary alcohol while the one at the 4"-position is a secondary alcohol. Thus, a reaction for forming ether bonds (Williamson reaction) by introducing alkyl groups can be performed by taking advantage of the difference between the reactivities of these hydroxyl groups. That is to say, the compound represented by the formula (IX) is subjected to the Williamson reaction to thereby introduce an alkyl group selectively into the hydroxyl group at the 4"-position in the mycarose moiety. Thus the compound represented by the formula (X), wherein $R^5$ is an alkyl group and $R^8$ is a silyl protective group, can be obtained in a high yield.

For example, the compound (18) [the compound of the formula (IX) wherein $R^8$ is a TBDMS group] is reacted with an excessive amount of isoamyl iodide in DMF in the presence of sodium hydride under heating. Thus the compound (27) [the compound of the formula (X) wherein $R^5$ is an isoamyl group and $R^8$ is a TBDMS group] is obtained in a high yield. When the alkyl side chain to be introduced is a somewhat bulky one, such as an isoamyl group, the reaction shows a high regio-selectivity. However, said selectivity is deteriorated as the alkyl side chain becomes less bulky. In fact, when the compound (18) or its analogue is reacted with methyl iodide in the presence of sodium hydride, a compound wherein not only the hydroxyl group at the 4"-position but also the tertiary hydroxyl group at the 3"-position have been methylated is formed (refer to Example 32).

In order to draw a proton from a free hydroxyl group to thereby form an alkoxide in the above-mentioned alkylation step, metal hydrides such as potassium hydride are usable, in addition to sodium hydride. As the alkylating agent, alkyl halides such as alkyl bromides are usable, in addition to alkyl iodides. As the alkyl chain, primary alkyl groups and secondary alkyl groups are suitable and primary ones are preferable. The alkylating agent is generally used in an amount of 30 equivalents of the compound to be alkylated. In addition to DMF, THF, dioxane or the like may be used as the reaction solvent. The solvent is used in an amount of 15% (v/w) based on the compound to be alkylated. The alkylation can easily proceed at a temperature of 0° to 100° C., preferably 40° to 50° C., more preferably 45° C. In order to efficiently complete this reaction, it is particularly important to control the reaction temperature. The reaction time ranges from 30 minutes to 1 hour.

An alkyl group can be introduced to the tertiary hydroxyl group at the 3"-position in the mycarose moiety of the compound represented by the formula (X) and the silyl group binding to the hydroxyl group at the 2'-position in the mycaminose moiety can be selectively deprotected in the following manner.

The compound represented by the formula (X) is (1) subjected to the Williamson reaction to thereby introduce an alkyl group into the tertiary hydroxyl group at the 3"-position in the mycarose moiety. Next, (2) an oxygen atom is introduced thereto with the use of an organic peroxide. Finally, (3) a selective desilylation at the 2'-position accompanied by the removal of an oxygen atom is performed to thereby give the compound represented by the formula (XI), wherein $R^4$ and $R^5$ are alkyl groups and $R^8$ is a silyl protective group.

For example, the compound (27) [the compound of the formula (X) wherein $R^5$ is an isoamyl group and $R^8$ is a TBDMS group] is (1) reacted with an excessive amount of ethyl iodide in DMF in the presence of sodium hydride to thereby ethylating the tertiary hydroxyl group at the 3"-position. Next, (2) an oxygen atom is introduced thereto with the use of m-chloroperbenzoic acid. Subsequently, a selective deprotection of a TBDMS group at the 2'-position accompanied by the removal of an oxygen atom is performed by (3)-A reacting with silica gel in the coexistence or absence of an organic solvent or (3)-B through an acid hydrolysis reaction. Thus the compound (29) [the compound of the formula (XI) wherein $R^4$ is an ethyl group, $R^5$ is an isoamyl group and $R^8$ is a TBDMS group] is obtained.

As the Williamson reaction for introducing an alkyl group into a common tertiary hydroxyl group, there has been established, for example, a method via a copper (I) tertiary alkoxide [Journal of American Chemical Society, 96 (9), 2829 (1974)]. In the case of the alkylation (1) of the tertiary hydroxyl group at the 3"-position in the mycarose moiety in the present invention, the reaction substrate is protected and stabilized with three silyl groups. Thus the common Williamson reaction is applicable thereto without particular modification. Therefore, the reaction conditions per se are roughly similar to those employed in the alkylation of the hydroxyl group at the 4"-position in the mycarose moiety of the compound represented by the formula (IX), though it is more important to control the temperature during the reaction within 40° to 50° C., preferably 45° C. It is sometimes observed that the introduction of a bulky alkyl group causes a somewhat decrease in the yield. The alkyl group preferably has 1 to 4 carbon atoms.

It is not always the most preferable to perform this process involving a 3-step chemical reaction for synthesizing the compound represented by the formula (XI) from the compound represented by the formula (X) [(1) 3"-O-alkylation, (2) addition of an oxygen atom and (3) selective desilylation at the 2'-position accompanied by the removal of an oxygen atom] in this order, depending on the types of the alkylating reagent and the silyl protective group. Namely, it is useful for completing said process that an oxygen atom is added (2) and then the 3"-O-alkylation is carried out (1), followed by effecting the treatment (3). In fact, the addition of an oxygen atom (2) was followed by the 3"-O-methylation (1) in, for instance, Examples 16 and 19. That is to say, the addition of an oxygen atom with the use of an organic peroxide is not always necessary in the alkylation of the tertiary hydroxyl group at the 3"-position but exerts its effect in the selective deprotection of the silyl group, as described hereinafter.

Namely, in a 16-membered macrolide derivative having two hydroxyl groups in the mycarose moiety both forming ether bonds with alkyl groups, it is highly difficult to completely deprotect three silyl groups (for example, TBDMS groups) introduced respectively into the hemiacetal hydroxyl group formed at the 3,18-position and hydroxyl groups at the 9- and 2'-positions without affecting other parts of the substrate by known deprotection methods [Theodora W. Greene; Peter G. M. Wuts, *Protective Groups in Organic Synthesis,* 2nd ed., Wiley: New York, 1991]. In a derivative prepared by adding an oxygen atom (2) to said silyl-protected derivative, however, the selective desilylation at the 2'-position accompanied by the removal of one oxygen atom (3), for example, the selective deprotection of the TBDMS group at the 2'-position, efficiently proceeds and then other two silyl groups can be completely deprotected.

It is considered that the organic peroxide would add an oxygen atom (2) in the vicinity of the mycaminose moiety. The compound having an oxygen atom added thereto is somewhat unstable, in particular, under acidic conditions. Thus the chemical structure of such a compound having an oxygen atom added thereto has never been clarified so far. On the other hand, examples of the peroxide giving said oxygen atom include organic peroxides such as m-chloroperbenzoic acid, perbenzoic acid and peracetic acid and hydrogen peroxide. It is preferable to use m-chloroperbenzoic acid therefor. The organic peroxide is used in an amount of 1.0 to 1.1 equivalents of the silyl-protected derivative. The reaction solvent may be selected from, for example, chloroform, methylene chloride, ether and t-butanol. The solvent is used in an amount of 5 to 200% (v/w), preferably 50% (v/w), based on the silyl-protected derivative. The reaction can be completed within a short period of time at a temperature of from -10° C. to room temperature or above.

The silyl group at the 2'-position of a 16-membered macrolide compound, which is protected with three silyl groups, has two hydroxyl groups both forming ether bonds with alkyl groups in the mycarose moiety and further has an oxygen atom added thereto, can be selectively deprotected accompanied by the removal of an oxygen atom [i.e., the above-mentioned step (3)] in the following manner. This reaction quantitatively proceeds by allowing the reactants to stand in the presence of silica gel [(3)-A]. The reaction system for the reaction with silica gel may either or not contain an organic solvent. This reaction can be performed either by the batch method or by the column method. To produce a small amount of a compound, TLC is also useful.

The batch method is carried out as follows. The reaction substrate is dissolved in an organic solvent and silica gel is added thereto in such a manner as to give a homogeneous mixture. When allowed to stand at room temperature in the coexistence of the organic solvent or removing the organic solvent by, for example, concentrating under reduced pressure and allowing to stand in the absence of any organic solvent, the desired selective deprotection of the silyl group at the 2'-position accompanied by the removal of an oxygen atom efficiently proceeds.

The column method can be carried out as follows. A high concentration solution of the reaction substrate ranging from 2 to 10% (v/w) is placed on the top of a silica gel column packed by the wet-system and then allowed to stand at room temperature. Thus the desired reaction efficiently proceeds. After allowing to stand, the silica gel column is successively developed using, for example, chloroform/methanol (50:1). Thus the compound represented by the formula (XI) can be obtained in a high yield. The organic solvent to be used in this reaction is not particularly restricted but arbitrarily selected from among, for example, chloroform, methylene chloride, acetonitrile, methanol and mixtures thereof. Any silica gel commonly used, for example, Wakogel C-200, C-300; Merck Kieselgel Art. 15101, Art. 9385, may be used.

The TLC method is suitable for the production of a small amount of a compound. The reaction substrate is dissolved in a small amount of an organic solvent and then charged on a TLC plate. After allowing to stand at room temperature, the plate is developed in a conventional manner using, for example, chloroform/methanol (20:1). Thus the compound represented by the formula (XI) can be obtained in a high yield.

The selection of either of the batch method, the column method and the TLC method and the length of the standing time are determined depending on the structure of the reaction substrate and the reaction scale. When allowed to stand at room temperature, several hours to several days are usually required for the completion of the reaction.

To perform this reaction via acid hydrolysis [(3)-B], a mixture of a dilute aqueous solution of an organic acid or an inorganic acid with an organic solvent being uniformly miscible with water may be used. Compared with the above-mentioned method A, this method is advantageous in requiring no silica gel. Usable as the aqueous solution of an acid is an aqueous solution of hydrochloric acid of 0.001 to 0.5N, preferably 0.01 to 0.05N may be cited. In addition to the hydrochloric acid, sulfuric acid, phosphoric acid, methanesulfonic acid and trifluoroacetic acid are also usable. Examples of the organic solvent include methanol, ethanol, acetonitrile, THF and dioxane with methanol and acetonitrile being preferred. The mixing ratio of the dilute aqueous solution of an acid and the organic solvent may be arbitrarily determined, so long as the reaction substrate is soluble therein. Usually, a mixing ratio of about 1:1 is employed. The reaction temperature and the reaction time widely vary depending on the type and concentration of the employed acid. In general, the reaction is carried out at 0 to 60° C., preferably 40° to 50° C. for several minutes to several hours, preferably 1 to 4 hours (refer to Example 26).

Another advantage of the selection of the hydrolysis method (3)-B resides in that when the reaction is further continued, two silyl groups other than the one at the 2'-position (for example, TBDMS groups) are successively deprotected and thus the desired final product represented by the formula (III), wherein $R^4$ and $R^5$ are alkyl groups, can be obtained. For example, when a compound prepared by methylating the tertiary hydroxyl group at the 3"-position of the compound (27) [the compound of the formula (X) wherein $R^5$ is an isoamyl group and $R^8$ is a TBDMS group] and adding an oxygen atom thereto is hydrolyzed with a mixture of 0,025 N hydrochloric acid and acetonitrile (1:1) at 45° C. for 4 hours, the compound (12) [the compound represented by the formula (III) wherein $R^4$ is a methyl group and $R^5$ is an isoamyl group] can be obtained in a high yield (refer to Example 34). Besides the compound (12), a trace amount of a separable allylic rearrangement product of the compound (12) [Chemical and Pharmaceutical Bulletin, 18 (8), 1501 (1970); Scientific Reports of Meiji Seika Kaisha, 12, 85 (1972); and Journal of Antibiotics, 35 (11), 1521 (1982)] is formed by this reaction. However, the number of reaction steps is lowered and the amount of the reaction reagents is reduced in this reaction, compared with the production method via the compound of the formula (XI) shown in the Reaction Scheme I in the present invention, which largely contributes to the reduction of the production cost. Although a longer reaction time is required for the final deprotection of three silyl groups such as TBDMS groups than the selective desilylation at the 2'-position, the reaction conditions per se are similar to those employed in the acid hydrolysis [(3)-B].

The two silyl groups binding to the hemiacetal hydroxyl group formed at the 3,18-position and the hydroxyl group at the 9-position can be deprotected in the following manner. These silyl groups such as TBDMS groups can be completely or incompletely deprotected by, for example, reacting with tetra-n-butylammonium fluoride (TBAF) reagent or a certain acid, such as hydrochloric acid, or treating under known conditions for deprotecting silyl ether binding to hydroxyl group [Theodora W. Greene; Peter G. M. Wuts, *Protective Groups in Organic Synthesis*, 2nd ed., Wiley: New York, 1991]. In the case of using TBAF as the desilylating agent, the compound represented by the formula (XI) which is used as a reaction substrate is efficiently deprotected. When the compound represented by the formula (XI) wherein $R^8$ is a TBDMS group is deprotected using TBAF, it is converted into the final product of the formula (III). For example, the compound (29) [the compound of the formula (XI) wherein $R^4$ is an ethyl group, $R^5$ is an isoamyl group and $R^8$ is a TBDMS group] is reacted with an excessive amount of TBAF in THF under heating. Thus the compound (14) [the compound of the formula (III) wherein $R^4$ is an ethyl group and $R^5$ is an isoamyl group] is obtained as the major product.

In the deprotection of two silyl groups such as TBDMS groups using TBAF, the completion of the reaction can be promoted and side reactions can be completely inhibited by preventing the reaction system from the invasion of water. Since TBAF acts on free aldehyde groups as a strong base, care should be fully paid to the working-up after the completion of the reaction in order to efficiently perform this deprotection step, as described in detail in Examples. As the reaction solvent in this deprotection with the use of TBAF, ether solvents, halogen solvents and nitrile solvents are usable. THF is preferably used. To complete this reaction, the concentration of TBAF per se in the reaction solvent serves as an important factor. When the equivalence of TBAF to the reaction substrate remains constant, the reaction can be hardly completed at an excessively low concentration of TBAF in the reaction solvent (i.e., too much reaction solvent) or at an excessively high concentration thereof (i.e., too little reaction solvent). In usual, the reaction efficiently proceeds at a concentration of from 0.5 to 4M, preferably from 1 to 2M. TBAF is used in an amount of from 2 equivalents to in excess. The deprotection can completely and quickly proceed by using TBAF of 10 equivalents or more. The reaction can be carried out at 40° to 50° C., preferably 45° C., for 30 minutes to 2 hours, preferable 1 hour.

On the basis of the present invention, novel and useful substances can be created by a known method for selectively acylating the hydroxyl group at the 9- or 2'-position of the compound represented by the formula (III) or its salt [Hakko to Kogyo, 37 (12), 1171 (1979)]; by a known method for the allylic rearrangement of the hydroxyl group at the 9-position to the 11- or 13-position in the presence of a dilute acid [Chemical and Pharmaceutical Bulletin , 18 (8), 1501 (1970); Scientific Reports of Meiji Seika Kaisha, 12, 85 (1972); and Journal of Antibiotics, 35 (11), 1521 (1982)]; or by a known method for selectively oxidizing the hydroxyl group at the 9-position [Journal of Antibiotics, 24 (8), 526 (1971)]. For example, the hydroxyl group at the 9-position of the compound (12) [the compound of the formula (III) wherein $R^4$ is a methyl group and $R^5$ is an isoamyl group] is selectively acetylated by a known method (JP-A-48-13380) to thereby give the compound (13). Further, the compound represented by the formula (III) or its salt can be converted into the compound represented by the formula (V) or its salt through an appropriate biochemical reaction (for example, microbial conversion). For example, the compound (12) is subjected to microbial conversion using SF2772 strain which is capable of 3-O-acylation to thereby give the compound (3) (refer to Example 35).

As described above, it is important in the production process of the present invention to perform a chemical reaction for adding an oxygen atom by an organic peroxide (for example, m-chloroperbenzoic acid) for the deprotection of the silyl group (for example, TBDMS group) binding to the hydroxyl group at the 2'-position in the mycaminose moiety. This reaction for adding an oxygen atom can be carried out prior to the alkylation of the tertiary hydroxyl group at the 3"-position in the mycarose moiety. This reaction for adding an oxygen atom may be also carried out prior to the alkylation of the secondary hydroxyl group at the 4"-position in the mycarose moiety (refer to Example 32) or, furthermore, prior to the removal of the acyl group binding to the hydroxyl group at the 4"-position by the heterogenous reaction. Thus the compound represented by the formula (III) can be produced. However, this reaction is preferably performed immediately before or immediately after the alkylation of the tertiary hydroxyl group at the 3"-position in the mycarose moiety from the viewpoint of the improvement in the total yield. In the Reaction Scheme I, the compound represented by the formula (IX) is synthesized starting from a compound of the leucomycin Fr group via two steps. The compound represented by the formula (IX) can be synthesized starting from leucomycin V [Journal of Antibiotics, 28 (6), 401 (1975)] via selective trisilylation of a single step.

According to the above-described process, the compound represented by the formula (III), which is an important intermediate in the synthesis of the novel 16-membered macrolide derivative represented by the formula (VII) and is a novel 16-membered macrolide derivative per se highly useful as an antimicrobial agent can be efficiently prepared from a known naturally occurring 16-membered macrolide antibiotics represented by the formula (II) via only five or six steps. When the compound (12) is prepared from midecamycin $A_3$ and erythromycin, a chemical reaction consisting of eight steps and a microbial conversion of two steps were performed and the total yield from midecamycin $A_3$ was lower than 1%. In contrast, the process of the present invention makes it possible to synthesize the compound (12) starting from, for example, leucomycin $A_7$ at a total yield of around 10%.

There has been known neither natural nor synthetic compound wherein an alkyl group other than a methyl group has been introduced into the tertiary hydroxyl group at the 3"-position in the mycarose moiety, as in the case of the compounds (14) and (15). Therefore, valuable information for clarifying the correlation between the structures and activities of 16-membered macrolide derivatives and the correlation between the structures and pharmaceutical dynamics thereof can be obtained by providing these novel compounds and biochemically evaluating them.

Further, the process of the present invention makes it possible to chemically modify 16-membered macrolide compounds under severe conditions, compared with relatively mild conditions conventionally employed for chemical modification thereof. Thus, the process of the present invention provides not only the methodology whereby alkyl groups are introduced respectively into two hydroxyl groups in the mycarose moiety but also another methodology whereby the neutral sugar moiety can be chemically modified fundamentally under severe conditions compared with those employed in, for example, acylation. Accordingly, by using this novel production process, novel 16-membered macrolide derivatives having a completely new structure, wherein hydroxyl group(s) in the mycarose moiety are modified, can be created.

The compounds of the present invention may be in the form of a pharmaceutically acceptable inorganic or organic salt. Examples of the salts include a salt of inorganic acid such as hydrochloric acid, sulfuric acid, nitric acid, phosphoric acid and a salt of organic acid such as acetic acid, stearic acid, malic acid and succinic acid.

Antimicrobial activities of the compounds of the present invention were determined by measuring minimum inhibitory concentration (MIC). Minimum inhibitory concentration was determined by the agar plate dilution method in the following manner.

Test strains were subjected to seed culture using Sensitivity test broth (STB, Nissui Pharmaceutical) except that the strains belonging to the genus Streptococcus, Branhamella and Haemophilus were cultured on blood agar plate. A 5 μl portion of cell suspension of the test strains having about $10^6$ CFU/ml was inoculated into Sensitivity disk agar (SDA, Nissui Pharmaceutical) supplemented with 5% horse blood and incubated at 37° C. for 20 hours. Then, MIC was measured. For comparison, MDM and leucomycin $A_7$ (LM-$A_7$) was also tested. The results are shown in Tables 1, 2 and 3.

TABLE 1

| Test strain | Antimicrobial activity (MIC: μg/ml) | | | |
|---|---|---|---|---|
| | Compound (2) | Compound (3) | Compound (5) | MDM |
| S. aureus 209P JC-1 | 0.39 | 0.20 | 0.39 | 0.39 |
| S. aureus M133 | 0.78 | 0.78 | 1.56 | 0.78 |
| S. aureus M126 | >100 | >100 | >100 | >100 |
| S. aureus MS15009/pMS99 | >100 | >100 | >100 | >100 |
| S. aureus MS15026 | >100 | >100 | >100 | >100 |
| S. aureus MS15009/pMS98 | 0.39 | 0.78 | 0.78 | 0.39 |
| S. aureus MS15027 | 0.78 | 0.78 | 1.56 | 0.78 |
| S. epidermidis ATCC14990 | 1.56 | 1.56 | 1.56 | 1.56 |
| M. luteus ATCC9341 | 0.05 | 0.05 | 0.10 | 0.05 |
| E. faecalis W-73 | 3.13 | 3.13 | 3.13 | 3.13 |
| E. coli NIHJ JC-2 | >100 | >100 | >100 | >100 |
| K. pneumoniae PC1602 | >100 | >100 | >100 | >100 |
| S. pneumoniae IP692 | 0.05 | 0.10 | 0.20 | 0.39 |
| S. Pneumoniae Type 1 | 0.20 | 0.20 | 0.20 | 0.39 |
| S. Pyogenes Cook | 0.20 | 0.10 | 0.20 | 0.20 |
| B. catarrhalis W-0500 | 1.56 | 0.78 | 1.56 | 3.13 |
| B. catarrhalis W-0506 | 1.56 | 1.56 | 1.56 | 1.56 |
| H. influenzae 9334 | 6.25 | 6.25 | 6.25 | 3.13 |
| M. pneumoniae FH | 1.56 | 1.56 | 1.56 | 1.56 |
| M. pneumoniae Mac | 0.10 | 0.05 | 0.20 | 0.10 |
| M. pneumoniae FH-P24 | 0.10 | 0.025 | 0.20 | 0.10 |

TABLE 1-continued

| Test strain | Antimicrobial activity (MIC: μg/ml) | | | |
|---|---|---|---|---|
| | Compound (2) | Compound (3) | Compound (5) | MDM |
| M. pneumoniae Numata | 0.05 | 0.025 | 0.05 | 0.05 |

TABLE 2

| Test strain | Antimicrobial activity (MIC: μg/ml) | | | |
|---|---|---|---|---|
| | Compound (9) | Compound (10) | Compound (11) | Compound (12) |
| S. aureus 209P JC-1 | 0.20 | 0.10 | 0.10 | 0.10 |
| S. aureus M133 | 0.39 | 0.39 | 0.39 | 0.39 |
| S. aureus M126 | >100 | >100 | >100 | >100 |
| S. aureus MS15009/pMS99 | >100 | >100 | >100 | >100 |
| S. aureus MS15026 | >100 | >100 | >100 | >100 |
| S. aureus MS15009/pMS98 | 0.39 | 0.39 | 0.39 | 0.20 |
| S. aureus MS15027 | 0.39 | 0.39 | 0.39 | 0.39 |
| S. epidermidis ATCC14990 | 0.39 | 0.39 | 0.39 | 0.39 |
| M. luteus ATCC9341 | 0.05 | 0.05 | 0.05 | 0.05 |
| E. faecalis W-73 | 0.78 | 0.78 | 0.39 | 0.39 |
| E. coli NIHJ JC-2 | >100 | >100 | >100 | >100 |
| K. pneumoniae PC1602 | >100 | >100 | >100 | >100 |
| S. pneumoniae IP692 | 0.20 | 0.10 | 0.05 | 0.10 |
| S. Pneumoniae Type 1 | 0.20 | 0.20 | 0.20 | 0.10 |
| S. Pyogenes Cook | 0.10 | 0.10 | 0.10 | 0.05 |
| B. catarrhalis W-0500 | 1.56 | 0.78 | 0.39 | 0.39 |
| B. catarrhalis W-0506 | 3.13 | 1.56 | 0.78 | 0.39 |
| H. influenzae 9334 | 6.25 | 3.13 | 3.13 | 1.56 |
| H. influenzae Type b | 12.5 | 12.5 | 12.5 | 6.25 |

TABLE 3

| Test strain | Antimicrobial activity (MIC: μg/ml) | | | |
|---|---|---|---|---|
| | Compound (14) | Compound (15) | Compound (16) | LM-$A_7$ |
| S. aureus 209P JC-1 | 0.20 | 0.20 | 0.10 | 0.20 |
| S. aureus M133 | 0.78 | 0.78 | 0.39 | 0.39 |
| S. aureus M126 | >100 | >100 | >100 | >100 |
| S. aureus MS15009/pMS99 | >100 | >100 | >100 | >100 |
| S. aureus MS15026 | >100 | >100 | >100 | >100 |
| S. aureus MS15009/pMS98 | 0.39 | 0.39 | 0.20 | 0.39 |
| S. aureus MS15027 | 0.39 | 0.39 | 0.20 | 0.39 |
| S. epidermidis ATCC14990 | 0.78 | 0.78 | 0.20 | 0.39 |
| M. luteus ATCC9341 | 0.05 | 0.10 | 0.05 | 0.05 |
| E. faecalis W-73 | 0.78 | 0.78 | 0.39 | 0.78 |
| E. coli NIHJ JC-2 | >100 | >100 | >100 | >100 |
| K. pneumoniae PC1602 | >100 | >100 | >100 | >100 |
| S. pneumoniae IP692 | 0.20 | 0.20 | 0.10 | 0.20 |
| S. Pneumoniae Type 1 | 0.20 | 0.20 | 0.20 | 0.20 |
| S. Pyogenes Cook | 0.10 | 0.10 | 0.10 | 0.10 |
| B. catarrhalis W-0500 | 0.39 | 0.78 | 0.78 | 0.78 |
| B. catarrhalis W-0506 | 0.78 | 0.78 | 0.78 | 1.56 |
| H. influenzae 9334 | 6.25 | 6.25 | 3.13 | 0.78 |
| H. influenzae Type b | 12.5 | 50 | 6.25 | 6.25 |

As Table 1 shows, the compounds (2), (3) and (5) represented by the formula (V) have strong antimicrobial activities on Gram-positive bacteria and Mycoplasma which are clinically important. In particular, the compounds (2) and (3) show excellent antimicrobial activities comparable to, or even exceeding, that of MDM. Further, the compound (3) has a practically effective anti-Mycoplasma activity. Also, the compound (4) has an antimicrobial activity almost comparable to that of the compound (3) (data are not shown).

As shown in Tables 2 and 3, the compounds (9), (10), (11), (12), (14), (15) and (16) represented by the formula (III) each shows a strong antimicrobial activity on Gram-positive bacteria which are clinically important. The compounds (10), (11), (12) and C16) are clearly much superior to MOM (data are not shown) in the antimicrobial activity in vitro and, as shown in Tables 2 and 3, comparable or superior in the antimicrobial activity to LM-AT, which is one of natural 16-membered macrolide leucomycins with strong antimicrobial activity, except on *Haemophilus influenzae*. Also, the compound (13) is comparable in the antimicrobial activity to the compound (12) (data are not shown).

Further, the compounds (2), (3) and (5) represented by the formula (V) are characterized by being extremely long-acting in rat plasma. This high stability relates directly to the fact that each of the hydroxyl groups in the mycarose moiety of the compound obtained in the present invention forms not an ester bond with an acyl group but an ether bond with an alkyl group.

The sustained antimicrobial activities on *M. luteus* of the compounds (2), (3) and (5) and MOM were determined in the following manner.

Each test compound and 50 $\mu$l of a methanol solution (10,000 $\gamma$) were added to 950 $\mu$l of thawed rat plasma and the resulting mixture was incubated at 37° C. for 24 hours. After completion of the incubation, a 20 $\mu$l portion of the mixture was added to 980 $\mu$l of 0.05M phosphate buffer (pH 7.6). A 20 $\mu$l portion of the sample solution was used to measure antimicrobial activity against *M. luteus*. Separately, the calibration curve was prepared by using a methanol solution containing each test compound. The starting activity of each compound in the plasma was referred to as 100%. The results are shown in FIG. 1.

The compounds (2), (3) and (5), each having two ether bonds in the mycarose moiety, a hydroxyl group at the 9-position and an acylated hydroxyl group at the 3-position of the lactone ring, are hardly metabolized and thus give no free hydroxyl group in the neutral sugar moiety. As a result, the degree of loss of the antimicrobial activity in the plasma of these compounds is lower than that of MOM. This fact affects the excellent pharmacokinetics of the compounds of the present invention which is shown below. It has been reported that the metabolic pattern of the mycarose moiety of MOM in human is almost the same as that in rat [Yakugaku Zasshi, 102 (8), 781 (1982)]. Accordingly, it is easily estimated that the compounds represented by the formula (V) according to the present invention would exhibit strong and long-acting antimicrobial activities in human blood.

A pharmacokinetics test on the compound (3) of the present invention was carried out by using mice as follows.

The compound (3) was mixed with a 0.2% solution of carboxymethylcellulose to give a concentration of 4 mg/ml and a 1 ml portion of the resulting emulsion was orally administered to 4-week-old male Jcl:ICR mice. Blood was collected from armpit of the mice 30, 60, 120, 240 and 360 minutes after the administration of the test compound (n=2). The collected blood was allowed to stand at room temperature for about 2 hours and centrifuged for 20 minutes with a centrifuge (KUBOTA KS-5000P) to obtain serum. To the serum was added an equivalent volume of 50% CH$_3$CN-50 mM phosphate (1:1 by volume) buffer (pH 7.0). The resulting mixture served as a serum sample. The concentration of the test compound in the serum sample was measured by the following bioassay method.

One hundred 1 $\mu$l of the serum sample was poured into a hole made on a test plate containing 40 ml of MRAPJ medium (6 g/l peptone, 3 g/l yeast extract, 1.5 g/l meat extract, 1 g/l glucose and 15 g/l agar, pH 6.5) supplemented with a solution of *M. luteus* ATCC9341 (1%) and incubated at 32° C. for 18 hours and MIC was measured based on the calibration curve. MOM, MDM and RKM were also tested for comparison. As a result, the maximum concentration of the compound (3) in the serum is 11.3 $\mu$g/ml which completely exceeds those of MOM (6.2 $\mu$g/ml), MDM (5.2 $\mu$g/ml) and RKM (2.9 $\mu$g/ml) and is comparable to that of clarythromycin (CAM) which is a typical new macrolide. This maximum concentration in the mouse serum achieved by the compound (3) is considered the highest one among 16-membered macrolide compounds having a free hydroxyl group at the 9-position. Thus a long-pending problem of "low concentration in serum" of 16-membered macrolide antibiotics has been solved. When the compound (4), i.e., the compound wherein the hydroxyl group at the 9-position of the compound (3) is acetylated is subjected to the same animal test, the maximum concentration in the serum (about 2 hours after the administration) exceeds even that of the compound (3) and a high concentration in the serum (more than 80 % of the maximum level) is sustained 6 hours after the administration. Thus this compound is considered as a macrolide derivative showing new pharmacokinetics.

Subsequently, 200 mg/kg of the compound (3) was orally administered to three mice in the same manner as described above.

The three mice were put in a metabolic cage MM type (Sugiyamagen Company, Tokyo, Japan) and urine was collected 4 and 24 hours after the administration of the test compound. The collected urine was filtered through a filter having a pore size of 0.45 $\mu$m (Millipore) and was mixed with an equivalent volume of 50% CH$_3$CN-50 mM phosphate (1:1 by volume) buffer (pH 6.5) to serve as a urine sample. The bioassay was carried out in the same manner as described above to determine the concentration of the test compound in the urine sample. The recovering in the urine was calculated according to the following equation.

$$\text{Recovery in urine (\%)} = \frac{\text{Conc. of test compound (}\mu\text{g/ml)} \times \text{Urine volume (ml)}}{\text{Dose of test compound (}\mu\text{g)} \times \text{Number of mice}} \times 100$$

As a result, the compound (3) shows a remarkably high recovery in the urine (20 %) compared with other 16-membered macrolide derivatives, MOM, MDM and RKM each showing a recovery in urine of lower than 2%, though it is slightly lower than that of CAM. It is shown that the compound (3) is highly stable (sustaining the antimicrobial activity) in the living mouse body.

As discussed above, the compound (3) of the present invention shows not only a long-acting antimicrobial activity in rat plasma but also excellent pharmacokinetics in the animal experiments with the use of mice. Further, the compound (4) also sustains a high concentration in the serum in the animal experiment with the use of mice. These results are considered to largely depend on the following three structural characteristics, namely, (1) the side chain in the mycarose moiety is not an acyl group but an alkyl group; (2) not a carbonyl group but a hydroxyl group (or an acylated hydroxyl group) is located at the 9-position of the lactone ring; and (3) an acyl group is bound to the hydroxyl group at the 3-position of the lactone ring. It is easily assumed that other analogues including the compound (2) also show highly excellent pharmacokinetics similar to the compound (3).

Further, a pharmacokinetics test on the compound (12) of the present invention is carried out in the same manner as described above. Namely, 200 mg/kg of the compound (12) is orally administered to mice and the concentration of this compound in the serum is determined by a bioassay method with the use of *M. luteus* as a test strain. As a result, the maximum concentration of the compound (12) in the serum is 11.5 $\mu$g/ml which is comparable to that of CAM. The disadvantage of 16-membered ring macrolide antibiotics, which has been pointed out for a long time, has been thus overcome.

The novel 16-membered macrolide derivatives having free hydroxyl groups at the 3- and 9-positions of a lactone ring and two hydroxyl groups in the mycarose moiety each forming ether bonds with alkyl groups possess a very strong antimicrobial activity in vitro and show in a high concentration in mouse serum.

The 16-membered macrolide derivatives may be formulated into antimicrobial pharmaceutical compositions together with known pharmaceutically acceptable carriers.

The following Examples are provided to illustrate the process for producing the compounds of the present invention and physicochemical properties of the compounds of the present invention. The Examples describe the usefulness of a method for the reduction at the 9-position of 16-membered macrolide compounds with the use of Actinomycetes belonging to the genus Streptomyces and the usefulness of a method for the removal of an acyl group binding to the hydroxyl group at the 3-position of 16-membered macrolide compounds with the use of a fungus belonging to the genus Phialophora. Based on these methods, various processes for producing the above-mentioned compounds by using similar biochemical techniques can be devised. On the other hand, based on the processes for producing these compounds by synthetic chemical techniques, various processes for producing the above-mentioned compounds by using similar synthetic chemical techniques can be devised. Therefore, the present invention is not restricted to the following Examples but involves not only the modification of the techniques employed in the Examples but also all methods for synthesizing, producing, extracting and purifying the compounds represented by the formula (I) by using known techniques on the basis of the properties of the compounds (I) clarified by the present invention.

EXAMPLE 1

Process for producing compound (1) [a compound represented by the formula (I) wherein $R^1$ represents a propionyl group, $R^2$ represents a hydrogen atom, $R^3$ represents a hydrogen atom, $R^4$ represents a methyl group and $R^5$ represents an allyl group]:

A medium comprising 2.0% of glucose, 1.0% of polypeptone, 0.05% of dipotassium hydrogenphosphate, 0.05% of magnesium sulfate heptahydrate and 0.3% of sodium chloride was adjusted to pH 7.0 and sterilized prior to the use.

The above-mentioned medium was pipetted in 80 ml portions into three 500 ml-Erlenmeyer's flasks and sterilized at 120° C. for 30 minutes. The medium in each flask was inoculated with 1.6 ml of a-frozen seed of *Streptomyces mycarofaciens* SF2772 strain FERM BP-4465 having a cell density of 10 to 15% which was then incubated therein at 28° C. for 24 hours under shaking. Next, 1.2 ml of a methanol solution containing 20 mg of a compound represented by the formula (VI), wherein $R^4$ represents a methyl group, $R^5$ represents an allyl group and $R^6$ represents an ethyl group, was added to each flask in 0.4 ml portions and the incubation was continued at 28° C. for 17 hours under shaking. After the completion of the incubation, the culture was centrifuged at 3000 rpm for 10 minutes. Thus 180 ml of a transparent culture supernatant was obtained while the solid matters including the cells were removed. To the solid matters was added 120 ml of water and the mixture was stirred followed by centrifugation. The washing liquor thus obtained was combined with the above-mentioned transparent culture supernatant. After adjusting the mixture to pH 9 with a 1N aqueous solution of sodium hydroxide, the conversion product was extracted with 300 ml portions of ethyl acetate twice. The ethyl acetate layer was dried over anhydrous sodium sulfate and then filtered. The filtrate was concentrated under reduced pressure and the residue thus obtained was purified by preparative TLC [developing system: chloroform/ methanol (10:1)]. Thus 9.8 mg of a crude compound (1) was obtained. This crude product was purified by Sephadex LH-20 column chromatography (bed volume: 20 ml, methanol) to thereby give 6.4 mg of the compound (1).

Physicochemical properties 0f the compound (1)
(1) Color and appearance: colorless solid.
(2) Molecular formula: $C_{42}H_{69}NO_{14}$.
(3) Mass spectrum (EIMS): m/z 811 (M)$^+$.
(4) Specific rotation: $[\alpha]_D^{26}$ $-55°$ (c 0.6, $CH_3OH$).
(5) m.p.: 101°–106° C.
(6) $^1H$ NMR spectrum (400 MHz, $CDCl_3$) $\delta$(ppm): 2.24 (br d, 2-H), 2.76 (dd, 2-H), 5.13 (br d, 3-H), 3.26 (br d, 4-H), 3.57 (s, 4-$OCH_3$), 3.87 (br d, 5-H), 1.89 (m, 8-H), 4.07 (dd, 9-H), 5.62 (dd, 10-H), 6.68 (dd, 11-H), 6.08 (br dd, 12-H), 5.79 (ddd, 13-H), 5.03 (ddq, 15-H), 1.26 (d, 16-$H_3$), 2.84 (br dd, 17-H), 9,63 (s, 18-H), 0.99 (d, 19-$H_3$), 2.51 (dq, 3-$OCOCH_2H_3$), 2.64 (dq, 3-$OCOCH_2CH_3$ ), 1.22 (t, 3-$OCOCH_2CH_3$), 4.54 (d, 1'-H), 3.50 (t, 4'-H), 3.28 (dq, 5'-H), 1.16 ($\bar{d}$, 6'-$H_3$), 2.65 (s, 3'-$N(CH_3)_2$), 4.91 (d, 1"-H), 1.57 (dd, 2"-Hax), 2.24 (d, 2"-Heq), 1.24 (s, 3"-$CH_3$), 2.87 (d, 4"-H), 4.40 (dq, 5"-H), 1.23 (d, 6"-$H_3$), 3.25 (s, 3"-$OCH_3$), 4.11 (br dd, 4"-$OCH_2CH=CH_2$), 4.19 (br dd, 4"-$OCH_2CH=CH_2$), 5.95 (ddt, 4"-$OCH_2CH=CH_2$), 5.17 (br d, 4"-$OCH_2CH=CH_2$), 5.23 (br d, 4"-$OCH_2CH=CH_2$).

EXAMPLE 2

Process for producing compound (2) [a compound represented by the formula (I) wherein $R^1$ represents a propionyl group, $R^2$ represents a hydrogen atom, $R^3$ represents a hydrogen atom, $R^4$ represents a methyl group and $R^5$ represents an n-butyl group]:

The same medium as described in Example 1 was pipetted in 80 ml portions into three 500 ml-Erlenmeyer's flasks and sterilized at 120° C. for 30 minutes. The medium in each flask was inoculated with 1.6 ml of a frozen seed of *Streptomyces mycarofaciens* SF2772 strain having a cell density of 10 to 15% which was then incubated therein at 28° C. for 24 hours under shaking. Next, 1.2 ml of a methanol solution containing 20 mg of a compound represented by the formula (VI), wherein $R^4$ represents a methyl group, $R^5$ represents an n-butyl group and $R^6$ represents an ethyl group, was added to each flask in 0.4 ml portions and the incubation was continued at 28° C. for 20 hours under shaking. After the completion of the incubation, the culture was centrifuged at 3000 rpm for 10 minutes. Thus 200 ml of a transparent culture supernatant was obtained while the solid matters including the cells were removed. To the solid matters was added 180 ml of water and the mixture was stirred followed by centrifugation. The washing liquor thus obtained was combined with the above-mentioned transparent culture supernatant. After adjusting the mixture to pH 9 with a 1N aqueous solution of sodium hydroxide, the conversion product was extracted with 380 ml portions of ethyl acetate twice. The ethyl acetate layer was dried over anhydrous sodium sulfate and then filtered. The filtrate was concentrated under reduced pressure and the residue thus obtained was purified by preparative TLC [developing system: chloroform/methanol (10:1)]. Thus 13.5 mg of a crude compound (2) was obtained. This crude product was purified by Sephadex LH-20 column chromatography (bed volume: 20 ml, methanol) to thereby give 9.2 mg of the compound (2).

Physicochemical properties of the compound (2)
  (1) Color and appearance: colorless solid.
  (2) Molecular formula: $C_{43}H_{73}NO_{14}$.
  (3) Mass spectrum (EIMS): m/z 827 (M)+.
  (4) Specific rotation: $[\alpha]_D^{27}$ −50° (c 0.9, $CH_3OH$).
  (5) m.p.: 99°–101° C.
  (6) $^1H$ NMR spectrum (400 MHz, $CDCl_3$) δ(ppm): 2.24 (br d, 2-H), 2.76 (dd, 2-H), 5.13 (br d, 3-H), 3.25 (br d, 4-H), 3.57 (s, 4-$OCH_3$), 3.87 (br d, 5-H), 1.89 (m, 8-H), 4.07 (dd, 9-H), 5.62 (dd, 10-H), 6.67 (dd, 11-H), 6.08 (br dd, 12-H), 5.79 (ddd, 13-H ), 5.03 (ddq, 15 -H), 1.26 (d, 16-$H_3$), 2.85 (br dd, 17-H), 9.63 (s, 18-H), 0.98 (d, 19-$H_3$), 2.51 (dq, 3-OCOC$\underline{H_2}$CH$_3$), 2.64 (dq, 3-OCOC$\underline{H_2}$C$_3$), 1.21 (t, 3-OCOCH$_2$C$\underline{H_3}$), 4.53 (d, 1′-H), 3.22 (br dd, 2′-H), 3.48 (t, 4′-H), 3.28 (dq, 5′-H), 1.15 (d, 6′-$H_3$), 2.62 (s, 3′-N(CH$_3$)$_2$), 4.89 (d, 1″-H), 1.57 (dd, 2″-Hax), 2.23 (d, 2″-Heq), 1.24 (s, 3″-CH$_3$), 2.78 (d, 4″-H), 4.39 (dq, 5″-H), 1.22 (d, 6″-$H_3$), 3.25 (s, 3″OCH$_3$), 3.57 (dt, 4″-OC$\underline{H_2}$CH$_2$CH$_2$CH$_3$), 3.62 (dt, 4″-OC$\underline{H_2}$CH$_2$C$\underline{H_2}$CH$_3$), 1.60 (m, 4″-OCH$_2$C$\underline{H_2}$CH$_2$CH$_3$), 1.37 (m, 4″-OCH$_2$CH$_2$C$\underline{H_2}$CH$_3$), 0.91 (t, 4″-OCH$_2$CH$_2$CH$_2$C$\underline{H_3}$).

EXAMPLE 3

Process (1 ) for producing compound (3 ) [a compound represented by the formula (I) wherein $R^1$ represents a propionyl group, $R^2$ represents a hydrogen atom $R^3$ represents a hydrogen atom, $R^4$ represents a methyl group and $R^5$ represents an isoamyl group]:

The same medium as described in Example 1 was pipetted in 80 ml portions into three 500 ml-Erlenmeyer's flasks and sterilized at 120° C. for 30 minutes. The medium in each flask was inoculated with 1.6 ml of a frozen seed of *Streptomyces mycarofaciens* SF2772 strain having a cell density of 10 to 15% which was then incubated therein at 28° C. for 24 hours under shaking. Next, 1.2 ml of a methanol solution containing 20 mg of a compound represented by the formula (VI), wherein $R^4$ represents a methyl group, $R^5$ represents an isoamyl group and $R^6$ represents an ethyl group, was added to each flask in 0.4 ml portions and the incubation was continued at 28° C. for 18 hours under shaking. After the completion of the incubation, the culture was centrifuged at 3000 rpm for 10 minutes. Thus 180 ml of a transparent culture supernatant was obtained while the solid matters including the cells were removed. To the solid matters was added 120 ml of water and the mixture was stirred followed by centrifugation. The washing liquor thus obtained was combined with the above-mentioned transparent culture supernatant. After adjusting the mixture to pH 9 with a 1N aqueous solution of sodium hydroxide, the conversion product was extracted with 300 ml portions of ethyl acetate twice. The ethyl acetate layer was dried over anhydrous sodium sulfate and then filtered. The filtrate was concentrated under reduced pressure and the residue thus obtained was purified by preparative TLC [developing system: chloroform/methanol (10:1)]. Thus 9.6 mg of a crude compound (3) was obtained. This crude product was purified by Sephadex LH-20 column chromatography (bed volume: 20 ml, methanol) to thereby give 7.3 mg of the compound (3).

Physicochemical properties of the compound (3)
  (1) Color and appearance: colorless solid.
  (2) Molecular formula: $C_{44}H_{75}NO_{14}$.
  (3) Mass spectrum (EIMS): m/z 841 (M)+.
  (4) Specific rotation: $[\alpha]_D^{26}$ −49° (c 0.7, $CH_3OH$).
  (5) m.p.: 98°–100° C.
  (6) $^1H$ NMR spectrum (400 MHz, $CDCl_3$) δ (ppm): 2.24 (br d, 2-H), 2.76 (dd, 2-H), 5.13 (br d, 3-H), 3.26 (br d, 4-H), 3.57 (s, 4-$OCH_3$), 3.87 (br d, 5-H), 1.89 (m, S-H), 4.07 (dd, 9-H), 5.62 (dd, 10-H), 6.68 (dd, 11-H), 6.08 (br dd, 12-H), 5.79 (ddd, 13-H), 5.03 (ddq, 15-H), 1.26 (d, 16-$H_3$), 2.85 (br dd, 17-H), 9.63 (s, 18-H), 0.99 (d, 19-$H_3$), 2.51 (dq, 3-OCOC$\underline{H_2}$CH$_3$), 2.64 (dq, 3-OCOC$\underline{H_2}$CH$_3$), 1.22 (t, 3-OCOCH$_2$C$\underline{H_3}$), 4.53 (d, 1′-H), 3.22 (br dd, 2′-H), 3.48 (t, 4′-H), 3.28 (dq, 5′-H), 1.15 (d, 6′-$H_3$), 2.62 (s, 3′-N(CH$_3$)$_2$), 4.89 (d, 1″-H), 1.57 (dd, 2″-Hax), 2.22 (d, 2″-Heq), 1.24 (s, 3″-CH$_3$), 2.78 (d, 4″-H), 4.39 (dq, 5″-H), 1.23 (d, 6″-$H_3$), 3.25 (s, 3″-OCH$_3$), 3.60 (dt, 4″-OC$\underline{H_2}$CH$_2$CH(CH$_3$)$_2$), 3.64 (dt, 4″-OC$\underline{H_2}$CH$_2$CH(CH$_3$)$_2$), 1.69 (m, 4″-OCH$_2$C$\underline{H_2}$CH(CH$_3$)$_2$), 0.89 (d, 4″-OCH$_2$CH$_2$C$\underline{H}$(CH$_3$)$_2$).

EXAMPLE 4

Process for producing compound (4) [a compound represented by the formula (I) wherein $R^1$ represents a propionyl group, $R^2$ represents an acetyl group, $R^3$ represents a hydrogen atom, $R^4$ represents a methyl group and $R^5$ represents an isoamyl group]:

To 13.0 mg of the compound (3) was added 0.64 ml of dry toluene to dissolve the compound (3) and 5.6 μl of dry pyridine and 4.8 μl of acetyl chloride were successively added thereto, followed by stirring at room temperature for 45 minutes. Then the reaction mixture was extracted with 3.2 ml of ethyl acetate and 8.0 μl of triethylamine. The ethyl acetate layer was washed with 3.2 ml portions of water twice, dried over anhydrous sodium sulfate and then filtered. The filtrate was concentrated under reduced pressure and the residue thus obtained was purified by preparative TLC [developing system: chloroform/methanol (10:1)]. Thus 10.7 mg of the compound (4) was obtained.

Physicochemical properties of the compound (4)
  (1) Color and appearance: colorless solid.
  (2) Molecular formula: $C_{46}H_{77}NO_{15}$.
  (3) Mass spectrum (SIMS): m/z 884 (M+H)+.
  (4) Specific rotation: $[\alpha]_D^{13}$ −56° (c 1.0, $CH_3OH$).
  (5) m.p.: 104°–108° C.
  (6) $^1H$ NMR spectrum (400 MHz, $CDCl_3$) δ (ppm): 2.25 (br d, 2-H), 2.74 (dd, 2-H), 5.11 (br d, 3-H), 3.24 (br d, 4-H), 3.57 (s, 4-$OCH_3$), 3.93 (br d, 5-H), 2.01 (m, 8-H), 5.08 (dd, 9-H), 2.02 (s, 9-OCOCH$_3$), 5.57 (dd, 10-H), 6.74 (dd, 11-H), 6.09 (br dd, 12-H), 5.88 (ddd, 13-H), 2.17 (dt, 14-H), 4.98 (ddq, 15-H), 1.26 (d, 16-H$_3$), 2.83 (br dd, 17-H), 9.64 (s, 18-H), 0.95 (d, 19-H$_3$), 2.51 (dq, 3-OCOCH$_2$CH$_3$, 2.67 (dq, 3-OCOCH$_2$CH$_3$), 1.21 (t, 3-OCOC$\overline{\text{H}}_2$CH$_3$), 4.51 (d, 1'-H), 3.15 (d̄d, 2'-H), 2.39 (t, 3'-H), 3.46 (t, 4'-H), 3.27 (dq, 5'-H), 1.14 (d, 6'-H$_3$), 2.56 (s, 3'-N(CH$_3$)$_2$), 4.88 (d, 1''-H), 1.56 (dd, 2''-Hax), 2.22 (d, 2''-Heq), 1.24 (s, 3''-CH$_3$), 2.78 (d, 4''-H), 4.42 (dq, 5''-H), 1.23 (d, 6''-H$_3$), 3.25 (s, 3''-OCH$_3$), 3.59 (dt, 4''-OCH$_2$CH$_2$CH(CH$_3$)$_2$), 3.64 (dt, 4''-OC$\overline{\text{H}}_2$CH$_2$CH(CH$_3$)$_2$), 1.51 (m, 4''-OCH̄$_2$CH$_2$CH$_2$CH(CH$_3$)$_2$), 1.69 (m, 4''-OCH$_2$C$\overline{\text{H}}_2$CH$_2$CH(CH$_3$)$_2$), 0.89 (d, 4''-OCH$_2$CH$_2$CH$_2$C$\overline{\text{H}}_3$)$_2$).

EXAMPLE 5

Process for producing compound (5) [a compound represented by the formula (I) wherein R$^1$ represents a propionyl group, R$^2$ represents a hydrogen atom, R$^3$ represents a hydrogen atom, R$^4$ represents a methyl group and R$^5$ represents a hexyl group]:

The same medium as described in Example 1 was pipetted in 80 ml portions into three 500 ml-Erlenmeyer's flasks and sterilized at 120° C. for 30 minutes. The medium in each flask was inoculated with 1.6 ml of a frozen seed of *Streptomyces mycarofaciens* SF2772 strain having a cell density of 10 to 15% which was then incubated therein at 28° C. for 24 hours under shaking. Next, 1.2 ml of a methanol solution containing 20 mg of a compound represented by the formula (VI), wherein R$^4$ represents a methyl group, R$^5$ represents a hexyl group and R$^6$ represents an ethyl group, was added to each flask in 0.4 ml portions and the incubation was continued at 28° C. for 19 hours under shaking. After the completion of the incubation, the culture was centrifuged at 3000 rpm for 10 minutes. Thus 190 ml of a transparent culture supernatant was obtained while the solid matters including the cells were removed. To the solid matters was added 160 ml of water and the mixture was stirred followed by centrifugation. The washing liquor thus obtained was combined with the above-mentioned transparent culture supernatant. After adjusting the mixture to pH 9 with a 1N aqueous solution of sodium hydroxide, the conversion product was extracted with 350 ml portions of ethyl acetate twice. The ethyl acetate layer was dried over anhydrous sodium sulfate and then filtered. The filtrate was concentrated under reduced pressure and the residue thus obtained was purified by preparative TLC [developing system: chloroform/methanol (10:1)]. Thus 12.2 mg of a crude compound (5) was obtained. This crude product was purified by Sephadex LH-20 column chromatography (bed volume: 20 ml, methanol) to thereby give 8.3 mg of the compound (5).

Physicochemical properties of the compound (5)
 (1) Color and appearance: colorless solid.
 (2) Molecular formula: C$_{45}$H$_{77}$NO$_{14}$.
 (3) Mass spectrum (EIMS): m/z 855 (M)$^+$.
 (4) Specific rotation: [α]$_D^{24}$ −50° (c 0.8, CH$_3$OH).
 (5) m.p.: 96°–102° C.
 (6) $^1$H NMR spectrum (400 MHz, CDCl$_3$) δ (ppm): 2.24 (br d, 2-H), 2.76 (dd, 2-H), 5.13 (br d, 3-H), 3.25 (br d, 4-H), 3.57 (s, 4-OCH$_3$, 3.87 (br d, 5-H), 1.89 (m, 8-H), 4.07 (dd, 9-H), 5.62 (dd, 10-H), 6.68 (dd, 11-H), 6.08 (br dd, 12-H), 5.79 (ddd, 13-H), 5.03 (ddq, 15-H), 1.26 (d, 16-H$_3$), 2.85 (br dd, 17-H), 9.63 (s, 18-H), 0.99 (d, 19-H$_3$), 2.51 (dq, 3-OCOCH$_2$CH$_3$), 2.64 (dq, 3-OCOCH$_2$CH$_3$), 1.22 (t, 3-OC$\overline{\text{O}}$CH$_2$CH$_3$), 4.53 (d, 1'-H), 3.22 (br dd, 2'-H), 3.48 (t, 4'-H), 3.28 (d̄q, 5'-H), 1.15 (d, 6'-H$_3$), 2.63 (s, 3'-N(CH$_3$)$_2$), 4.89 (d, 1''-H), 1.57 (dd, 2''-Hax), 2.23 (d, 2''-Heq), 1.24 (s, 3''-CH$_3$), 2.78 (d, 4''-H), 4.39 (dq, 5''-H), 1.23 (d, 6''-H$_3$), 3.25 (s, 3''-OCH$_3$), 3.55 (dt, 4''-OCH$_2$CH$_2$(CH$_2$)$_3$CH$_3$), 3.61 (dt, 4''-OC$\overline{\text{H}}_2$CH$_2$(CH$_2$)$_3$CH$_3$), 1.61 (m, 4''-OCH$_2$)C$\overline{\text{H}}_2$(CH$_2$)$_3$CH$_3$), 0.88 (t, 4''-OCH$_2$C$\overline{\text{H}}_2$(CH$_2$)C$\overline{\text{H}}_3$).

EXAMPLE 6

Process for producing compound (6) [a compound represented by the formula (I) wherein R$^1$ represents a propionyl group, R$^2$ represents a hydrogen atom, R$^3$ represents a hydrogen atom, R$^4$ represents a methyl group and R$^5$ represents a benzyl group]:

The same medium as described in Example 1 was pipetted in 100 ml portions into two 500 ml-Erlenmeyer's flasks and sterilized at 120° C. for 30 minutes. The medium in each flask was inoculated with 2.0 ml of a frozen seed of *Streptomyces mycarofaciens* SF2772 strain having a cell density of 10 to 15% which was then incubated therein at 28° C. for 24 hours under shaking. Next, 1.0 ml of a methanol solution containing 20 mg of a compound represented by the formula (VI), wherein R$^4$ represents a methyl group, R$^5$ represents a benzyl group and R$^6$ represents an ethyl group, was added to each flask in 0.5 ml portions and the incubation was continued at 28° C. for 20 hours under shaking. After the completion of the incubation, the culture was centrifuged at 3000 rpm for 10 minutes. Thus 160 ml of a transparent culture supernatant was obtained while the solid matters including the cells were removed. To the solid matters was added 160 ml of water was and the mixture was stirred followed by centrifugation. The washing liquor thus obtained was combined with the above-mentioned transparent culture supernatant. After adjusting the mixture to pH 9 with a 1N aqueous solution of sodium hydroxide, the conversion product was extracted with 320 ml portions of ethyl acetate twice. The ethyl acetate layer was dried over anhydrous sodium sulfate and then filtered. The filtrate was concentrated under reduced pressure and the residue thus obtained was purified by preparative TLC [developing system: chloroform/methanol/conc. aqueous ammonia (100:10:1)]. Thus 10.8 mg of a crude compound (6) was obtained. This crude product was purified by Sephadex LH-20 column chromatography (bed volume: 20 ml, methanol) to thereby give 7.9 mg of the compound (6).

Physicochemical properties of the compound (6)
 (1) Color and appearance: colorless solid.
 (2) Molecular formula: C$_{46}$H$_{71}$NO$_{14}$.
 (3) Mass spectrum (SIMS): m/z 862 (M+H)$^+$.
 (4) Specific rotation: [α]$_D^{15}$ −52° (c 0.8, CH$_3$OH).
 (5) m.p.: 112°116° C.
 (6) $^1$H NMR spectrum (400 MHz, CDCl$_3$) δ (ppm): 2.24 (br d, 2-H), 2.76 (dd, 2-H), 5.13 (br d, 3-H), 3.25 (br d, 4-H), 3.57 (s, 4-OCH$_3$), 3.87 (br d, 5-H), 1.89 (m, 8-H), 4.07 (dd, 9-H), 5.62 (dd, 10-H), 6.68 (dd, 11-H), 6.08 (br dd, 12-H), 5.79 (ddd, 13-H), 5.03 (ddq, 15-H), 1.26 (d, 16-H$_3$), 2.31 (br dd, 17-H), 2.84 (br dd, 17-H), 9.63 (s, 18-H), 0.98 (d, 19-H$_3$), 2.51 (dq, 3-OCOCH$_2$CH$_3$), 2.64 (dq, 3-OCOCH$_2$CH$_3$), 1.21 (t, 3-OCOCH$_2$C$\overline{\text{H}}_3$), 4.54 (d, 1'-H), 3.49 (t, 4'-H), 3.28 (dq, 5'-H), 1.15 (d, 6'-H$_3$), 2.62 (s, 3'-N(CH$_3$)$_2$), 4.90 (d, 1''-H), 1.57 (dd, 2''-Hax), 2.22 (d, 2''-Heq), 1.15 (s, 3''-CH$_3$), 3.00 (d, 4''-H), 4.45 (br dq, 5''-H), 1.23'(d, 6''-H$_3$), 3.25 (s, 3''-OCH$_3$ ), 4.62 (d, 4''-OCH$_2$C$_6$H$_5$ ), 4.70 (d, 4''-OCH$_2$C$_6$H$_5$), 7.3-7.4 (m, 4''-OC$\overline{\text{H}}_2$C$_6$H$_5$).

EXAMPLE 7

Process (1) for producing compound (12) [a compound represented by the formula (I) wherein $R^1$ represents a hydrogen atom, $R^2$ represents a hydrogen atom, $R^3$ represents a hydrogen atom, $R^4$ represents a methyl group and $R^5$ represents an isoamyl group]:

As a seed medium, a medium comprising 2.0% of starch, 1.0% of glucose, 0.6% of wheat embryo, 0.5% of polypeptone, 0.3% of powdery yeast extract, 0.2% of soybean powder and 0.2% of calcium carbonate was employed. As a conversion medium, a medium comprising 3.0% of glucose, 1.5% of starch, 1.25% of soybean powder, 0.8% of wheat embryo, 0.125% of sodium chloride and 0.15% of calcium carbonate was employed. These media were adjusted to pH 7.0 and then sterilized prior to the use.

The above-mentioned seed medium was pipetted in 20 ml portions into two 100 ml-Erlenmeyer's flasks and sterilized at 120° C. for 30 minutes. Then the seed medium was inoculated with one platinum loopful of Phialophora PF1083 strain (FERM BP-3960), which had been stationarily incubated by slant agar culture containing 0.2% of yeast extract, 1.0% of starch and 2.0% of agar powder (pH 7.0) at 26° C. for 4 to 6 days, followed by incubating at 26° C. for 2 days under shaking. Thus a seed culture liquor was obtained. Next, the above-mentioned conversion medium was pipetted in 100 ml portions into five 500 ml-Erlenmeyer's flasks and sterilized at 120° C. for 30 minutes. Then 7.5 ml of a methanol solution containing 98 mg of the compound (3) was added to each flask in 1.5 ml portions and the conversion medium in each flask was inoculated with 5 ml of the seed culture liquor, followed by incubating at 26° C. for 9 days under shaking. After the completion of the incubation, the culture liquor was adjusted to pH 5 with 1N hydrochloric acid and then centrifuged at 3000 rpm for 10 minutes. Thus 400 ml of a transparent culture supernatant was obtained while the solid matters including the cells were removed. To the solid matters was added 400 ml of water and the resulting mixture was stirred followed by centrifugation. The washing liquor thus obtained was combined with the above-mentioned transparent culture supernatant. After adjusting the mixture to pH 9 with a 1N aqueous solution of sodium hydroxide, the conversion product was extracted with 750 ml portions of ethyl acetate twice. The ethyl acetate layer was dried over anhydrous sodium sulfate and then filtered. The filtrate was concentrated under reduced pressure and the residue thus obtained was purified by preparative TLC [developing system: chloroform/methanol/conc. aqueous ammonia (100:10:1)] to obtain 7.5 mg of the compound (12). Simultaneously, 7.2 mg of the compound (3) was recovered.

Physicochemical properties of the compound (12) obtained by microbial conversion (1) Color and appearance: colorless solid.
(2) Molecular formula: $C_{41}H_{71}NO_{13}$.
(3) Mass spectrum (EIMS): m/z 785 (M)+.
(4) Specific rotation: $[\alpha]_D^{17}$ −64° (c 0.8, $CH_3OH$).
(5) Melting at around 87° to 91° C. without showing any definite melting point.
(6) $^1H$ NMR spectrum (400 MHz, $CDCl_3$) δ(ppm): 2.22 (br d, 2-H), 2.71 (dd, 2-H), 3.80 (br d, 3-H), 3.10 (br d, 4-H), 3.55 (s, 4-$OCH_3$), 4.12 (br dd, 5-H), 1.91 (m, 8-H), 4.11 (dd, 9-H), 5.69 (dd, 10-H), 6.27 (dd, 11-H), 6.04 (br dd, 12-H), 5.62 (ddd, 13-H), 2.13 (dt, 14-H), 2.52 (br d, 14-H), 5.30 (ddq, 15-H), 1.31 (d, 16-$H_3$), 2.34 (br dd, 17-H), 2.88 (br dd, 17-H), 9.81 (br s, 18-H), 0.99 (d, 19-$H_3$), 4.60 (d, 1'-H), 3.18 (dd, 2'-H), 2.41 (t, 3'-H), 3.48 (t, 4'-H), 3.28 (dq, 5'-H), 1.18 (d, 6'-$H_3$), 2.57 (s, 3'-$N(CH_3)_2$), 4.90 (d, 1"-H), 1.57 (dd, 2"-Hax), 2.23 (d, 2"-Heq), 1.25 (s, 3"-$CH_3$), 2.79 (d, 4"-H), 4.43 (dq, 5"-H), 1.23 (d, 6"-$H_3$), 3.26 (s, 3"-$OCH_3$), 3.60 (dt, 4"-$OCH_2CH_2CH(CH_3)_2$), 3.64 (dt, 4"-$OC\underline{H}_2CH_2CH(CH_3)_2$), 1.52 (m, 4"-$OCH_2C\underline{H}_2CH(CH_3)_2$), 1.70 (m, 4"-$OCH_2C\underline{H}_2C\underline{H}(CH_3)_2$), 0.89 (d, 4"-$OCH_2CH_2C\underline{H}(CH_3)_2$).

EXAMPLE 8

Process for producing compound (13) [a compound represented by the formula (I) wherein $R^1$ represents a hydrogen atom, $R^2$ represents an acetyl group, $R^3$ represents a hydrogen atom, $R^4$ represents a methyl group and $R^5$ represents an isoamyl group]:

To 39.5 mg of the compound (12) was added 2.1 ml dry toluene to dissolve the compound and 18 μl of dry pyridine and 15 μl of acetyl chloride were successively added thereto, followed by stirring at room temperature for 35 minutes. Then the reaction mixture was extracted with 10 ml of ethyl acetate and 25 μl of triethylamine. The ethyl acetate layer was washed with 10 ml portions of water twice, dried over anhydrous sodium sulfate and then filtered. The filtrate was concentrated under reduced pressure and the residue thus obtained was dissolved in 4.0 ml of methanol and allowed to stand at room temperature for 24 hours. Then it was concentrated under reduced pressure and the residue thus obtained was purified by preparative TLC [developing system: chloroform/methanol (10:1)]. Thus 24.5 mg of the compound (13) was obtained.

Physicochemical properties of the compound (13)

(1) Color and appearance: colorless solid.
(2) Molecular formula: $C_{43}H_{73}NO_{14}$.
(3) Mass spectrum (EIMS): m/z 827 (M)+.
(4) Specific rotation: $[\alpha]_D^{26}$ −69° (c 1.0, $CH_3OH$).
(5) Melting at around 101° to 105° C. without showing any definite melting point.
(6) $^1H$ NMR spectrum (400 MHz, $CDCl_3$) δ(ppm): 2.22 (br d, 2-H), 2.71 (dd, 2-H), 3.78 (br d, 3-H), 3.09 (br d, 4-H), 3.54 (s, 4-$OCH_3$), 4.14 (br dd, 5-H), 2.31 (br t, 6-H), 0.97 (br dt, 7-H), 1.63 (br dt, 7-H), 5.18 (dd, 9-H), 2.00 (s, 9-$OCOCH_3$), 5.60 (dd, 10-H), 6.40 (dd, 11-H), 6.03 (br dd, 12-H), 5.65 (ddd, 13-H), 2.12 (dt, 14-H), 2.51 (br d, 14-H), 5.29 (ddq, 15-H), 1.30 (d, 16-$H_3$), 2.44 (br dd, 17-H), 2.81 (br dd, 17-H), 9.80 (br s, 18-H), 0.98 (d, 19-$H_3$), 4.59 (d, 1'-H), 3.19 (br dd, 2'-H), 2.43 (t, 3'-H), 3.48 (t, 4'-H), 3.27 (dq, 5'-H), 1.18 (d, 6'-$H_3$), 2.59 (s, 3'-$N(CH_3)_2$), 4.90 (d, 1"-H), 1.56 (dd, 2"-Hax), 2.23 (d, 2"-Heq), 1.24 (s, 3"-$CH_3$), 2.78 (d, 4"-H), 4.40 (dq, 5"-H), 1.22 (d, 6"-$H_3$), 3.25 s, 3"-$OCH_3$), 3.60 (dt, 4"-$OCH_2CH_2CH(CH_3)_2$), 3.64 (dt, 4"-$OC\underline{H}_2CH_2CH(CH_3)_2$), 1.51 (m, 4"-$OCH_2C\underline{H}_2CH(CH_3)_2$), 1.69 (m, 4"-$OCH_2C\underline{H}_2C\underline{H}(CH_3)_2$), 0.89 (d, 4"-$OCH_2CH_2C\underline{H}(CH_3)_2$).

EXAMPLE 9

Process for producing compound (16) [a compound represented by the formula (I) wherein $R^1$ represents a hydrogen atom, $R^2$ represents a hydrogen atom, $R^3$ represents a hydrogen atom, $R^4$ represents a methyl group and $R^5$ represents a benzyl group]:

The same seed medium as described in Example 7 was pipetted in 20 ml portions into two 100 ml-Erlenmeyer's flasks and sterilized at 120° C. for 30 minutes. Then the seed medium was inoculated with one platinum loopful of Phialophora PF1083 strain (FERM BP-3960), which had been incubated by slant agar culture, followed by incubating at 26° C. for 2 days under shaking. Thus a seed culture liquor was obtained. Next, the same conversion medium as described in Example 7 was pipetted in 100 ml portions into five 500 ml-Erlenmeyer's flasks and sterilized at 120° C. for 30 minutes. Then 7.5 ml of a methanol solution containing 100 mg of the compound (6) was added to each flask in 1.5 ml portions and the conversion medium in each flask was inoculated with 5 ml of the seed culture liquor, followed by incubating at 26° C. for 9 days under shaking. After the completion of the incubation, the culture liquor was adjusted to pH 5 with 1N hydrochloric acid and then centrifuged at 3000 rpm for 10 minutes. Thus 400 ml of a transparent culture supernatant was obtained while the solid matters including the cells were removed. 400 ml of water was added to the solid matters and the resulting mixture was stirred followed by centrifugation. The washing liquor thus obtained was combined with the above-mentioned transparent culture supernatant. After adjusting the mixture to pH 9 with a 1N aqueous solution of sodium hydroxide, the conversion product was extracted with 750 ml portions of ethyl acetate twice. The ethyl acetate layer was dried over anhydrous sodium sulfate and then filtered. The filtrate was concentrated under reduced pressure and the residue thus obtained was purified by preparative TLC [developing system: chloroform/methanol/conc. aqueous ammonia (100:10:1)] to obtain 8.1 mg of the compound (16). Simultaneously, 7.7 mg of the compound (6) was recovered.

Physicochemical properties of the compound (16)
(1) Color and appearance: colorless solid.
(2) Molecular formula: $C_{43}H_{67}NO_{13}$.
(3) Mass spectrum (FDMS): m/z 805 (M)+.
(4) Specific rotation: $[\alpha]_D^{27}$ −67° (c 1.0, $CH_3OH$).
(5) Melting at around 104° to 108° C. without showing any definite melting point.
(6) $^1H$ NMR spectrum (400 MHz, $CDCl_3$) δ(ppm): 2.22 (br d, 2-H), 2.70 (dd, 2-H), 3.79 (br d, 3-H), 3.09 (br d, 4-H), 3.54 (s, 4-$OCH_3$), 4.11 (br dd, 5-H), 1.60 (br dt, 7-H), 1.90 (m, 8-H), 4.10 (dd, 9-H), 5.68 (dd, 10-H), 6.26 (dd, 11-H), 6.03 (br dd, 12-H), 5.60 (ddd, 13-H), 2.12 (dt, 14-H), 2.50 (br d, 14-H), 5.29 (ddq, 15-H), 1.30 (d, 16-$H_3$), 2.33 (br dd, 17-H), 2.86 (br dd, 17-H), 9.80 (s, 18-H), 0.99 (d, 19-$H_3$), 4.59 (d, 1'-H), 3.20 (dd, 2'-H), 2.43 (t, 3'-H), 3.48 (t, 4'-H), 3.27 (dq, 5'-H), 1.18 (d, 6'-$H_3$), 2.58 (s, 3'-N($CH_3$)$_2$), 4.90 (d, 1''-H), 1.56 (dd, 2''-Hax), 2.22 (d, 2''-Heq), 1 14 (s, 3''-$CH_3$), 2.99 (d, 4''-H), 4.47 (dq, 5''-H), 1.23 (d, 6''-$H_3$), 3.25 (s, 3''-$OCH_3$), 4.62 (d, 4''-$OCH_2C_6H_5$), 4.70 (d, 4''-$OCH_2C_6H_5$), 7.3-7.4 (m, 4''-$OCH_2C_6H_5$).

EXAMPLE 10

Process for producing compound (17) [a compound represented by the formula (VIII) wherein $R^7$ represents a propionyl group and $R^8$ represents a TBDMS group]:

To 1.00 g of leucomycin $A_7$ was added 12 ml of dry dimethylformamide to dissolve leucomycin $A_7$ and 1.18 g of t-butyldimethylsilyl chloride and 1.08 g of imidazole were added thereto. The resulting mixture was stirred at 50° C. for 24 hours. The reaction mixture was cooled to room temperature and 50 ml of methanol was added thereto, followed by stirring at room temperature for 30 minutes. After concentrating the reaction mixture under reduced pressure, the resulting residue was extracted with 500 ml of benzene and the benzene layer was washed successively with 500 ml portions of a saturated aqueous solution of sodium hydrogencarbonate twice and 500 ml portions of a saturated aqueous solution of sodium chloride twice. Then the organic layer was dried over anhydrous sodium sulfate and filtered. The filtrate was concentrated under reduced pressure and dried. Thus 1.22 g of a crude compound (17) was obtained. A 60 mg portion of this crude compound was purified by preparative TLC [developing system: chloroform/methanol (50: 1)] to thereby give 35 mg of the compound (17).

Physicochemical properties of the compound (17)
(1) Color and appearance: colorless solid.
(2) Molecular formula: $C_{56}H_{105}NO_{14}Si_3$.
(3) Mass spectrum (SIMS): m/z 1100 (M+H)+.
(4) Specific rotation: $[\alpha]_D^{25}$ −17° (c 1.0, $CH_3OH$).
(5) Melting at around 105° to 107° C. without showing any definite melting point.
(6) $^1H$ NMR spectrum (400 MHz, $CDCl_3$) δ(ppm): 2.61 (dd, 2-H), 4.22 (m, 3-H), 3.14 (br s, 4-H), 3.38 (s, 4-$OCH_3$), 3.42 (br dd, 5-H), 0.41 (br dd, 7-H), 4.23 (m, 9-H), 5.75 (dd, 10-H), 6.12 (m, 11-H), 6.12 (m, 12-H), 5.62 (dt, 13-H), 4.85 (ddq, 15-H), 1.30 (d, 16-$H_3$), 1.38 (dt, 17-H), 1.66 (br d, 17-H), 4.63 (br dd, 18-H), 4.21 (d, 1'-H), 3.52 (dd, 2'-H), 2.55 (t, 3'-H), 3.35 (t, 4'-H), 1.25 (d, 6'-$H_3$), 2.53 (s, 3'-N($CH_3$)$_2$), 5.10 (d, 1''-H), 1.86 (dd, 2''-Hax), 2.00 (d, 2''-Heq), 1.11 (s, 3''-$CH_3$), 4.62 (d, 4''-H), 4.37 (dq, 5''-H), 1.17 (t, 4''-OCOC$H_2$C$H_3$).

EXAMPLE 11

Process for producing compound (18) [a compound represented by the formula (IX) wherein $R^8$ represents a TBDMS group]:

One hundred thirty ml of benzene was added to 1.16 g of the crude compound (17) prepared in Example 10 to dissolve the compound therein and 65 ml of a 25% aqueous solution of sodium hydroxide and 358 mg of tetra-n-butylammonium hydrogensulfate were added thereto, followed by vigorously stirring at room temperature for 2 hours. Then the benzene layer was collected and washed with 150 ml portions of a saturated aqueous solution of sodium chloride twice. The organic layer was dried over anhydrous sodium sulfate and filtered. Then the filtrate was concentrated under reduced pressure and the residue thus obtained was purified by silica gel column chromatography [200 g: chloroform/methanol (30:1)]. Thus 795 mg of the compound (18) was obtained.

Physicochemical properties of the compound (18)
(1) Color and appearance: colorless solid.
(2) Molecular formula: $C_{53}H_{101}NO_{13}Si_3$.
(3) Mass spectrum (SIMS): m/z 1044 (M+H)+.
(4) Specific rotation: $[\alpha]_D^{25}$ −12° (c 1.0, $CH_3OH$).
(5) Melting at around 98° to 100° C. without showing any definite melting point.
(6) $^1$ NMR spectrum (400 MHz, $CDCl_3$) δ(ppm): 2.37 (br dd, 2-H), 2.61 (dd, 2-H), 4.21 (m, 3-H), 3.13 (br s, 4-H), 3.37 (s, 4-$OCH_3$), 3.42 (br dd, 5-H), 0.41 (br dd, 7-H), 4.23 (m, 9-H), 5.74 (dd, 10-H), 6.11 (m, 11-H), 6.91 (m, 12-H), 5.62 (dt, 13-H), 4.85 (ddq, 15-H), 1.30 (d, 16-$H_3$), 1.38 (dt, 17-H), 1.66 (br d, 17-H), 4.63 (br dd, 18-H), 4.20 (d, 1'-H), 3.57 (dd, 2'-H), 2.53 (t, 3'-H), 3.32 (t, 4'-H), 1.25 (d, 6'-$H_3$), 2.51 (s, 3'-N($CH_3$)$_2$), 5.08 (d, 1''-H), 1.77 (dd, 2''-Hax), 2.02 (d, 2''-Heq), 1.22 (s, 3''-$CH_3$), 2.94 (t, 4''-H), 3.99 (dq, 5''-H), 1.30 (d, 6''-$H_3$).

EXAMPLE 12

Process for producing compound (19) [a compound represented by the formula (X) wherein $R^5$ represents an ethyl group and $R^8$ represents a TBDMS group]:

To 200 mg of the compound (18) was added to 3.0 ml of dry dimethylformamide to dissolve the compound and 38 mg of 60% oily sodium hydride was added thereto. The resulting mixture was stirred at room temperature. When bubbling was weakened, 899 mg of ethyl iodide was added thereto and the resulting mixture was stirred at 45° C. for 30 minutes. Then the reaction mixture was cooled to room temperature. After slowly adding 100 ml of water, the reaction mixture was extracted with 100 ml of chloroform. 100 ml of chloroform was added again to the aqueous layer. After extracting, the chloroform layers were combined and washed with 100 ml portions of a saturated aqueous solution of sodium chloride twice. The chloroform layer was dried over anhydrous sodium sulfate and filtered. The filtrate was concentrated under reduced pressure and the residue thus obtained was purified by preparative TLC [developing system: hexane/ethyl acetate (2:1)]. Thus 140 mg of the compound (19) was obtained.

Physicochemical properties of the compound (19)

(1) Color and appearance: colorless solid.
(2) Molecular formula: $C_{55}H_{105}NO_{13}Si_3$.
(3) Mass spectrum (SIMS): m/z 1072 $(M+H)^+$.
(4) Specific rotation: $[\alpha]_D^{26}$ −17° (c 1.0, $CH_3OH$).
(5) m.p.: 92° C.
(6) $^1H$ NMR spectrum (400 MHz, $CDCl_3$) δ(ppm): 2.37 (br dd, 2-H), 2.60 (dd, 2-H), 4.21 (m, 3-H), 3.37 (s, 4-$OCH_3$), 3.38 (br dd, 5-H), 0.39 (br dd, 7-H), 4.21 (m, 9-H), 5.73 (dd, 10-H), 6.10 (m, 11-H), 6.10 (m, 12-H), 5.60 (dt, 13-H), 4.82 (ddq, 15-H), 1.38 (dt, 17-H), 1.63 (br d, 17-H), 4.61 (br dd, 18-H), 4.16 (d, 1'-H), 3.44 (dd, 2'-H), 2.52 (t, 3'-H), 3.34 (t, 4'-H), 2.50 (s, 3'-N($CH_3$)$_2$), 5.02 (d, 1''-H), 1.75 (dd, 2''-Hax), 1.96 (br d, 2''-Heq), 1.23 (s, 3''-$CH_3$), 2.70 (d, 4''-H), 4.22 (dq, 5''-H ), 3.66 (dq, 4''-O$CH_2$$CH_3$), 3.68 (dq, 4''-O$CH_2$$CH_3$).

EXAMPLE 13

Process for producing compound (20) [a compound represented by the formula (XI) wherein $R^4$ represents a methyl group, $R^5$ represents an ethyl group and $R^8$ represents a TBDMS group]:

To 120 mg of the compound (19) was added 6.0 ml of chloroform to dissolve the compound and 29 mg of m-chloroperbenzoic acid was added thereto, followed by stirring at room temperature for 5 minutes. Then the reaction mixture was dropped into 30 ml of a 10% aqueous solution of sodium thiosulfate and extracted with 60 ml of chloroform. The chloroform layer was successively washed with 60 ml portions of a saturated aqueous solution of sodium hydrogencarbonate twice and 60 ml portions of a saturated aqueous solution of sodium chloride twice. Then the organic layer was dried over anhydrous sodium sulfate and filtered. The filtrate was concentrated under reduced pressure. To 127 mg of the solid thus obtained was added 1.3 ml of dry dimethylformamide to dissolve the solid and 24 mg of 60% oily sodium hydride was added thereto. The resulting mixture was stirred at room temperature. When bubbling was weakened, 498 mg of methyl iodide was added thereto and the resulting mixture was stirred at 45° C. for 1 hour. Then the reaction mixture was cooled to room temperature. After slowly adding 30 ml of water, the reaction mixture was extracted with 60 ml of chloroform. Sixty ml of chloroform was added to the aqueous layer and extraction was carried out again. The chloroform layers were combined and washed with 100 ml portions of a saturated aqueous solution of sodium chloride twice. The chloroform layer was dried over anhydrous sodium sulfate and filtered. The filtrate was concentrated under reduced pressure and the residue thus obtained was charged on preparative TLC. After allowing to stand for 2 days, it was purified by developing [developing system: chloroform/methanol (20 : 1)]. Thus 68 mg of the compound (20) was obtained.

Physicochemical properties of the compound (20)

(1) Color and appearance: colorless solid.
(2) Molecular formula: $C_{50}H_{93}NO_{13}Si_2$.
(3) Mass spectrum (SIMS): m/z 971 $(M)^+$.
(4) Specific rotation: $[\alpha]_D^{23}$ −2° (c $CH_3OH$).
(5) Melting at around 72° to 74° C. without showing any definite melting point.
(6) $^1H$ NMR spectrum (400 MHz, $CDCl_3$) δ(ppm): 4.05 (br dt, 3-H), 3.43 (s, 4-$OCH_3$), 3.45 (br d, 5-H), 0.41 (br dd, 7-H), 4.18 (br d, 9-H), 5.72 (dd, 10-H), 6.10 (m, 11-H), 6.10 (m, 12-H), 5.62 (dt, 13-H), 4.80 (ddq, 15-H), 1.30 (d, 16-$H_3$), 1.43 (dt, 17-H), 1.66 (br d, 17-H), 4.56 (br dd, 18-H), 4.29 (d, 1'-H), 3.32 (dd, 2'-H), 2.45 (t, 3'-H), 3.36 (t, 4'-H), 2.55 (s, 3'-N($CH_3$)$_2$), 4.87 (d, 1''-H), 1.52 (dd, 2''-Hax), 2.23 (d, 2''-Heq), 1.21 (s, 3''-$CH_3$), 3.25 (s, 3''-$OCH_3$), 2.76 (d, 4''-H), 4.45 (dq, 5''-H), 3.64 (dq, 4''-O$CH_2$$CH_3$), 3.68 (dq, 4''-O$CH_2$$CH_3$).

EXAMPLE 14

Process for producing compound (8) [a compound represented by the formula (I) wherein $R^1$ represents a hydrogen atom, $R^2$ represents a hydrogen atom, $R^3$ represents a hydrogen atom, $R^4$ represents a methyl group and $R^5$ represents an ethyl group]:

To 63 mg of the compound (20) was added 530 μl of a 2M solution of tetra-n-butylammonium fluoride in tetrahydrofuran and the mixture was reacted at 45° C. for 1 hour. Then the reaction mixture was cooled to room temperature, dropped into 5.2 ml of a 5% aqueous solution of potassium hydrogensulfate and then extracted with 30 ml portions of chloroform twice. The chloroform layers were combined and successively washed with 50 ml portions of a saturated aqueous solution of sodium hydrogencarbonate twice and 50 ml portions of a saturated aqueous solution of sodium chloride twice. The organic layer was dried over anhydrous sodium sulfate and filtered. The filtrate was concentrated under reduced pressure and the residue thus obtained was purified by silica gel column chromatography [10 g: chloroform/methanol (50:1)]. Thus 24 mg of the compound (8) was obtained.

Physicochemical properties of the compound (8)

(1) Color and appearance: colorless solid.
(2) Molecular formula: $C_{38}H_{65}NO_{13}$.
(3) Mass spectrum (SIMS): m/z 744 $(M+H)^+$.
(4) Specific rotation: $[\alpha]_D^{24}$ −60° (c 1.0, $CH_{33}OH$).
(5) Melting at around 89° to 92° C. without showing any definite melting point.
(6) $^1H$ NMR spectrum (400 MHz, $CDCl_3$) δ(ppm): 2.20 (br d, 2-H), 2.68 (dd, 2-H), 3.76 (br d, 3-H), 3.07 (br d, 4-H), 3.52 (s, 4-$OCH_3$), 4.08 (br dd, 5-H), 1.88 (m, 8-H), 4.07 (dd, 9-H), 5.66 (dd, 10-H), 6.24 (dd, 11-H), 6.01 (br dd, 12-H), 5.58 (ddd, 13-H), 2.10 (dt, 14-H), 2.48 (br d, 14-H), 5.26 (ddq, 15-H), 1.28 (d, 16-$H_3$), 2.31 (br dd, 17-H), 2.85 (br dd, 17-H), 9.80 (br s, 18-H), 0.99 (d, 19-$H_3$), 4.56 (d, 1'-H), 2.40 (t, 3'-H), 3.45 (t, 4'-H), 3.24

(dq, 5'-H), 1.15 (d, 6'-H$_3$), 2.57 (s, 3'-N(CH$_3$)$_2$), 4.87 (d, 1''-H), 1.53 (dd, 2''-Hax), 2.22 (d, 2''-Heq), 1.21 (s, 3''-CH$_3$), 2.76 (d, 4''-H), 4.39 (dq, 5''-H), 1.21 (d, 6''-H$_3$), 3.22 (s, 3''-OCH$_3$), 3.63 (dq, 4''-OC$\underline{H}_2$CH$_3$), 3.67 (dq, 4''-OC$\underline{H}_2$CH$_3$).

EXAMPLE 15

Process for producing compound (21) [a compound represented by the formula (X) wherein R$^5$ represents an n-propyl group and R$^8$ represents a TBDMS group]:

To 200 mg of the compound (18) was added 3.0 ml of dry dimethylformamide to dissolve the compound and 38 mg of 60% oily sodium hydride was added thereto. The resulting mixture was stirred at room temperature. When bubbling was weakened, 979 mg of n-propyl iodide was added thereto and the obtained mixture was stirred at 45° C. for 30 minutes. Then the reaction mixture was cooled to room temperature. After slowly adding 100 ml of water, the reaction mixture was extracted with 100 ml of chloroform. One hundred ml of chloroform was added to the aqueous layer and extraction was carried out again. The chloroform layers were combined and washed with 100 ml portions of a saturated aqueous solution of sodium chloride twice. The chloroform layer was dried over anhydrous sodium sulfate and filtered. The filtrate was concentrated under reduced pressure and the residue thus obtained was purified by preparative TLC [developing system: hexane/ethyl acetate (2:1)]. Thus 187 mg of the compound (21) was obtained.

Physicochemical properties of the compound (21)
(1) Color and appearance: colorless solid.
(2) Molecular formula: C$_{56}$H$_{107}$NO$_{13}$Si$_3$.
(3) Mass spectrum (FDMS): m/z 1085 (M+H)$^+$.
(4) Specific rotation: [α]$_D^{26}$ −11° (c 1.0, CH$_3$OH).
(5) Melting at around 88° to 90° C. without showing any definite melting point.
(6) $^1$H NMR spectrum (400 MHz, CDCl$_3$) δ(ppm): 2.38 (br dd, 2-H), 2.60 (dd, 2-H), 4.22 (m, 3-H), 3.37 (s, 4-OCH$_3$), 3.39 (br dd, 5-H), 0.39 (br dd, 7-H), 4.22 (m, 9-H), 5.75 (dd, 10-H), 6.10 (m, 11-H), 6.10 (m, 12-H), 5.61 (dt, 13-H), 4.82 (ddq, 15-H), 1.39 (dt, 17-H), 4.62 (br dd, 18-H), 4.17 (d, 1'-H), 3.43 (dd, 2'-H), 2.53 (t, 3'-H), 3.35 (t, 4'-H), 2.51 (s, 3'-N(CH$_3$)$_2$), 5.03 (d, 1''-H), 1.76 (dd, 2''-Hax), 1.97 (br d, 2''Heq), 1.25 (s, 3''-CH$_3$), 2.71 (d, 4''-H), 4.23 (dq, 5''-H), 3.56 (t, 4''-OCH$_2$CH$_3$), 0.92 (t, 4''-OCH$_2$C$\underline{H}_3$).

EXAMPLE 16

Process for producing compound (22) [a compound represented by the formula (XI) wherein R$^4$ represents a methyl group, R$^5$ represents an n-propyl group and R$^5$ represents a TBDMS group]:

To 187 mg of the compound (21) was added 9.0 ml of chloroform to dissolve the compound and 44 mg of m-chloroperbenzoic acid was added thereto, followed by stirring at room temperature for 5 minutes. Then the reaction mixture was dropped into 50 ml of a 10% aqueous solution of sodium thiosulfate and extracted with 100 ml of chloroform. The chloroform layer was successively washed with 100 ml portions of a saturated aqueous solution of sodium hydrogencarbonate twice and 100 ml portions of a saturated aqueous solution of sodium chloride twice. Then the organic layer was dried over anhydrous sodium sulfate and filtered. The filtrate was concentrated under reduced pressure. To 164 mg of the solid thus obtained was added 1.6 ml of dry dimethylformamide to dissolve the solid and 30 mg of 60% oily sodium hydride was added thereto. The resulting mixture was stirred at room temperature. When bubbling was weakened, 635 mg of methyl iodide was added thereto and the resulting mixture was stirred at 45° C. for 1 hour. Then the reaction mixture was cooled to room temperature. After slowly adding 40 ml of water, the reaction mixture was extracted with 80 ml of chloroform. Eighty ml of chloroform was added to the aqueous layer and extraction was carried out again. The chloroform layers were combined and washed with 150 ml portions of a saturated aqueous solution of sodium chloride twice. The chloroform layer was dried over anhydrous sodium sulfate and filtered. The filtrate was concentrated under reduced pressure and the residue thus obtained was charged on preparative TLC. After allowing to stand for 2 days, it was purified by developing [developing system: chloroform/methanol (20:1)]. Thus 44 mg of the compound (22) was obtained.

Physicochemical properties of the compound (22)
(1) Color and appearance: colorless solid.
(2) Molecular formula: C$_{51}$H$_{95}$NO$_{13}$Si$_2$.
(3) Mass spectrum (SIMS): m/z 986 (M+H)$^+$.
(4) Specific rotation: [α]$_D^{24}$ −3° (c 1.0, CH$_3$OH).
(5) Melting at around 67° to 69° C. without showing any definite melting point.
(6) $^1$H NMR spectrum (400 MHz, CDCl$_3$) δ(ppm): 4.05 (br dt, 3-H), 3.43 (s, 4-OCH$_3$), 0.42 (br dd, 7-H), 4.18 (br d, 9-H), 5.73 (dd, 10-H), 6.10 (m, 11-H), 6.10 (m, 12-H), 5.62 (dt, 13-H), 4.80 (ddq, 15-H), 1.31 (d, 16-H$_3$), 1.43 (dt, 17-H), 1.65 (br d, 17-H), 4.57 (br dd, 18-H), 4.30 (d, 1'-H), 3.32 (dd, 2'-H), 2.47 (t, 3'-H), 3.36 (t, 4'-H), 2.56 (s, 3'-N(CH$_3$)$_2$), 4.87 (d, 1''-H), 1.54 (dd, 2''-Hax), 2.22 (d, 2''Heq), 1.23 (s, 3''-CH$_3$), 2.77 (d, 4''-H), 4.45 (dq, 5''-H), 3.25 (s, 3''-OCH$_3$), 3.54 (dt, 4''-OC$\underline{H}_2$CH$_3$), 3.57 (dt, 4''-OCH$_2$CH$_2$CH$_3$), 1.63 (m, 4''-OCH$_2$C$\underline{H}_3$.

EXAMPLE 17

Process for producing compound (9) [a compound represented by the formula (I) wherein R$^1$ represents a hydrogen atom, R$^2$ represents a hydrogen atom, R$^3$ represents a hydrogen atom, R$^4$ represents a methyl group and R$^5$ represents an n-propyl group]:

To 41 mg of the compound (22) was added 330 μl of a 2M solution of tetra-n-butylammonium-fluoride in tetrahydrofuran and the mixture was allowed to react at 45° C. for 1 hour. Then the reaction mixture was cooled to room temperature, dropped into 3.3 ml of a 5% aqueous solution of potassium hydrogensulfate and then extracted with 20 ml portions of chloroform twice. The chloroform layers were combined and successively washed with 40 ml portions of a saturated aqueous solution of sodium hydrogencarbonate twice and 40 ml portions of a saturated aqueous solution of sodium chloride twice. The organic layer was dried over anhydrous sodium sulfate and filtered. The filtrate was concentrated under reduced pressure and the residue thus obtained was purified by silica gel column chromatography [10 g: chloroform/methanol (50:1)]. Thus 30 mg of the compound (9) was obtained.

Physicochemical properties of the compound (9)
(1) Color and appearance: colorless solid.
(2) Molecular formula: C$_{39}$H$_{67}$NO$_{13}$.
(3) Mass spectrum (SIMS): m/z 758 (M+H)$^+$.
(4) Specific rotation: [α]$_D^{25}$ −55° (c 1.0, CH$_3$OH).
(5) Melting at around 79° C. to 81° C. without showing any definite melting point.
(6) $^1$H NMR spectrum (400 MHz, CDCl$_3$) δ(ppm): 2.20 (br d, 2-H), 2.68 (dd, 2-H), 3.77 (br d, 3-H), 3.07 (br d, 4-H), 3.52 (s, 4-OCH$_3$), 4.08 (br dd, 5-H), 1.88 (m, 8-H), 4.07 (dd, 9-H), 5.66 (dd, 10-H), 6.24 (dd, 11-H), 6.01 (br dd, 12-H), 5.58 (ddd, 13-H), 2.10 (dt, 14-H), 2.48 (br d, 14-H), 5.26 (ddq, 15-H), 1.28 (d, 16-H$_3$), 2.31 (br dd, 17-H), 2.85 (br dd, 17-H), 9.80 (br s, 18-H), 0.99 (d, 19-H$_3$), 4.56 (d, 1'-H), 3.16 (dd, 2'-H), 2.39 (t, 3'-H), 3.45 (t, 4'-H), 3.25 (dq, 5'-H), 1.15 (d, 6'-H$_3$), 2.55 (s, 3'-N(CH$_3$)$_2$), 4.87 (d, 1''-H), 1.54 (dd, 2''-Hax), 2.21 (d, 2''-Heq), 1.22 (s, 3''-CH$_3$), 2.76 (d, 4''-H), 4.40 (dq, 5''-H), 1.21 (d, 6''-H$_3$), 3.23 (s, 3''-OCH$_3$), 3.52 (dt, 4''-OC$\underline{H}_2$CH$_2$CH$_3$), 3.56 (dt, 4''-OC$\underline{H}_2$CH$_2$CH$_3$), 1.60 (m, 4''-OCH$_2$C$\underline{H}_2$CH$_3$), 0.90 (t, 4''-OCH$_2$CH$_2$C$\underline{H}_3$).

EXAMPLE 18

Process for producing compound (23) [a compound represented by the formula (X) wherein R$^5$ represents an n-butyl group and R$^8$ represents a TBDMS group]:

To 200 mg of the compound (18) was added 3.0 ml of dry dimethylformamide to dissolve the compound and 38 mg of 60% oily sodium hydride was added thereto. The resulting mixture was stirred at room temperature. When bubbling was weakened, 788 mg of n-butyl bromide was added thereto and the resulting mixture was stirred at 45° C. for 30 minutes. Then the reaction mixture was cooled to room temperature. After slowly adding 100 ml of water, the reaction mixture was extracted with 100 ml of chloroform. One hundred ml of chloroform was added to the aqueous layer and extraction was carried out again. The chloroform layers were combined and washed with 100 ml portions of a saturated aqueous solution of sodium chloride twice. The chloroform layer was dried over anhydrous sodium sulfate and filtered. The filtrate was concentrated under reduced pressure and the residue thus obtained was purified by preparative TLC [developing system: hexane/ethyl acetate (2:1)]. Thus 140 mg of the compound (23) was obtained.

Physicochemical properties of the compound (23)
 (1) Color and appearance: colorless solid.
 (2) Molecular formula: C$_{57}$H$_{109}$NO$_{13}$Si$_3$.
 (3) Mass spectrum (FDMS): m/z 1099 (M)$^+$.
 (4) Specific rotation: [α]$_D^{26}$ −13° (c 1.0, CH$_3$OH).
 (5) Melting at around 82° to 83° C. without showing any definite melting point.
 (6) $^1$H NMR spectrum (400 MHz, CDCl$_3$) δ(ppm): 2.38 (br dd, 2-H), 2.60 (dd, 2-H), 4.22 (m, 3-H), 3.37 (s, 4-OCH$_3$), 3.39 (br dd, 5-H), 0.40 (br dd, 7-H), 4.22 (m, 9-H), 5.74 (dd, 10-H), 6.11 (m, 11-H), 6.11 (m, 12-H), 5.61 (dt, 13-H), 4.82 (ddq, 15-H), 1.39 (dt, 17-H), 1.64'(br d, 17-H), 4.62 (br dd, 18-H), 4.17 (d, 1'-H), 3.43 (dd, 2'-H), 2.53 (t, 3'-H), 3.34 (t, 4'-H), 2.51 (s, 3'-N(CH$_3$)$_2$), 5.03 (d, 1''-H), 1.75 (dd, 2''-Hax), 1.97 (br d, 2''-Heq), 1.24 (s, 3''-CH$_3$), 2.70 (d, 4''-H), 4.22 (dq, 5''-H), 3.60 (dt, 4''-OC$\underline{H}_2$CH$_2$CH$_2$CH$_3$), 0.90 (t, 4''-OCH$_2$C$\underline{H}_2$CH$_2$CH$_3$).

EXAMPLE 19

Process for producing compound (24) [a compound represented by the formula (XI) wherein R$^4$ represents a methyl group, R$^5$ represents an n-butyl group and R$^8$ represents a TBDMS group]:

Seven ml of chloroform was added to 140 mg of the compound (23) to dissolve the compound therein and 33 mg of m-chloroperbenzoic acid was added thereto, followed by stirring at room temperature for 5 minutes. Then the reaction mixture was dropped into 35 ml of a 10% aqueous solution of sodium thiosulfate and extracted with 70 ml of chloroform. The chloroform layer was successively washed with 70 ml portions of a saturated aqueous solution of sodium hydrogencarbonate twice and 70 ml portions of a saturated aqueous solution of sodium chloride twice. Then the organic layer was dried over anhydrous sodium sulfate and filtered. The filtrate was concentrated under reduced pressure to thereby give 141 mg of a solid product. To 129 mg of the solid thus obtained was added 1.3 ml of dry dimethylformamide to dissolve the solid and 23 mg of 60% oily sodium hydride was added thereto. The resulting mixture was stirred at room temperature. When bubbling was weakened, 494 mg of methyl iodide was added thereto and the resulting mixture was stirred at 45° C. for 1 hour. Then the reaction mixture was cooled to room temperature. After slowly adding 30 ml of water, the reaction mixture was extracted with 60 ml of chloroform. Sixty ml of chloroform was added to the aqueous layer and extraction was carried out again. The chloroform layers were combined and washed with 120 ml portions of a saturated aqueous solution of sodium chloride twice. The chloroform layer was dried over anhydrous sodium sulfate and filtered. The filtrate was concentrated under reduced pressure and the residue thus obtained was charged on preparative TLC. After allowing to stand for 3 days, it was purified by developing [developing system: chloroform/methanol (20:1)]. Thus 80 mg of the compound (24) was obtained.

Physicochemical properties of the compound (24)
 (1) Color and appearance: colorless solid.
 (2) Molecular formula: C$_{52}$H$_{97}$NO$_{13}$Si$_2$.
 (3) Mass spectrum (SIMS): m/z 999 (M+H)$^+$.
 (4) Specific rotation: [α]$_D^{24}$ −4° (c 1.0, CH$_3$OH).
 (5) Melting at around 67° to 68° C. without showing any definite melting point.
 (6) $^1$H NMR spectrum (400 MHz, CDCl$_3$) δ(ppm): 4.05 (br dt, 3-H), 3.44 (s, 4-OCH$_3$), 3.46 (dd, 5-H), 0.42 (br dd, 7-H), 4.18 (br d, 9-H), 5.73 (dd, 10-H), 6.10 (m, 11-H), 6.10 (m, 12-H), 5.62 (dt, 13-H), 4.80 (ddq, 15-H), 1.30 (d, 16-H$_3$), 1.43 (dt, 17-H), 1.66 (br d, 17-H), 4.56 (br dd, 18-H), 4.29 (d, 1'-H), 3.32 (dd, 2'-H), 2.46 (t, 3'-H), 3.36 (t, 4'-H), 2.55 (s, 3'-N(CH$_3$)$_2$) 4.87 (d, 1''-H), 1.53 (dd, 2''-Hax), 2.21 (d, 2''-Heq), 1.22 (s, 3''-CH$_3$), 2.76 (d, 4''-H), 4.45 (dq, 5''-H), 3.25 (s, 3''-OCH$_3$), 3.57 (dt, 4''-OC$\underline{H}_2$CH$_2$CH$_2$, CH$_3$), 3.61 (dt, 4''-OCHCH$_2$C$\underline{H}_2$CH$_3$), 1.58 (m, 4''-OCH$_2$CH$_2$CH$_2$CH$_3$), 1.36 (m, 4''-OCH$_2$CH$_2$CH$_2$CH$_3$), 0.99 (t, 4''-OCH$_2$CH$_2$CH$_2$C$\underline{H}_3$).

EXAMPLE 20

Process for producing compound (10) [a compound represented by the formula (I) wherein R$^1$ represents a hydrogen atom, R$^2$ represents a hydrogen atom, R$^3$ represents a hydrogen atom, R$^4$ represents a methyl group and R$^5$ represents an n-butyl group]:

To 75 mg of the compound (24) was added 600 μl of a 2M solution of tetra-n-butylammonium fluoride in tetrahydrofuran and the mixture was allowed to react at 45° C. for 1 hour. Then the reaction mixture was cooled to room temperature, dropped into 6.0 ml of a 5% aqueous solution of potassium hydrogensulfate and then extracted with 40 ml portions of chloroform twice. The chloroform layers were combined and successively washed with 80 ml portions of a saturated aqueous solution of sodium hydrogencarbonate twice and 80 ml portions of a saturated aqueous solution of sodium chloride twice. The organic layer was dried over anhydrous sodium sulfate and filtered. The filtrate was concentrated under reduced pressure and the residue thus obtained was purified by silica gel column chromatography [10 g: chloroform/methanol (50:1)]. Thus 30 mg of the compound (10) was obtained.

Physicochemical properties of the compound (10)
(1) Color and appearance: colorless solid.
(2) Molecular formula: $C_{40}H_{69}NO_{13}$.
(3) Mass spectrum (SIMS): m/z 772 (M+H)+.
(4) Specific rotation: $[\alpha]_D^{25}$ −54° (c 1.0, $CH_3OH$).
(5) Melting at around 80° to 84° C. without showing any definite melting point.
(6) $^1H$ NMR spectrum (400 MHz, $CDCl_3$) δ(ppm): 2.20 (br d, 2-H), 2.68 (dd, 2-H), 3.77 (br d, 3-H), 3.08 (br d, 4-H), 3.53 (s, 4-$OCH_3$), 4.09 (br dd, 5-H), 1.89 (m, 8-H), 4.08 (dd, 9-H), 5.67 (dd, 10-H), 6.25 (dd, 11-H), 6.02 (br dd, 12-H), 5.59 (ddd, 13-H), 2.10 (dt, 14-H), 2.49 (br d, 14-H), 5.27 (ddq, 15-H), 1.29 (d, 16-$H_3$), 2.31 (br dd, 17-H), 2.86 (br dd, 17-H), 9.80 (br s, 18-H), 4.57 (d, 1'-H), 3.16 (dd, 2'-H), 2.39 (t, 3'-H), 3.45 (t, 4'-H), 3.25 (dq, 5'-H), 1.16 (d, 6'-$H_3$), 2.55 (s, 3'-N($CH_3$)$_2$), 4.87 (d, 1"-H), 1.54 (dd, 2"-Hax), 2.21 (d, 2"-Heq), 1.22 (s, 3"-$CH_3$), 2.76 (d, 4"-H), 4.40 (dq, 5"-H), 1.21 (d, 6"-$H_3$), 3.23 (s, 3"-$OCH_3$), 3.55 (dt, 4"-$OCH_2CH_2CH_2CH_3$), 3.60 (dt, 4"-$OCH_2CH_2CH_2CH_3$), 1.60 (m, 4"-$OCH_2CH_2CH_2CH_3$), 1.36 (m, 4"-$OCH_2CH_2CH_2CH_3$), 0.89 (t, 4"-$OCH_2CH_2CH_2CH_3$).

EXAMPLE 21

Process for producing compound (25) [a compound represented by the formula (X) wherein $R^5$ represents an n-pentyl group and $R^8$ represents a TBDMS group]:

To 200 mg of the compound (18) was added 3.0 ml of dry dimethylformamide to dissolve the compound and 38 mg of 60% oily sodium hydride was added thereto. The resulting mixture was stirred at room temperature. When bubbling was weakened, 1.14 g of n-pentyl iodide was added thereto and the obtained mixture was stirred at 45° C. for 30 minutes. Then the reaction mixture was cooled to room temperature. After slowly adding 100 ml of water, the reaction mixture was extracted with 100 ml of chloroform. One hundred ml of chloroform was added to the aqueous layer and extraction was carried out again. The chloroform layers were combined and washed with 100 ml portions of a saturated aqueous solution of sodium chloride twice. The chloroform layer was dried over anhydrous sodium sulfate and filtered. The filtrate was concentrated under reduced pressure and the residue thus obtained was purified by preparative TLC [developing system: hexane/ethyl acetate (2:1)]. Thus 164 mg of the compound (25) was obtained.

Physicochemical properties of the compound (25)
(1) Color and appearance: colorless solid.
(2) Molecular formula: $C_{58}H_{111}NO_{13}Si_3$.
(3) Mass spectrum (FDMS): m/z 1113 (M)+.
(4) Specific rotation: $[\alpha]_D^{26}$ −13° (c 1.0, $CH_3OH$).
(5) Melting at around 77° to 78° C. without showing any definite melting point.
(6) $^1H$ NMR spectrum (400 MHz, $CDCl_3$) δ(ppm): 2.38 (br dd, 2-H), 2.61 (dd, 2-H), 4.22 (m, 3-H), 3.37 (s, 4-$OCH_3$), 3.39 (br dd, 5-H), 0.40 (br dd, 7-H), 4.22 (m, 9-H), 5.74 (dd, 10-H), 6.11 (m, 11-H), 6.11 (m, 12-H), 5.61 (dt, 13-H), 4.83 (ddq, 15-H), 1.39 (dt, 17-H), 4.62 (br dd, 18-H), 4.17 (d, 1'-H), 3.43 (dd, 2'-H), 2.53 (t, 3'-H), 3.35 (t, 4'-H), 2.51 (s, 3'-N($CH_3$)$_2$), 5.03 (d, 1"-H), 1.76 (dd, 2"-Hax), 1.97 (br d, 2"Heq), 1.24 (s, 3"-$CH_3$), 2.70 (d, 4"-H), 4.22 (dq, 5"-H), 3.59 (dt, 4"-$OCH_2CH_2CH_2CH_3$).

EXAMPLE 22

Process for producing compound (26) [a compound represented by the formula (XI) wherein $R^4$ represents a methyl group, $R^5$ represents an n-pentyl group and $R^8$ represents a TBDMS group]:

To 148 mg of the compound (25) was added 7.5 ml of chloroform to dissolve the compound and 35 mg of m-chloroperbenzoic acid was added thereto, followed by stirring at room temperature for 5 minutes. Then the reaction mixture was dropped into 35 ml of a 10% aqueous solution of sodium thiosulfate and extracted with 70 ml of chloroform. The chloroform layer was successively washed with 70 ml portions of a saturated aqueous solution of sodium hydrogencarbonate twice and 70 ml portions of a saturated aqueous solution of sodium chloride twice. Then the organic layer was dried over anhydrous sodium sulfate and filtered. The filtrate was concentrated under reduced pressure. To 145 mg of the solid thus obtained was added 1.5 ml of dry dimethylformamide to dissolve the solid and 26 mg of 60% oily sodium hydride was added thereto. The resulting mixture was stirred at room temperature. When bubbling was weakened, 545 mg of methyl iodide was added thereto and the resulting mixture was stirred at 45° C. for 1 hour. Then the reaction mixture was cooled to room temperature. After slowly adding 35 ml of water, the reaction mixture was extracted with 75 ml of chloroform. Seventy-five ml of chloroform was added to the aqueous layer and extraction was carried out again. The chloroform layers were combined and washed with 150 ml portions of a saturated aqueous solution of sodium chloride twice. The chloroform layer was dried over anhydrous sodium sulfate and filtered. The filtrate was concentrated under reduced pressure and the residue thus obtained was charged on preparative TLC plate. After allowing the plate stand for 3 days, development was carried out for purification [developing system: chloroform/methanol (20:1)]. Thus 54 mg of the compound (26) was obtained.

Physicochemical properties of the compound (26)
(1) Color and appearance: colorless solid.
(2) Molecular formula: $C_{53}H_{99}NO_{13}Si_2$.
(3) Mass spectrum (SIMS): m/z 1014 (M+H)+.
(4) Specific rotation: $[\alpha]_D^{25}$ −2° (c 1.0, $CH_3OH$).
(5) Melting at around 63° to 64° C. without showing any definite melting point.
(6) $^1H$ NMR spectrum (400 MHz, $CDCl_3$) δ(ppm): 4.06 (br dt, 3-H), 3.44 (s, 4-$OCH_3$), 3.45 (dd, 5-H), 0.42 (br dd, 7-H), 4.18 (br d, 9-H), 5.73 (dd, 10-H), 6.10 (m, 11-H), 6.10 (m, 12-H), 5.62 (dt, 13-H), 4.80 (ddq, 15-H), 1.31 (d, 16-$H_3$), 1.43 (dt, 17-H), 1.66 (br d, 17-H), 4.57 (br dd, 18-H), 4.29 (d, 1'-H), 3.32 (dd, 2'-H), 2.47 (t, 3'-H), 3.36 (t, 4'-H), 2.55 (s, 3'-N($CH_3$)$_2$), 4.87 (d, 1"-H), 1.54 (dd, 2"-Hax), 2.22 (d, 2"-Heq), 1.22 (s, 3"-$CH_3$), 2.76 (d, 4"-H), 4.45 (dq, 5"-H), 3.25 (s, 3"-$OCH_3$), 3.54 (dt, 4"-$OCH_2CH_2CH_2CH_2CH_3$), 3.60 (dt, 4"-$OCH_2CH_2CH_2CH_2CH_3$).

EXAMPLE 23

Process for producing compound (11) [a compound represented by the formula (I) wherein $R^1$ represents a hydrogen atom, $R^2$ represents a hydrogen atom, $R^3$ represents a hydrogen atom, $R^4$ represents a methyl group and $R^5$ represents an n-pentyl group]:

To 50 mg of the compound (26) was added 400 μl of a 2M solution of tetra-n-butylammonium fluoride in tetrahydrofuran and the mixture was allowed to react at 45° C. for 1 hour. Then the reaction mixture was cooled to room temperature, dropped into 4.0 ml of a 5% aqueous solution of potassium hydrogensulfate and then extracted with 25 ml portions of chloroform twice. The chloroform layers were combined and successively washed with 50 ml portions of a saturated aqueous solution of sodium hydrogencarbonate twice and 50 ml portions of a saturated aqueous solution of sodium chloride twice. The organic layer was dried over anhydrous sodium sulfate and filtered. The filtrate was concentrated under reduced pressure and the residue thus obtained was purified by silica gel column-chromatography [10 g: chloroform/methanol (50:1)]. Thus 23 mg of the compound (11) was obtained.

Physicochemical properties of the compound (11)
(1) Color and appearance: colorless solid.
(2) Molecular formula: $C_{41}H_{71}NO_{13}$.
(3) Mass spectrum (SIMS): m/z 786 (M+H)+.
(4) Specific rotation: $[\alpha]_D^{24}$ −55° (c 1.0 $CH_3OH$).
(5) Melting at around 76° to 78° without showing any definite melting point.
(6) $^1H$ NMR spectrum (400 MHz, CDCl) δ(ppm): 2.19 (br d, 2-H), 2.68 (dd, 2-H), 3.77 (br d, 3-H), 3.07 (br d, 4-H), 3.52 (s, 4-$OCH_3$), 4.08 (br dd, 5-H), 1.88 (m, 8-H), 4.07 (dd, 9-H), 5.66 (dd, 10-H), 6.24 (dd, 11-H), 6.01 (br dd, 12-H), 5.58 (ddd, 13-H), 2.10 (dt, 14-H), 2,48 (br d, 14-H), 5.27 (ddq, 15-H), 1.28 (d, 16-$H_3$), 2.31 (br dd, 17-H), 9.80 (br s, 18-H) 0.99 (d, 19-$H_3$), 4.57 (d, 1'-H), 3.16 (dd, 2'-H), 2'-H), 2.40 (t, 3'-H), 3.45 (t, 4'-H), 3.25 (dq, 5'-H), 1.15 (d, 6'-$H_3$), 2.56 (s, 3'-$N(CH_3)_2$), 4.86 (d, 1''-H), 1.54 (dd, 2''-Hax), 2.20 (d, 2''-Heq), 1.22 (s, 3''-$CH_3$), 2.75 (d, 4''-H), 439 (dq, 5''-H), 1.20 (d, 6''-$H_3$), 3.23 (s, 3''-$OCH_3$), 3.54 (dt, 4''-$OCH_2CH_2CH_2CH_2CH_3$), 3.58 (dt, 4''-$OCH_2CH_2CH_2CH_2CH_3$) 0.87 (br t, 4''-$OCH_2CH_2CH_2CH_2CH_3$).

EXAMPLE 24

Process for producing compound (27) [a compound represented by the formula (X) wherein $R^5$ represents an isoamyl group and $R^5$ represents a TBDMS group]:

Fifteen ml of dry dimethylformamide was added to 1.00 g of the compound (18) to dissolve the compound therein and 192 mg of 60% oily sodium hydride was added thereto. The resulting mixture was stirred at room temperature. When bubbling was weakened, 5.70 g of isoamyl iodide was added thereto and the resulting mixture was stirred at 45° C. for 1 hour. Then the reaction mixture was cooled to room temperature. After slowly adding 250 ml of water, the reaction mixture was extracted with 250 ml of chloroform. Two hundred fifty ml of chloroform was added to the aqueous layer and extraction was carried out again. The chloroform layers were combined and washed with 500 ml portions of a saturated aqueous solution of sodium chloride twice. The chloroform layer was dried over anhydrous sodium sulfate and filtered. The filtrate was concentrated under reduced pressure and the residue thus obtained was purified by silica gel column chromatography [150 g: hexane/ethyl acetate (2: 1)]. Thus 715 mg of the compound (27) was obtained.

Physicochemical properties of the compound (27)
(1) Color and appearance: colorless solid.
(2) Molecular formula: $C_{58}H_{111}NO_{13}Si_3$.
(3) Mass spectrum (FDMS): m/z 1113 (M)+.
(4) Specific rotation: $[\alpha]_D^{25}$ −13° (c 1.0, $CH_3OH$).
(5) Melting at around 84° to 86° C. without showing any definite melting point.

(6) $^1H$ NMR spectrum (400 MHz, $CDCl_3$) δ(ppm): 2.37 (br dd, 2-H), 2.59 (dd, 2-H), 4.20 (m, 3-H), 3.36 (s, 4-$OCH_3$), 3.38 (br dd, 5-H), 0.38 (br dd, 7-H), 4.20 (m, 9-H), 5.73 (dd, 10-H), 6.10 (m, 11-H), 6.10 (m, 12-H), 5.60 (dt, 13-H), 4.81 (ddq, 15-H), 1.38 (dt, 17-H), 1.62 (br d, 17-H), 4.60 (br dd, 18-H), 4.16 (d, 1'-H), 3.42 (dd, 2'-H), 2.52 (t, 3'-H), 3.34 (t, 4'-H), 2.50 (s, 3'-$N(CH_3)_2$), 5.01 (d, 1''-H), 1.74 (dd, 2''-Hax), 1.95 (br d, 2''-Heq), 1.23 (s, 3''-$CH_3$), 2.69 (d, 4''-H), 4.20 (dq, 5''-H), 3.59 (dt, 4''-$OCH_2CH_2CH(CH_3)_2$)2), 3.63 (dt, 4''-$OCH_2CH_2CH(CH_3)_2$), 1.49 (m, 4''-$OCH_2CH_2CH(CH_3)_2$), 1.68 (m, 4''-$OCH_2CH_2CH(CH_3)_2$).

EXAMPLE 25

Process (1) for producing compound (28) [a compound represented by the formula (XI) wherein $R^4$ represents a methyl group, $R^5$ represents an isoamyl group and $R^8$ represents a TBDMS group]:

Seventy-one ml of chloroform was added to 1.42 g of the compound (27) to dissolve the compound therein and 328 mg of m-chloroperbenzoic acid was added thereto, followed by stirring at room temperature for 5 minutes. Then the reaction mixture was dropped into 150 ml of a 10% aqueous solution of sodium thiosulfate and extracted with 500 ml of chloroform. The chloroform layer was successively washed with 500 ml portions of a saturated aqueous solution of sodium hydrogencarbonate twice and 500 ml portions of a saturated aqueous solution of sodium chloride twice. Then the organic layer was dried over anhydrous sodium sulfate and filtered. The filtrate was concentrated under reduced pressure. Fourteen ml of dry dimethylformamide was added to 1.42 g of the solid thus obtained to dissolve the solid therein and 251 mg of 60% oily sodium hydride was added thereto. The resulting mixture was stirred at room temperature. When bubbling was weakened, 5.39 g of methyl iodide was added thereto and the resulting mixture was stirred at 45° C. for 1 hour. Then the reaction mixture was cooled to room temperature. After slowly adding 500 ml of water, the reaction mixture was extracted with 500 ml of chloroform. Five hundred ml of chloroform was added to the aqueous layer and extraction was carried out again. The chloroform layers were combined and washed with 500 ml portions of a saturated aqueous solution of sodium chloride twice. The chloroform layer was dried over anhydrous sodium sulfate and filtered. The filtrate was concentrated under reduced pressure and thus 1.55 g of an oily product was obtained. A 190 mg portion of this oily product was dissolved in 12 ml of methanol and adsorbed by 16.0 g of silica gel. After distilling off the methanol under reduced pressure, the residue was allowed to stand overnight. Then the substance adsorbed by the silica gel was extracted with a solvent mixture [chloroform/methanol (5:1)] and the solvent was distilled off under reduced pressure. The residue thus obtained was purified by silica gel column chromatography [12 g: chloroform/methanol (50:1)]. Thus 103 mg of the compound (28) was obtained.

Physicochemical properties of the compound (28)
(1) Color and appearance: colorless solid.
(2) Molecular formula: $C_{53}H_{99}NO_{13}Si_2$.
(3) Mass spectrum (SIMS): m/z 1014 (M+H)+.
(4) Specific rotation: $[\alpha]_D^{25}$ −2° (c 1.0, $CH_3OH$).
(5) Melting at around 68° to 70° C. without showing any definite melting point.
(6) $^1H$ NMR spectrum (400 MHz, $CDCl_3$) δ(ppm): 2.42 (dd, 2-H), 4.05 (br dt, 3-H), 3.44 (s, 4-$OCH_3$), 3.46

(dd, 5-H), 0.42 (br dd, 7-H), 4.18 (br d, 9-H), 5.73 (dd, 10-H), 6.10 (m, 11-H), 6.10 (m, 12-H), 5.62 (dt, 13-H), 4.80 (ddq, 15-H), 1.31 (d, 16-$H_3$), 1.43 (dt, 17-H), 1.66 (br d, 17-H), 4.57 (br dd, 18-H), 4.30 (d, 1'-H), 3.32 (dd, 2'-H), 2.46 (t, 3'-H), 3.36 (t, 4'-H), 2.55 (s, 3'-N($CH_3$)$_2$), 4.87 (d, 1''-H), 1.54 (dd, 2''-Hax), 2.21 (d, 2''-Heq), 1.22 (s, 3''-$CH_3$), 2.76 (d, 4''-H), 4.45 (dq, 5''-H), 3.25 (s, 3''-O$CH_3$), 3.57 (dt, 4''O$CH_2$$CH_2$CH($CH_3$)$_2$), 3.63 (dt, 4''-O$CH_2$$CH_2$CH($CH_3$)$_2$).

EXAMPLE 26

Process (2) for producing compound (28) [a compound represented by the formula (XI) wherein $R^4$ represents a methyl group, $R^5$ represents an isoamyl group and $R^8$ represents a TBDMS group]:

Seventy-one ml of chloroform was added to 1.42 g of the compound (27) to dissolve the compound therein and 328 mg of m-chloroperbenzoic acid was added thereto, followed by stirring at room temperature for 5 minutes. Then the reaction mixture was dropped into 150 ml of a 10% aqueous solution of sodium thiosulfate and extracted with 500 ml of chloroform. The chloroform layer was successively washed with 500 ml portions of a saturated aqueous solution of sodium hydrogencarbonate twice and 500 ml portions of a saturated aqueous solution of sodium chloride twice. Then the organic layer was dried over anhydrous sodium sulfate and filtered. The filtrate was concentrated under reduced pressure. Fourteen ml of dry dimethylformamide was added to 1.42 g of the solid thus obtained to dissolve the solid therein and 251 mg of 60% oily sodium hydride was added thereto. The resulting mixture was stirred at room temperature. When bubbling was weakened, 5.39 g of methyl iodide was added thereto and the obtained mixture was stirred at 45° C. for 1 hour. Then the reaction mixture was cooled to room temperature. After slowly adding 500 ml of water, the reaction mixture was extracted with 500 ml of chloroform. Five hundred ml of chloroform was added to the aqueous layer and extraction was carried out again. The chloroform layers were combined and washed with 500 ml portions of a saturated aqueous solution of sodium chloride twice. The chloroform layer was dried over anhydrous sodium sulfate and filtered. The filtrate was concentrated under reduced pressure and thus 1.55 g of an oily product was obtained. To a 190 mg portion of this oily product were successively added 19 ml of methanol and 19 ml of 0.025N hydrochloric acid to thereby dissolve the oily product, followed by reacting at 45° C. for 2 hours. After cooling to room temperature, the reaction mixture was dropped into 150 ml of a saturated aqueous solution of sodium hydrogencarbonate and extracted with 150 ml portions of chloroform twice. The chloroform layers were combined and washed with 300 ml portions of a saturated aqueous solution of sodium chloride twice. Then the organic layer was dried over anhydrous sodium sulfate and filtered. The filtrate was concentrated under reduced pressure and the residue thus obtained was purified by preparative TLC [developing system: chloroform/methanol (30:1)]. Thus 98 mg of the compound (28) was obtained.

EXAMPLE 27

Process (2) for producing compound (12) [a compound represented by the formula (I) wherein $R^1$ represents a hydrogen atom, $R^2$ represents a hydrogen atom $R^3$ represents a hydrogen atom, $R^4$ represents a methyl group and $R^5$ represents an isoamyl group]:

To 1.07 g of the compound (28) was added 8.4 ml of a 2M solution of tetra-n-butylammonium fluoride in tetrahydrofuran and the mixture was allowed to react at 45° C. for 1 hour. Then the reaction mixture was cooled to room temperature, dropped into 50 ml of a 5% aqueous solution of potassium hydrogensulfate and then extracted with 300 ml portions of chloroform twice. The chloroform layers were combined and successively washed with 600 ml portions of a saturated aqueous solution of sodium hydrogencarbonate twice and 600 ml portions of a saturated aqueous solution of sodium chloride twice. The organic layer was dried over anhydrous sodium sulfate and filtered. The filtrate was concentrated under reduced pressure and the residue thus obtained was purified by silica gel column chromatography [100 g: chloroform/methanol (50:1)]. Thus 380 mg of the compound (12) was obtained.

Physicochemical properties of the compound (12) obtained by chemical synthesis:

(1) Specific rotation: $[\alpha]_D^{26}$ −71° (c 1.0, $CH_3OH$).

(2) Melting at around 101° to 106° C. without showing any definite melting point.

EXAMPLE 28

Process for producing compound (29) [a compound represented by the formula (XI) wherein $R^4$ represents an ethyl group, $R^5$ represents an isoamyl group and $R^8$ represents a TBDMS group]:

To 190 mg of the compound (27) was added 1.0 ml of dry dimethylformamide to dissolve the compound and 34 mg of 60% oily sodium hydride was added thereto. The resulting mixture was stirred at room temperature. When bubbling was weakened, 796 mg of ethyl iodide was added thereto and the resulting mixture was stirred at 45° C. for 3 hours. Then the reaction mixture was cooled to room temperature. After slowly adding 100 ml of water, the reaction mixture was extracted with 100 ml of chloroform. One hundred ml of chloroform was added to the aqueous layer and extraction was carried out again. The chloroform layers were combined and washed with 100 ml portions of a saturated aqueous solution of sodium chloride twice. The chloroform layer was dried over anhydrous sodium sulfate and filtered. The filtrate was concentrated under reduced pressure and thus 114 mg of crude 9,18,2'-tri-O-TBDMS-3''-O-ethyl-4''-O-isoamylleucomycin V-3,18-acetal was obtained. This product was dissolved in 5.7 ml of chloroform and 26 mg of m-chloroperbenzoic acid was added thereto, followed by stirring at room temperature for 5 minutes. The reaction mixture was dropped into 30 ml of a 10% aqueous solution of sodium thiosulfate and extracted with 60 ml of chloroform. The chloroform layer was washed successively with 60 ml portions of a saturated aqueous solution of sodium hydrogencarbonate twice and 60 ml portions of a saturated aqueous solution of sodium chloride twice. Then the organic layer was dried over anhydrous sodium sulfate and filtered. The filtrate was concentrated under reduced pressure and the resulting residue was charged on preparative TLC plate. After allowing the plate stand for 3 days, development was carried out for purification [developing system: chloroform/methanol (20:1)]. Thus 56 mg of the compound (29) was obtained.

Physicochemical properties of the compound (29)

(1) Color and appearance: colorless solid.

(2) Molecular formula: $C_{54}H_{101}NO_{13}Si_2$.

(3) Mass spectrum (FDMS): m/z 1028 (M+H)$^+$.

(4) Specific rotation: $[\alpha]_D^{26}$ −11° (c 1.0, $CH_3OH$).

(5) m.p.: 66°–67° C.

(6) $^1$H NMR spectrum (400 MHz, CDCl$_3$) δ(ppm): 2.41 (dd, 2-H), 4.05 (br dt, 3-H), 3.44 (s, 4-OCH$_3$), 0.42 (br dd, 7-H), 4.19 (br d, 9-H), 5.73 (dd, 10-H), 6.10 (m, 11-H), 6.10 (m, 12-H), 5.62 (dt, 13-H), 4.80 (ddq, 15-H), 1.31 (d, 16-H$_3$), 1.44 (dt, 17-H), 1.66 (br d, 17-H), 4.57 (br dd, 18-H), 4.29 (d, 1'-H), 3.33 (dd, 2'-H), 2.45 (t, 3'-H), 3.31 (t, 4'-H), 3.24 (dq, 5'-H), 2.55 (s, 3'-N(CH$_3$)$_2$), 4.84 (d, 1''-H), 154 (dd, 2''-Hax), 2.21 (d, 2''-Heq), 1.23 (s, 3''-CH$_3$), 2.74 (d, 4''-H), 4.46 (dq, 5''-H), 3.45 (dq, 3''-OCH$_2$CH$_3$), 3.50 (dq, 3''-OCH$_2$CH$_3$), 1.14 (t, 3''-OCH$_2$C$\underline{H}$$_3$), 3.54 (dt, 4''-OC$\underline{H}$$_2$CH$_2$CH(CH$_3$)$_2$), 3.66 (dt, 4''-OC$\underline{H}$$_2$CH$_2$CH(CH$_3$)$_2$).

EXAMPLE 29

Process for producing compound (14) [a compound represented by the formula (I) wherein R$^1$ represents a hydrogen atom, R$^2$ represents a hydrogen atom, R$^3$ represents a hydrogen atom, R$^4$ represents an ethyl group and R$^5$ represents an isoamyl group]:

To 56 mg of the compound (29) was added 430 μl of a 2M solution of tetra-n-butylammonium fluoride in tetrahydrofuran and the mixture was allowed to react at 45° C. for 1 hour. Then the reaction mixture was cooled to room temperature, dropped into 4.3 ml of a 5% aqueous solution of potassium hydrogensulfate and then extracted with 25 ml portions of chloroform twice. The chloroform layers were combined and successively washed with 50 ml portions of a saturated aqueous solution of sodium hydrogencarbonate twice and 50 ml portions of a saturated aqueous solution of sodium chloride twice. The organic layer was dried over anhydrous sodium sulfate and filtered. The filtrate was concentrated under reduced pressure and the residue thus obtained was purified by silica gel column chromatography [10 g: chloroform/methanol (30:1)]. Thus 23 mg of the compound (14) was obtained.

Physicochemical properties of the compound (14)

(1) Color and appearance: colorless solid.

(2) Molecular formula: C$_{42}$H$_{73}$NO$_{13}$.

(3) Mass spectrum (EIMS): m/z 799 (M)$^+$.

(4) Specific rotation: [α]$_D$$^{26}$ −70° (c 1.0, CH$_3$OH).

(5) Melting at around 98° to 100° C. without showing any definite melting point.

(6) $^1$H NMR spectrum (400 MHz, CDCl$_3$) δ(ppm): 2.20 (br d, 2-H), 2.69 (dd, 2-H), 3.77 (br d, 3-H), 3.08 (br d, 4-H), 3.53 (s, 4-OCH$_3$), 4.09 (br dd, 5-H), 1.88 (m, 8-H), 4.08 (dd, 9-H), 5.66 (dd, 10-H), 6.25 (dd, 11-H), 6.01 (br dd, 12-H), 5.59 (ddd, 13-H), 2.10 (dt, 14-H), 2.49 (br d, 14-H), 5.27 (ddq, 15-H), 1.29 (d, 16-H$_3$), 2.31 (br dd, 17-H), 2.86 (br dd, 17-H), 9.80 (br s, 18-H), 0.97 (d, 19-H$_3$), 4.56 (d, 1'-H), 3.16 (dd, 2'-H), 2.38 (t, 3'-H), 3.40 (t, 4'-H), 3.24 (dq, 5'-H), 1.15 (d, 6'-H$_3$), 2.55 (s, 3'-N(CH$_3$)$_2$), 4.83 (d, 1''-H), 1.55 (dd, 2''-Hax), 2.20 (d, 2''-Heq), 1.22 (s, 3''-CH$_3$), 2.73 (d, 4''-H), 4.41 (dq, 5''-H), 1.21 (d, 6''-H$_3$), 3.42 (dq, 3''-OCH$_2$CH$_3$), 3.47 (dq, 3''-OCH$_2$CH$_3$), 1.11 (t, 3''-OCH$_2$C$\underline{H}$$_3$), 3.56 (dt, 4''-OC$\underline{H}$$_2$CH$_2$CH(CH$_3$)$_2$), 3.64 (dt, 4''-OC$\underline{H}$$_2$CH$_2$CH(CH$_3$)$_2$), 1.49 (m, 4''-OC$\underline{H}$$_2$CH$_2$CH(CH$_3$)$_2$), 2), 1.65 (m, 4''-OCH$_2$C$\underline{H}$$_2$CH(CH$_3$)$_2$), 0.87 (d, 4''-OCH$_2$CH$_2$C$\underline{H}$(CH$_3$)$_2$).

EXAMPLE 30

Process for producing compound (30) [a compound represented by the formula (XI) wherein R$^4$ represents an n-propyl group, R$^5$ represents an isoamyl group and R$^8$ represents a TBDMS group]:

To 410 mg of the compound (27) was added 820 μl of dry dimethylformamide to dissolve the compound and 74 mg of 60% oily sodium hydride was added thereto. The resulting mixture was stirred at room temperature. When bubbling was weakened, 1.88 g of n-propyl iodide was added thereto and the resulting mixture was stirred at 45° C. for 4 hours. Then the reaction mixture was cooled to room temperature. After slowly adding 200 ml of water, the reaction mixture was extracted with 200 ml of chloroform. Two hundred ml of chloroform was added to the aqueous layer and extraction was carried out again. The chloroform layers were combined and washed with 400 ml portions of a saturated aqueous solution of sodium chloride twice. The chloroform layer was dried over anhydrous sodium sulfate and filtered. The filtrate was concentrated under reduced pressure and 420 mg of the solid thus obtained was purified by preparative TLC [developing system: hexane/ethyl acetate (4:1)]. Thus 147 mg of 9,18,2'-tri-O-TBDMS-4''-O-isoamyl-3''-O-n-propylleucomycin V-3,18-acetal was obtained. This product was dissolved in 6.5 ml of chloroform and 24 mg of m-chloroperbenzoic acid was added thereto, followed by stirring at room temperature for 5 minutes. The reaction mixture was dropped into 25 ml of a 10% aqueous solution of sodium thiosulfate and extracted with 100 ml of chloroform. The chloroform layer was washed successively with 100 ml portions of a saturated aqueous solution of sodium hydrogencarbonate twice and 100 ml portions of a saturated aqueous solution of sodium chloride twice. Then the organic layer was dried over anhydrous sodium sulfate and filtered. The filtrate was concentrated under reduced pressure and the resulting residue was charged on preparative TLC plate. After allowing the plate stand for 3 days, development was carried out for purification [developing system: chloroform/methanol (20:1)]. Thus 81 mg of the compound (30) was obtained.

Physicochemical properties of the compound (30)

(1) Color and appearance: colorless solid.

(2) Molecular formula: C$_{55}$H$_{103}$NO$_{13}$Si$_2$.

(3) Mass spectrum (FDMS): m/z 1042 (M+H)$^+$.

(4) Specific rotation: [α]$_D$$^{24}$ −17° (c 1.0, CHCl$_3$).

(5) Melting at around 57 to 63° C. without showing any definite melting point.

(6) $^1$H NMR spectrum (400 MHz, CDCl$_3$) δ(ppm): 2.43 (dd, 2-H), 4.07 (br d, 3-H), 3.27 (br d, 4-H), 3.46 (s, 4-OCH$_3$), 3.48 (br dd, 5-H), 4.21 (dd, 9-H), 5.75 (dd, 10-H), 6.12 (m, 11-H), 6.12 (m, 12-H), 5.64 (ddd, 13-H), 4.83 (ddq, 15-H), 1.33 (d, 16-H$_3$), 1.49 (br dd, 17-H), 4.59 (br s, 18-H), 4.31 (d, 1'-H), 3.36 (dd, 2'-H), 2.48 (t, 3'-H), 3.25 (dq, 5'-H), 2.58 (s, 3'-N(CH$_3$)$_2$), 4.85 (d, 1''-H), 1.57 (dd, 2''-Hax), 2.21 (d, 2''-Heq), 1.24 (s, 3''-CH$_3$), 2.77 (d, 4''-H), 4.46 (dq, 5''-H), 1.22 (d, 6''-H$_3$), 3.42 (dt, 3''-OCH$\underline{H}$CH$_2$CH$_3$), 0.88 (t, 3''-OCH$_2$CH$_2$CH$_3$), 3.59 (dt, 4''-OC$\underline{H}$$_2$CH$_2$CH(CH$_3$)$_2$), 3.68 (dt, 4''-OCH$_2$C$\underline{H}$(CH$_3$)$_2$) 0.90 (d, 4''-OCH$_2$CH$_2$CH(CH$_3$)$_2$).

EXAMPLE 31

Process for producing compound (15) [a compound represented by the formula (I) wherein R$^1$ represents a hydrogen atom, R$^2$ represents a hydrogen atom, R$^3$ represents a hydrogen atom, R$^4$ represents an n-propyl group and R$^5$ represents an isoamyl group]:

To 37 mg of the compound (30) was added 280 μl of a 2M solution of tetra-n-butylammonium fluoride in tetrahydrofuran and the mixture was allowed to react at 45° C. for 1 hour. Then the reaction mixture was cooled to room temperature, dropped into 3 ml of a 5% aqueous solution of potassium hydrogensulfate and then extracted with 20 ml portions of chloroform twice. The chloroform layers were combined and successively washed with 50 ml portions of a saturated aqueous solution of sodium hydrogencarbonate twice and 50 ml portions of a saturated aqueous solution of sodium chloride twice. The organic layer was dried over anhydrous sodium sulfate and filtered. The filtrate was concentrated under reduced pressure and the residue thus obtained was purified by silica gel column chromatography [6.0 g: chloroform/methanol (50:1)]. Thus 9.8 mg of the compound (15) was obtained.

Physicochemical properties of the compound (15)

(1) Color and appearance: colorless solid.

(2) Molecular formula: $C_{43}H_{75}NO_{13}$.

(3) Mass spectrum (SIMS): m/z 814 (M+H)+.

(4) Specific rotation: $[\alpha]_D^{24}$ −73° (c 1.0, $CH_3OH$).

(5) Melting at around 88° to 93° C. without showing any definite melting point.

(6) $^1H$ NMR spectrum (400 MHz, $CDCl_3$) δ(ppm): 2.22 (br d, 2-H), 2.70 (dd, 2-H), 3.79 (br d, 3-H), 3.10 (br d, 4-H), 3.55 (s, 4-$OCH_3$), 4.10 (br dd, 5-H), 1.91 (m, 8-H), 4.11 (dd, 9-H), 5.68 (dd, 10-H), 6.26 (dd, 11-H), 6.04 (br dd, 12-H), 5.61 (ddd, 13-H), 2.12 (dt, 14-H), 2.51 (br d, 14-H), 5.29 (ddq, 15-H), 1.30 (d, 16-$H_3$), 2.33 (br dd, 17-H), 2.88 (br dd, 17-H), 9.80 (br s, 18-H), 0.98 (d, 19-$H_3$), 4.58 (d, 1'-H), 3.18 (dd, 2'-H), 2.40 (t, 3'-H), 3.41 (t, 4'-H), 3.26 (dq, 5'-H), 1.17 (d, 6'-$H_3$), 2.56 (s, 3'-$N(CH_3)_2$), 4.84 (d, 1''-H), 1.57 (dd, 2''-Hax), 2.21 (d, 2''-Heq), 1.23 (s, 3''-$CH_3$), 2.76 (d, 4''-H), 4.41 (dq, 5''-H), 1.22 (d, 6''-H), 3.28 (dt, 3''-$OCH_2CH_3$), 3.39 (dt, 3''-$OCH_2CH_2CH_3$), 0.87 (t, 3'-$OCH_2\overline{CH}_2CH_3$), 3.58 (dt, 4''-$O\overline{CH}_2CH_2CH(CH_3)_2$), 3.66 (dt, 4''$O\overline{CH}_2CH_2CH(CH_3)_2$), 1.68 (m, 4''-$OCH_2\overline{CH}_2CH(CH_3)_2$), 0.89 (d, 4''-$OCH_2CH_2C\overline{H}(CH_3)_2$).

EXAMPLE 32

Process for producing compound (31) [a compound represented by the formula (XI) wherein $R^4$ represents a methyl group, $R^5$ represents a methyl group and $R^8$ represents a TBDMS group]:

Ten ml of chloroform was added to 200 mg of the compound (18) to dissolve the compound therein and 50 mg of m-chloroperbenzoic acid was added thereto, followed by stirring at room temperature for 5 minutes. Then the reaction mixture was dropped into 50 ml of a 10% aqueous solution of sodium thiosulfate and extracted with 100 ml of chloroform. The chloroform layer was successively washed with 100 ml portions of a saturated aqueous solution of sodium hydrogencarbonate twice and 100 ml portions of a saturated aqueous solution of sodium chloride twice. Then the organic layer was dried over anhydrous sodium sulfate and filtered. The filtrate was concentrated under reduced pressure. To 200 mg of the solid thus obtained was added 2.0 ml of dry dimethylformamide to dissolve the solid and 60 mg of 60% oily sodium hydride was added thereto. The resulting mixture was stirred at room temperature. When bubbling was weakened, 1.2 g of methyl iodide wax added thereto and the resulting mixture was stirred at 45° C. for 1 hour. Then the reaction mixture was cooled to room temperature. After slowly adding 100 ml of water, the reaction mixture was extracted with 100 ml of chloroform. One hundred ml of chloroform was added to the aqueous layer and extraction was carried out again. The chloroform layers were combined and washed with 100 ml portions of a saturated aqueous solution of sodium chloride twice. The chloroform layer was dried over anhydrous sodium sulfate and filtered. The filtrate was concentrated under reduced pressure and the residue thus obtained was charged on preparative TLC plate. After allowing the plate stand for 2 days, development was carried out for purification [developing system: chloroform/methanol (20:1)]. Thus 55 mg of the compound (31) was obtained.

Physicochemical properties of the compound (31)

(1) Color and appearance: colorless solid.

(2) Molecular formula: $C_{49}H_{91}NO_{13}Si_2$.

(3) Mass spectrum (FDMS): m/z 958 (M+H)+.

(4) Specific rotation: $[\alpha]_D^{26}$ −4° (c 1.0, $CH_3OH$).

(5) m.p.: 76° C.

(6) $^1H$ NMR spectrum (400 MHz, $CDCl_3$) δ(ppm): 4.05 (br dt, 3-H), 3.44 (s, 4-$OCH_3$), 3.46 (br d, 5-H), 0.41 (br dd, 7-H), 4.18 (br d, 9-H), 5.72 (dd, 10-H), 6.10 (m, 11-H), 6.10 (m, 12-H), 5.62 (dt, 13-H), 4.80 (ddq, 15-H), 1.30 (d, 16-$H_3$), 1.43 (dt, 17-H), 1.66 (br d, 17-H), 4.57 (br dd, 18-H), 4.30 (d, 1'-H), 3.33 (dd, 2'-H), 2.46 (t, 3'-H), 3.36 (t, 4'-H), 2.55 (s, 3'-$N(CH_3)_2$), 4.87 (d, 1''-H), 1.52 (dd, 2''-Hax), 2.22 (d, 2''-Heq), 1.23 (s, 3''-$CH_3$), 2.66 (d, 4''-H), 4.44 (dq, 5''-H), 3.24 (s, 3''-$OCH_3$), 3.53 (s, 4''-$OCH_3$).

EXAMPLE 33

Process for producing compound (7) [a compound represented by the formula (I) wherein $R^1$ represents a hydrogen atom, $R^2$ represents a hydrogen atom, $R^3$ represents a hydrogen atom, $R^4$ represents a methyl group and $R^5$ represents a methyl group]:

To 55 mg of the compound (31) was added 460 μof a 2M solution of tetra-n-butylammonium fluoride in tetrahydrofuran and the mixture was allowed to react at 45° C. for 1 hour. Then the reaction mixture was cooled to room temperature, dropped into 4.6 ml of a 5% aqueous solution of potassium hydrogensulfate and then extracted with 25 ml portions of chloroform twice. The chloroform layers were combined and successively washed with 50 ml portions of a saturated aqueous solution of sodium hydrogencarbonate twice and 50 ml portions of a saturated aqueous solution of sodium chloride twice. The organic layer was dried over anhydrous sodium sulfate and filtered. The filtrate was concentrated under reduced pressure and the residue thus obtained was purified by silica gel column chromatography [10 g: chloroform/methanol (50:1)]. Thus 12 mg of the compound (7) was obtained.

Physicochemical properties of the compound (7)

(1) Color and appearance: colorless solid.

(2) Molecular formula: $C_{37}H_{63}NO_{13}$.

(3) Mass spectrum (SIMS): m/z 730 (M+H)+.

(4) Specific rotation: $[\alpha]_D^{25}$ −53° (c 1.0, $CH_3OH$).

(5) Melting at around 99° to 101° C. without showing any definite melting point.

(6) $^1H$ NMR spectrum (400 MHz, $CDCl_3$) δ(ppm): 2.20 (br d, 2-H), 2.68 (dd, 2-H), 3.77 (br d, 3-H), 3.08 (br d, 4-H), 3.52 (s, 4-$OCH_3$), 4.09 (br dd, 5-H), 1.87 (m, 8-H), 4.08 (dd, 9-H), 5.66 (dd, 10-H), 6.25 (dd, 11-H), 6.02 (br dd, 12-H), 5.59 (ddd, 13-H), 2.10 (dt, 14-H), 2.49 (br d, 14-H), 5.27 (ddq, 15-H), 1.29 (d, 16-$H_3$), 2.31 (br dd, 17-H), 2.85 (br dd, 17-H), 9.80 (br s, 18-H), 4.57 (d, 1'-H), 2.40 (t, 3'-H), 3.46 (t, 4'-H), 3.24 (dq, 5'-H), 1.16 (d, 6'-$H_3$), 2.57 (s, 3'-$N(CH_3)_2$), 4.88 (d, 1''-H), 1.53 (dd, 2''-Hax), 2.22 (d, 2''Heq), 1.22 (s, 3''-$CH_3$), 2.66 (d, 4''-H), 4.37 (dq, 5''-H), 1.21 (d, 6''-$H_3$), 3.22 (s, 3''-$OCH_3$) 3.52 (s, 4''-$OCH_3$).

EXAMPLE 34

Process (3) for producing compound (12) [a compound represented by the formula (I) wherein $R^1$ represents a hydrogen atom, $R^2$ represents a hydrogen atom, $R^3$ represents a hydrogen atom, $R^4$ represents a methyl group and $R^5$ represents an isoamyl group]:

Seventy-one ml of chloroform was added to 1.42 g of the compound (27) to dissolve the compound therein and 328 mg of m-chloroperbenzoic acid was added thereto, followed by stirring at room temperature for 5 minutes. Then the reaction mixture was dropped into 150 ml of a 10% aqueous solution of sodium thiosulfate and extracted with 500 ml of chloroform. The chloroform layer was successively washed with 500 ml portions of a saturated aqueous solution of sodium hydrogencarbonate twice and 500 ml portions of a saturated aqueous solution of sodium chloride twice. Then the organic layer was dried over anhydrous sodium sulfate and filtered. The filtrate was concentrated under reduced pressure. Fourteen ml of dry dimethylformamide was added to 1.42 g of the solid thus obtained to dissolve the solid and 251 mg of 60% oily sodium hydride was added thereto. The resulting mixture was stirred at room temperature. When bubbling was weakened, 5.39 g of methyl iodide was added thereto and the resulting mixture was stirred at 45° C. for 1 hour. Then the reaction mixture was cooled to room temperature. After slowly adding 500 ml of water, the reaction mixture was extracted with 500 ml of chloroform. Five hundred ml of chloroform was added to the aqueous layer and extraction was carried out again. The chloroform layers were combined and washed with 500 ml portions of a saturated aqueous solution of sodium chloride twice. The chloroform layer was dried over anhydrous sodium sulfate and filtered. The filtrate was concentrated under reduced pressure and thus 1.55 g of an oily product was obtained. To a 38 mg portion of this oily product was successively added 2.7 ml of acetonitrile and 2.7 ml of 0.025N hydrochloric acid to dissolve the oily product and the resulting mixture was allowed to react at 45° C. for 4 hours. After cooling to room temperature, the reaction mixture was dropped into 25 ml of a saturated aqueous solution of sodium hydrogencarbonate and extracted with 25 ml portions of chloroform twice. The chloroform layers were combined and washed with 50 ml portions of a saturated aqueous solution of sodium chloride twice. Then the organic layer was dried over anhydrous sodium sulfate and filtered. The filtrate was concentrated under reduced pressure and the residue thus obtained was purified by preparative TLC [developing system: hexane/acetone/chloroform/methanol/conc. aqueous ammonia (4: 4:5:1:0.1)]. Thus 10 mg of the compound (12) was obtained.

EXAMPLE 35

Process (2) for producing compound (3) [a compound represented by the formula (I) wherein $R^1$ represents a propionyl group, $R^2$ represents a hydrogen atom, $R^3$ represents a hydrogen atom, $R^4$ represents a methyl group and $R^5$ represents an isoamyl group]:

The same medium as described in Example 1 was pipetted in 80 ml portions into three 500 ml-Erlenmeyer's flasks and sterilized at 120° C. for 30 minutes. The medium in each flask was inoculated with 1.6 ml of a frozen seed of *Streptomyces mycarofaciens* SF2772 strain which was then incubated therein at 28° C. for 24 hours under shaking. Next, 1.2 ml of a methanol solution containing 20 mg of the compound (12) was added to each flask in 0.4 ml portions and the incubation was continued at 28° C. for 20 hours under shaking. After the completion of the incubation, the culture was centrifuged at 3000 rpm for 10 minutes. Thus 180 ml of a transparent culture supernatant was obtained while the solid matters including the cells were removed. 180 ml of water was added to these solid matters and the mixture was stirred followed by centrifugation. The washing liquor thus obtained was combined with the abovementioned transparent culture supernatant. After adjusting the mixture to pH 9 with a 1N aqueous solution of sodium hydroxide, the conversion product was extracted with 360 ml portions of ethyl acetate twice. The ethyl acetate layer was dried over anhydrous sodium sulfate and then filtered. The filtrate was concentrated under reduced pressure and the residue thus obtained was purified by preparative TLC [developing system: hexane/acetone (1:1)]. Thus 15.0 mg of a crude compound (3) was obtained. This crude product was purified by Sephadex LH-20 column chromatography (bed volume: 20 ml, methanol) to thereby give 11.4 mg of the compound (3).

While the invention has been described in detail and with reference to specific examples thereof, it will be apparent to one skilled in the art that various changes and modifications can be made therein without departing from the spirit and scope thereof.

What is claimed is:

1. A compound represented by the formula (I):

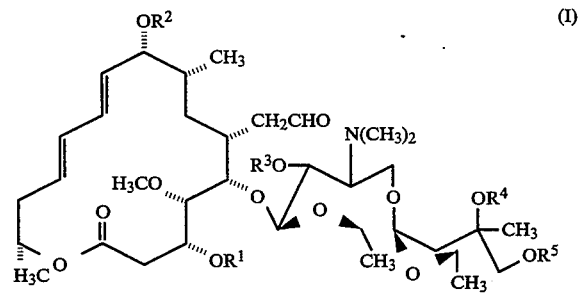

wherein $R^1$ represents a hydrogen atom or a $COR^6$ group, wherein $R^6$ represents a straight-chain alkyl group having 1 to 3 carbon atoms; $R^2$ represents a hydrogen atom or a $COR^6$ group, wherein $R^6$ is as defined above; $R^3$ represents a hydrogen atom or a $COR^6$ group, wherein $R^6$ is as defined above; $R^4$ represents a straight-chain alkyl group having 1 to 4 carbon atoms or a substituted or unsubstituted allyl group; and $R^5$ represents a substituted or unsubstituted, straight-chain or branched alkyl, alkenyl or aralkyl group having 1 to 10 carbon atoms; or a pharmaceutically acceptable salt thereof.

2. The compound as claimed in claim 1, wherein $R^1$ is a propionyl group, $R^2$ is a hydrogen atom, $R^3$ is a hydrogen atom, $R^4$ is a methyl group and $R^5$ is an allyl group or a pharmaceutically acceptable salt thereof.

3. The compound as claimed in claim 1, wherein $R^1$ is a propionyl group, $R^2$ is a hydrogen atom, $R^3$ is a hydrogen atom, $R^4$ is a methyl group and $R^5$ is a n-butyl group or a pharmaceutically acceptable salt thereof.

4. The compound as claimed in claim 1, wherein $R^1$ is a propionyl group, $R^2$ is a hydrogen atom, $R^3$ is a hydrogen atom, $R^4$ is a methyl group and $R^5$ is an isoamyl group or a pharmaceutically acceptable salt thereof.

5. The compound as claimed in claim 1, wherein $R^1$ is a propionyl group, $R^2$ is an acetyl group, $R^3$ is a hydrogen atom, $R^4$ is a methyl group and $R^5$ is an isoamyl group or a pharmaceutically acceptable salt thereof.

6. The compound as claimed in claim 1, wherein $R^1$ is a propionyl group, $R^2$ is a hydrogen atom, $R^3$ is a hydrogen atom, $R^4$ is a methyl group and $R^5$ is a hexyl group or a pharmaceutically acceptable salt thereof.

7. The compound as claimed in claim 1, wherein $R^1$ is a propionyl group, $R^2$ is a hydrogen atom, $R^3$ is a hydrogen atom, $R^4$ is a methyl group and $R^5$ is a benzyl group or a pharmaceutically acceptable salt thereof.

8. The compound as claimed in claim 1, wherein $R^1$ is a hydrogen atom, $R^2$ is a hydrogen atom, $R^3$ is a hydrogen atom, $R^4$ is a methyl group and $R^5$ is a methyl group or a pharmaceutically acceptable salt thereof.

9. The compound as claimed in claim 1, wherein $R^1$ is a hydrogen atom, $R^2$ is a hydrogen atom, $R^3$ is a hydrogen atom, $R^4$ is a methyl group and $R^5$ is an ethyl group or a pharmaceutically acceptable salt thereof.

10. The compound as claimed in claim 1, wherein $R^1$ is a hydrogen atom, $R^2$ is a hydrogen atom, $R^3$ is a hydrogen atom, $R^4$ is a methyl group and $R^5$ is a n-propyl group or a pharmaceutically acceptable salt thereof.

11. The compound as claimed in claim 1, wherein $R^1$ is a hydrogen atom, $R^2$ is a hydrogen atom, $R^3$ is a hydrogen atom, $R^4$ is a methyl group and $R^5$ is a n-butyl group or a pharmaceutically acceptable salt thereof.

12. The compound as claimed in claim 1, wherein $R^1$ is a hydrogen atom, $R^2$ is a hydrogen atom, $R^3$ is a hydrogen atom, $R^4$ is a methyl group and $R^5$ is a n-pentyl group or a pharmaceutically acceptable salt thereof.

13. The compound as claimed in claim 1, wherein $R^1$ is a hydrogen atom, $R^2$ is a hydrogen atom, $R^3$ is a hydrogen atom, $R^4$ is a methyl group and $R^5$ is an isoamyl group or a pharmaceutically acceptable salt thereof.

14. The compound as claimed in claim 1, wherein $R^1$ is a hydrogen atom, $R^2$ is an acetyl group, $R^3$ is a hydrogen atom, $R^4$ is a methyl group and $R^5$ is an isoamyl group or a pharmaceutically acceptable salt thereof.

15. The compound as claimed in claim 1, wherein $R^1$ is a hydrogen atom, $R^2$ is a hydrogen atom, $R^3$ is a hydrogen atom, $R^4$ is an ethyl group and $R^5$ is an isoamyl group or a pharmaceutically acceptable salt thereof.

16. The compound as claimed in claim 1, wherein $R^1$ is a hydrogen atom, $R^2$ is a hydrogen atom, $R^3$ is a hydrogen atom, $R^4$ is a n-propyl group and $R^5$ is an isoamyl group or a pharmaceutically acceptable salt thereof.

17. The compound as claimed in claim 1, wherein $R^1$ is a hydrogen atom, $R^2$ is a hydrogen atom, $R^3$ is a hydrogen atom, $R^4$ is a methyl group and $R^5$ is a benzyl group or a pharmaceutically acceptable salt thereof.

18. A antimicrobial composition comprising a compound represented by the formula (I):

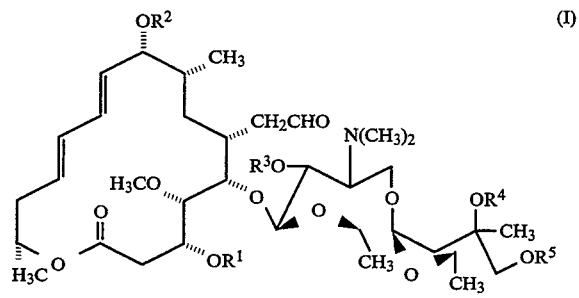

wherein $R^1$ represents a hydrogen atom or a $COR^6$ group, wherein $R^6$ represents a straight-chain alkyl group having 1 to 3 carbon atoms; $R^2$ represents a hydrogen atom or a $COR^6$ group, wherein $R^6$ is as defined above; $R^3$ represents a hydrogen atom or a $COR^6$ group, wherein $R^6$ is as defined above; $R^4$ represents a straight-chain alkyl group having 1 to 4 carbon atoms or a substituted or unsubstituted allyl group; and $R^5$ represents a substituted or unsubstituted, straight-chain or branched alkyl, alkenyl or aralkyl group having 1 to 10 carbon atoms; or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 5,407,918
DATED : April 18, 1995
INVENTOR(S) : Keiichi Ajito et al.

It is certified that error appears in the above-indentified patent and that said Letters Patent is hereby corrected as shown below:

Item [57], ABSTRACT:

Line 3, Formula (I) should read as follows:

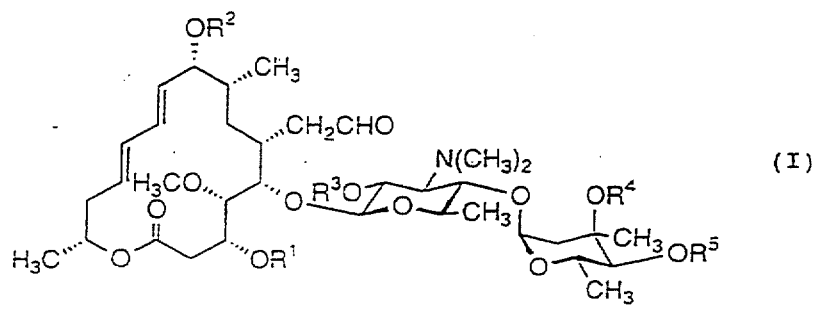

Column 4, lines 41 to 51, Formula (I) should read as follow:

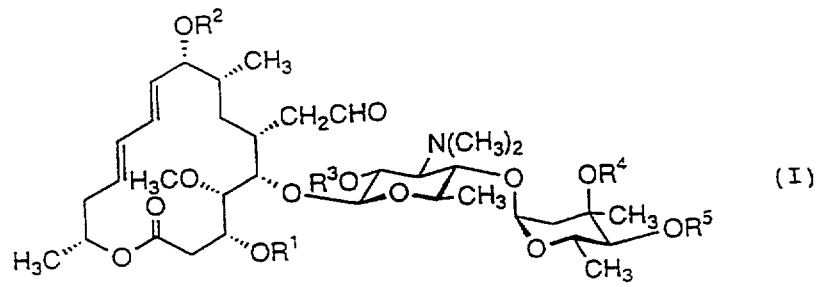

UNITED STATES PATENT AND TRADEMARK OFFICE
CERTIFICATE OF CORRECTION

PATENT NO. : 5,407,918
DATED : April 18, 1995
INVENTOR(S) : Keiichi Ajito et al.

It is certified that error appears in the above-indentified patent and that said Letters Patent is hereby corrected as shown below:

Column 5, lines 1 to 10, Formula (III) should read as follows:

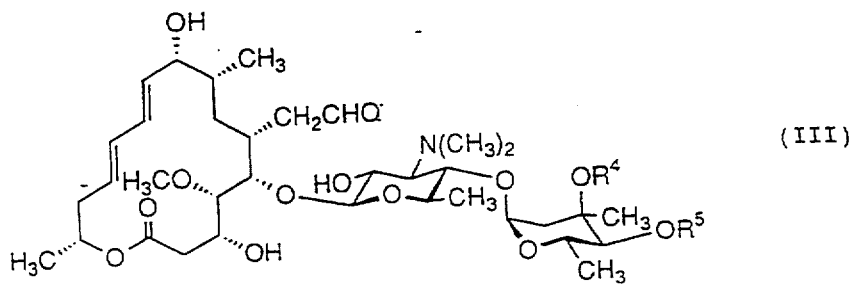

Column 5, lines 20 to 30, Formula (II) should read as follows:

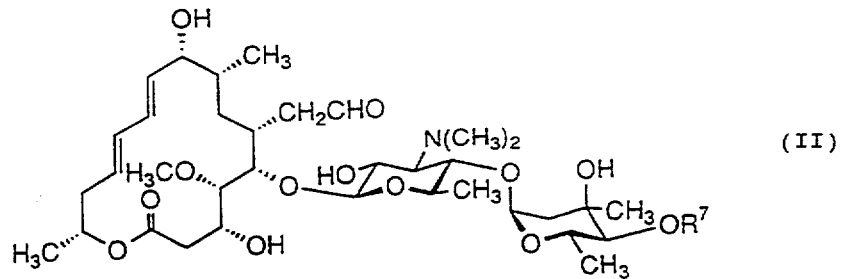

UNITED STATES PATENT AND TRADEMARK OFFICE
CERTIFICATE OF CORRECTION

PATENT NO. : 5,407,918
DATED : April 18, 1995
INVENTOR(S) : Keiichi Ajito et al.

It is certified that error appears in the above-indentified patent and that said Letters Patent is hereby corrected as shown below:

Column 6, lines 34 to 44, Formula (IV) should read as follows:

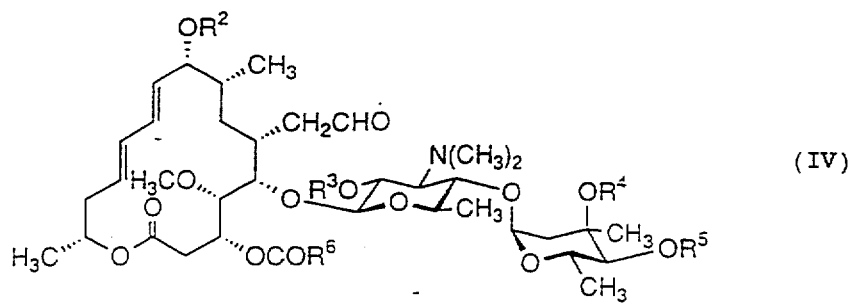

(IV)

Column 7, lines 1 to 10, Formula (V) should read as follows:

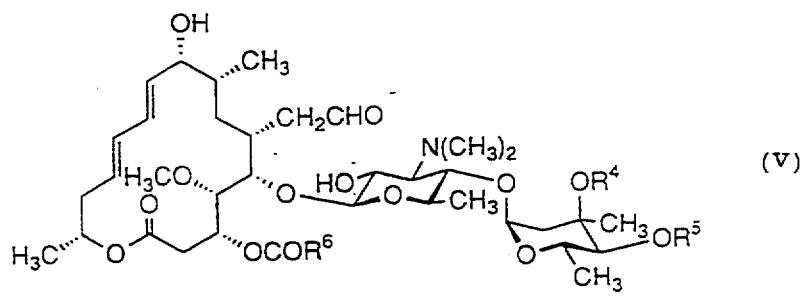

(V)

UNITED STATES PATENT AND TRADEMARK OFFICE
CERTIFICATE OF CORRECTION

PATENT NO. : 5,407,918
DATED : April 18, 1995
INVENTOR(S) : Keiichi Ajito et al.

It is certified that error appears in the above-indentified patent and that said Letters Patent is hereby corrected as shown below:

Column 7, lines 27 to 37, Formula (VI) should read as follows:

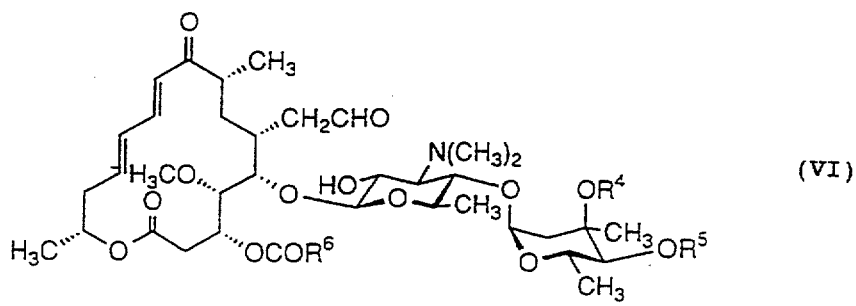

(VI)

Column 11, lines 1 to 10, Formula (VII) should read as follows:

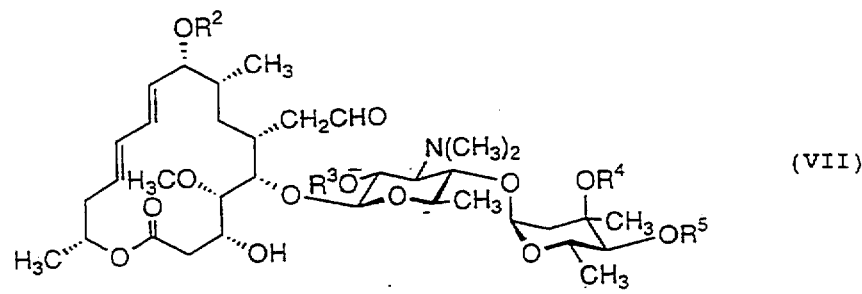

(VII)

UNITED STATES PATENT AND TRADEMARK OFFICE
CERTIFICATE OF CORRECTION

PATENT NO. : 5,407,918
DATED : April 18, 1995
INVENTOR(S) : Keiichi Ajito et al.

It is certified that error appears in the above-indentified patent and that said Letters Patent is hereby corrected as shown below:

Column 11, lines 50 to 60, Formula (III) should read as follows:

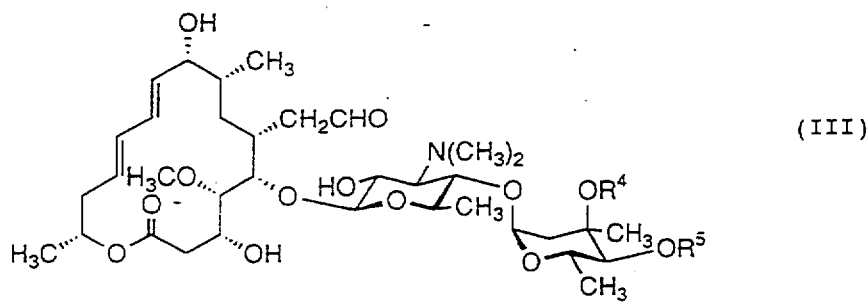

(III)

Column 12, lines 21 to 31, Formula (V) should read as follows:

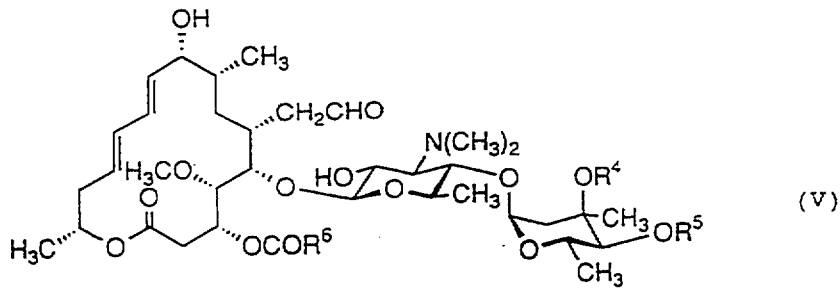

(V)

UNITED STATES PATENT AND TRADEMARK OFFICE
CERTIFICATE OF CORRECTION

PATENT NO. : 5,407,918

DATED : April 18, 1995

INVENTOR(S) : Keiichi Ajito et al.

It is certified that error appears in the above-indentified patent and that said Letters Patent is hereby corrected as shown below:

Column 14, lines 52 to 62, Formula (III) should read as follows:

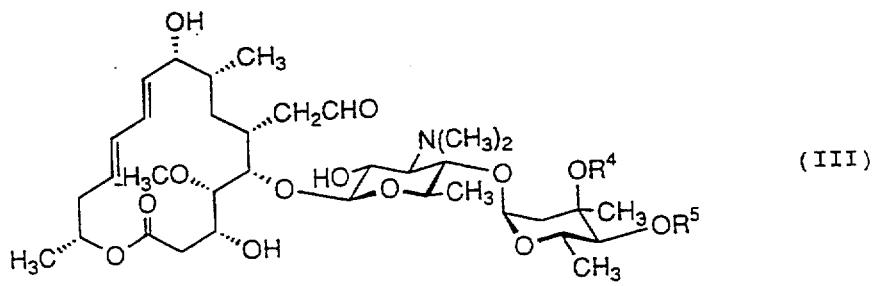

Column 15, lines 4 to 14, Formula (II) should read as follows:

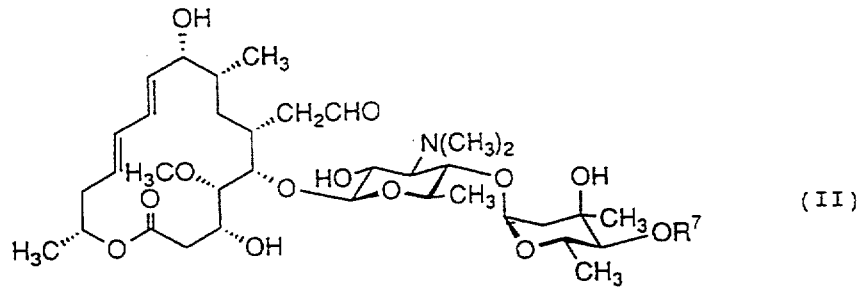

UNITED STATES PATENT AND TRADEMARK OFFICE
CERTIFICATE OF CORRECTION

PATENT NO. : 5,407,918
DATED : April 18, 1995
INVENTOR(S) : Keiichi Ajito et al.

It is certified that error appears in the above-indentified patent and that said Letters Patent is hereby corrected as shown below:

Column 16, lines 20 to 65, Reaction Scheme 1-1 should read as follows:

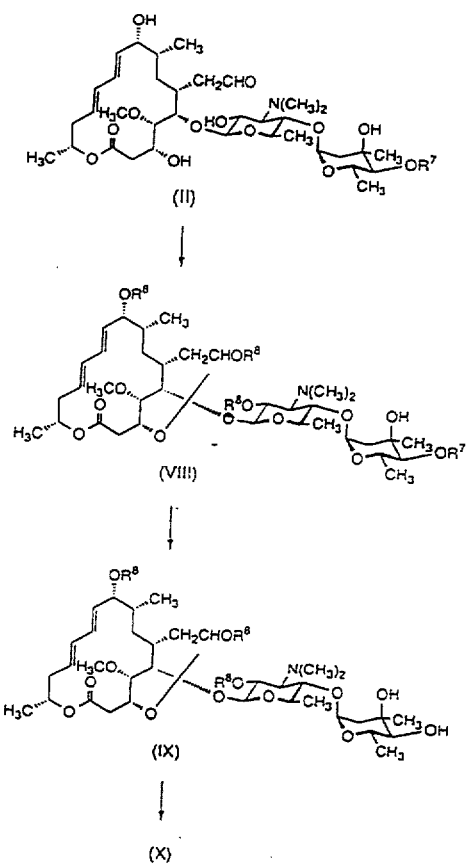

UNITED STATES PATENT AND TRADEMARK OFFICE
CERTIFICATE OF CORRECTION

PATENT NO. : 5,407,918
DATED : April 18, 1995
INVENTOR(S) : Keiichi Ajito et al.

It is certified that error appears in the above-indentified patent and that said Letters Patent is hereby corrected as shown below:

Column 17, lines 1 to 47, Reaction Scheme 1-2 should read as follows:

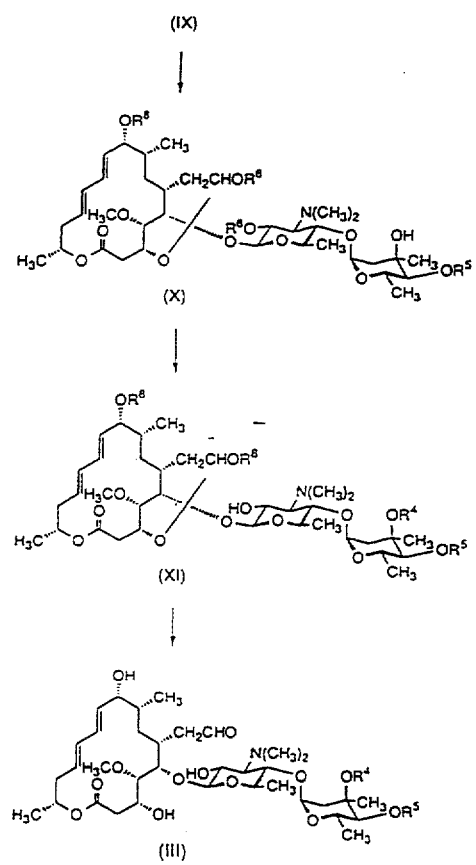

UNITED STATES PATENT AND TRADEMARK OFFICE
CERTIFICATE OF CORRECTION

PATENT NO. : 5,407,918
DATED : April 18, 1995
INVENTOR(S) : Keiichi Ajito et al.

It is certified that error appears in the above-indentified patent and that said Letters Patent is hereby corrected as shown below:

Claim 1, column 58, lines 32 to 42, Formula (I) should read as follows:

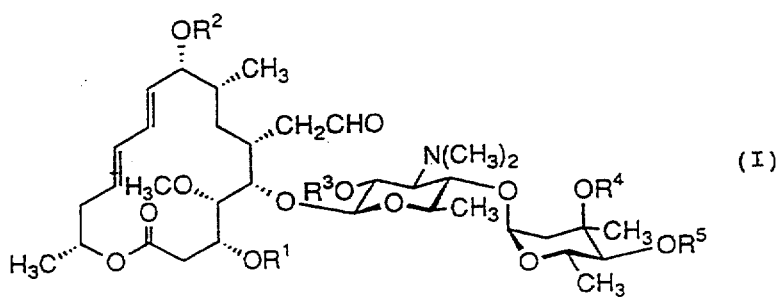

UNITED STATES PATENT AND TRADEMARK OFFICE
CERTIFICATE OF CORRECTION

PATENT NO. : 5,407,918
DATED : April 18, 1995
INVENTOR(S) : Keiichi Ajito et al.

It is certified that error appears in the above-indentified patent and that said Letters Patent is hereby corrected as shown below:

Claim 18, column 60, lines 17 to 27, Formula (I) should read as follows:

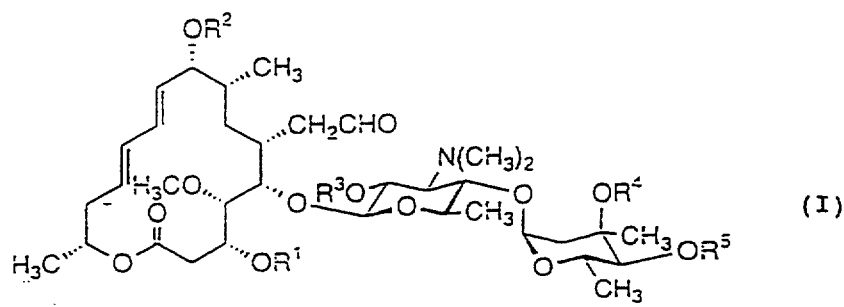

Signed and Sealed this

Sixteenth Day of July, 1996

Attest:

BRUCE LEHMAN

*Attesting Officer*    *Commissioner of Patents and Trademarks*